US008224414B2

(12) United States Patent
Kellogg et al.

(10) Patent No.: US 8,224,414 B2
(45) Date of Patent: Jul. 17, 2012

(54) SYSTEM AND METHOD FOR ANALYTE SAMPLING AND ANALYSIS WITH HYDROGEL

(75) Inventors: Scott C. Kellogg, Boston, MA (US); Han Chuang, Canton, MA (US)

(73) Assignee: Echo Therapeutics, Inc., Franklin, MA (US)

(*) Notice: Subject to any disclaimer, the term of this patent is extended or adjusted under 35 U.S.C. 154(b) by 1070 days.

(21) Appl. No.: 11/223,971

(22) Filed: Sep. 13, 2005

(65) Prior Publication Data

US 2006/0094946 A1     May 4, 2006

Related U.S. Application Data

(60) Division of application No. 11/201,334, filed on Aug. 11, 2005, now abandoned, which is a continuation of application No. 10/974,963, filed on Oct. 28, 2004, now abandoned.

(51) Int. Cl.
    *A61B 5/05*     (2006.01)
    *A61B 5/00*     (2006.01)
    *C12Q 1/54*     (2006.01)
    *G01N 33/50*     (2006.01)

(52) U.S. Cl. ..... 600/347; 600/345; 600/365; 205/777.5; 205/778; 435/14

(58) Field of Classification Search ................ 600/345, 600/347, 365; 435/14; 205/777.5, 778
See application file for complete search history.

(56) References Cited

U.S. PATENT DOCUMENTS

| 3,551,554 A | 12/1970 | Herschler |
| 3,711,602 A | 1/1973 | Herschler |
| 3,711,606 A | 1/1973 | Herschler |
| 3,828,769 A | 8/1974 | Mettier |

(Continued)

FOREIGN PATENT DOCUMENTS

CA     2196746     8/1991

(Continued)

OTHER PUBLICATIONS

Agrawl, C.M. et al., "The effects of ultrasound irradiation on a biodegradable 50-50% copolymer of polylactic and polyglycolic acids," 28 Journal of Biomedical Materials Research 851-859 (1994).

(Continued)

*Primary Examiner* — Patricia Mallari
*Assistant Examiner* — Christian Jang
(74) *Attorney, Agent, or Firm* — Pabst Patent Group LLP

(57) ABSTRACT

The invention relates to a transdermal analyte monitoring system comprising a medium adapted to interface with a biological membrane and to receive an analyte from the biological membrane and an electrode assembly comprising a plurality of electrodes, wherein the medium is adapted to react continuously with the analyte, an electrical signal is detected by the electrode assembly, and the electrical signal correlates to an analyte value. The analyte value may be the flux of the analyte through the biological membrane or the concentration of the analyte in a body fluid of a subject. The medium may comprise a vinyl acetate based hydrogel, an agarose based hydrogel, or a polyethylene glycol diacrylate (PEG-DA) based hydrogel, for example. The surface region of the electrode may comprise pure platinum. The system may include an interference filter located between the biological membrane and the electrode assembly for reducing interference in the system. The system may comprise a processor programmed to implement an error correction method that corrects for sensor drift.

9 Claims, 27 Drawing Sheets

U.S. PATENT DOCUMENTS

| | | |
|---|---|---|
| 4,002,221 A | 1/1977 | Buchalter |
| 4,020,830 A | 5/1977 | Johnson et al. |
| 4,127,125 A | 11/1978 | Takemoto et al. |
| 4,144,646 A | 3/1979 | Takemoto et al. |
| 4,176,664 A | 12/1979 | Kalish |
| 4,249,531 A | 2/1981 | Heller et al. |
| 4,280,494 A | 7/1981 | Cosgrove et al. |
| 4,309,989 A | 1/1982 | Fahim |
| 4,372,296 A | 2/1983 | Fahim |
| 4,457,748 A | 7/1984 | Lattin |
| 4,537,776 A | 8/1985 | Cooper |
| 4,557,943 A | 12/1985 | Rosler et al. |
| 4,563,184 A | 1/1986 | Korol |
| 4,595,011 A | 6/1986 | Philips |
| 4,646,725 A | 3/1987 | Moasser |
| 4,657,543 A | 4/1987 | Langer et al. |
| 4,683,242 A | 7/1987 | Poser |
| 4,698,058 A | 10/1987 | Greenfeld et al. |
| 4,732,153 A | 3/1988 | Philips |
| 4,767,402 A | 8/1988 | Kost et al. |
| 4,779,806 A | 10/1988 | Langer et al. |
| 4,780,212 A | 10/1988 | Kost et al. |
| 4,786,277 A | 11/1988 | Powers |
| 4,787,070 A | 11/1988 | Suzuki et al. |
| 4,787,888 A | 11/1988 | Fox |
| 4,805,623 A | 2/1989 | Jobsis et al. |
| 4,820,720 A | 4/1989 | Sanders et al. |
| 4,821,733 A | 4/1989 | Peck |
| 4,821,740 A | 4/1989 | Tachibana et al. |
| 4,834,978 A | 5/1989 | Nuwayser |
| 4,855,298 A | 8/1989 | Yamada et al. |
| 4,860,058 A | 8/1989 | Kobayashi et al. |
| 4,863,970 A | 9/1989 | Patel et al. |
| 4,866,050 A | 9/1989 | Ben-Amoz |
| 4,933,062 A | 6/1990 | Shaw et al. |
| 4,948,587 A | 8/1990 | Kost et al. |
| 4,953,552 A | 9/1990 | DeMarzo |
| 4,953,565 A | 9/1990 | Tachibana et al. |
| 4,970,145 A | 11/1990 | Bennetto et al. |
| 4,981,779 A | 1/1991 | Wagnet |
| 4,986,271 A | 1/1991 | Wilkins |
| 5,001,051 A | 3/1991 | Miller et al. |
| 5,006,342 A | 4/1991 | Cleary et al. |
| 5,007,438 A | 4/1991 | Tachibana et al. |
| 5,016,615 A | 5/1991 | Driller et al. |
| 5,019,034 A | 5/1991 | Weaver et al. |
| 5,050,604 A | 9/1991 | Reshef et al. |
| 5,069,908 A | 12/1991 | Henley |
| 5,076,273 A | 12/1991 | Schoendorfer et al. |
| 5,078,144 A | 1/1992 | Sekino et al. |
| 5,082,786 A | 1/1992 | Nakamoto |
| 5,086,229 A | 2/1992 | Rosenthal et al. |
| 5,115,805 A | 5/1992 | Bommannan et al. |
| 5,118,404 A | 6/1992 | Saito |
| 5,119,819 A | 6/1992 | Thomas et al. |
| 5,120,544 A | 6/1992 | Henley |
| 5,134,057 A | 7/1992 | Kuypers et al. |
| 5,135,753 A | 8/1992 | Baker et al. |
| 5,139,023 A | 8/1992 | Stanley et al. |
| 5,140,985 A | 8/1992 | Schroeder et al. |
| 5,161,532 A | 11/1992 | Joseph |
| 5,165,407 A | 11/1992 | Wilson et al. |
| 5,165,418 A | 11/1992 | Tankovich |
| 5,171,215 A | 12/1992 | Flanagan |
| 5,197,946 A | 3/1993 | Tachibana |
| 5,215,520 A | 6/1993 | Shroot et al. |
| 5,215,887 A | 6/1993 | Saito |
| 5,230,334 A | 7/1993 | Klopotek |
| 5,231,975 A | 8/1993 | Bommannan et al. |
| 5,236,410 A | 8/1993 | Granov et al. |
| 5,250,419 A | 10/1993 | Bernard et al. |
| 5,267,985 A | 12/1993 | Shimada et al. |
| 5,279,543 A | 1/1994 | Glikfeld et al. |
| 5,282,785 A | 2/1994 | Shapland et al. |
| 5,286,254 A | 2/1994 | Shapland et al. |
| 5,315,998 A | 5/1994 | Tachibana et al. |
| 5,323,769 A | 6/1994 | Bommannan et al. |
| 5,330,756 A | 7/1994 | Steuart et al. |
| 5,362,307 A | 11/1994 | Guy et al. |
| 5,364,838 A | 11/1994 | Rubsamen |
| 5,386,837 A | 2/1995 | Sterzer |
| 5,401,237 A | 3/1995 | Tachibana et al. |
| 5,405,366 A | 4/1995 | Fox et al. |
| 5,405,614 A | 4/1995 | D'Angelo et al. |
| 5,413,550 A | 5/1995 | Castel |
| 5,415,629 A | 5/1995 | Henley |
| 5,421,816 A | 6/1995 | Lipkovker |
| 5,429,735 A | 7/1995 | Johnson et al. |
| 5,443,080 A | 8/1995 | D'Angelo et al. |
| 5,445,611 A | 8/1995 | Eppstein et al. |
| 5,458,140 A | 10/1995 | Eppstein et al. |
| 5,470,582 A | 11/1995 | Supersaxo et al. |
| 5,534,496 A | 7/1996 | Lee et al. |
| 5,538,503 A | 7/1996 | Henley |
| 5,550,178 A * | 8/1996 | Desai et al. ..................... 524/56 |
| 5,569,198 A | 10/1996 | Racchini |
| 5,573,778 A | 11/1996 | Therriault et al. |
| 5,582,184 A | 12/1996 | Erickson et al. |
| 5,582,586 A | 12/1996 | Tachibana et al. |
| 5,617,851 A | 4/1997 | Lipkovker |
| 5,618,275 A | 4/1997 | Bock |
| 5,626,554 A | 5/1997 | Ryaby et al. |
| 5,636,632 A | 6/1997 | Bommannan et al. |
| 5,646,221 A | 7/1997 | Inagi et al. |
| 5,655,539 A | 8/1997 | Wang et al. |
| 5,656,016 A | 8/1997 | Ogden |
| 5,658,247 A | 8/1997 | Henley |
| 5,667,487 A | 9/1997 | Henley |
| 5,722,397 A | 3/1998 | Eppstein |
| 5,730,714 A | 3/1998 | Guy et al. |
| 5,735,273 A | 4/1998 | Kurnik et al. |
| 5,746,217 A | 5/1998 | Erickson et al. |
| 5,771,890 A | 6/1998 | Tamada |
| 5,814,599 A | 9/1998 | Mitragotri et al. |
| 5,820,570 A | 10/1998 | Erickson et al. |
| 5,827,183 A | 10/1998 | Kurnik et al. |
| 5,851,438 A | 12/1998 | Chan |
| 5,885,211 A | 3/1999 | Eppstein et al. |
| 5,902,603 A | 5/1999 | Chen et al. |
| 5,906,830 A | 5/1999 | Farinas et al. |
| 5,947,921 A | 9/1999 | Johnson et al. |
| 5,961,451 A | 10/1999 | Reber et al. |
| 5,989,409 A | 11/1999 | Kurnik et al. |
| 6,002,961 A | 12/1999 | Mitragotri et al. |
| 6,002,962 A | 12/1999 | Huang et al. |
| 6,009,343 A | 12/1999 | Shain et al. |
| 6,018,678 A | 1/2000 | Mitragotri et al. |
| 6,041,253 A | 3/2000 | Kost et al. |
| 6,153,211 A * | 11/2000 | Hubbell et al. ................ 424/426 |
| 6,190,315 B1 | 2/2001 | Kost et al. |
| 6,212,416 B1 | 4/2001 | Ward et al. |
| 6,233,471 B1 | 5/2001 | Berner et al. |
| 6,234,990 B1 | 5/2001 | Rowe et al. |
| 6,251,083 B1 | 6/2001 | Yum et al. |
| 6,283,926 B1 | 9/2001 | Cunningham et al. |
| 6,287,438 B1 | 9/2001 | Knoll |
| 6,299,578 B1 | 10/2001 | Kurnik et al. |
| 6,309,351 B1 | 10/2001 | Kurnik et al. |
| 6,468,229 B1 | 10/2002 | Grace et al. |
| 6,482,604 B2 | 11/2002 | Kwon |
| 6,487,447 B1 | 11/2002 | Weimann et al. |
| 6,491,657 B2 | 12/2002 | Rowe et al. |
| 6,503,198 B1 | 1/2003 | Aronowtiz et al. |
| 6,535,753 B1 | 3/2003 | Raskas |
| 6,540,675 B2 | 4/2003 | Aceti et al. |
| 6,585,765 B1 * | 7/2003 | Hossainy et al. ............. 623/1.45 |
| 6,595,919 B2 | 7/2003 | Berner et al. |
| 6,673,596 B1 | 1/2004 | Sayler et al. |
| 6,766,817 B2 | 7/2004 | de Silva |
| 6,887,239 B2 | 5/2005 | Elstrom et al. |
| 6,931,327 B2 | 8/2005 | Goode, Jr. et al. |
| 2001/0017269 A1 | 8/2001 | Heller et al. |
| 2001/0020125 A1* | 9/2001 | Kurnik et al. .................. 600/347 |
| 2002/0082517 A1* | 6/2002 | Klein ............................ 600/564 |
| 2002/0128546 A1 | 9/2002 | Silver |
| 2002/0183604 A1* | 12/2002 | Gowda et al. .................. 600/345 |
| 2003/0027240 A1 | 2/2003 | Asher et al. |

| | | | |
|---|---|---|---|
| 2003/0100040 A1 | 5/2003 | Bonnecaze et al. | |
| 2003/0100846 A1 | 5/2003 | Custer et al. | |
| 2003/0113934 A1* | 6/2003 | Kwon | 436/164 |
| 2003/0134294 A1* | 7/2003 | Sandford et al. | 435/6 |
| 2003/0199745 A1* | 10/2003 | Burson et al. | 600/347 |
| 2003/0232895 A1 | 12/2003 | Omidian et al. | |
| 2004/0039418 A1 | 2/2004 | Elstrom et al. | |
| 2004/0087671 A1 | 5/2004 | Tamada et al. | |
| 2004/0111017 A1* | 6/2004 | Say et al. | 600/347 |
| 2004/0167383 A1 | 8/2004 | Kim et al. | |
| 2004/0171980 A1 | 9/2004 | Mitragotri et al. | |
| 2004/0176672 A1 | 9/2004 | Silver et al. | |
| 2004/0236268 A1 | 11/2004 | Mitragotri et al. | |
| 2005/0027180 A1 | 2/2005 | Goode, Jr. et al. | |
| 2006/0015058 A1 | 1/2006 | Kellogg et al. | |

FOREIGN PATENT DOCUMENTS

| | | |
|---|---|---|
| CA | 1324051 | 11/1993 |
| CA | 2167393 | 1/1995 |
| CA | 2226176 | 1/1997 |
| CA | 2229480 | 3/1997 |
| CA | 2212826 | 7/1997 |
| CA | 2075624 | 11/1997 |
| DE | 2756460 | 6/1979 |
| EP | 0 043 738 | 1/1982 |
| EP | 0 245 535 | 11/1987 |
| EP | 0 246 341 | 11/1987 |
| EP | 0 247 850 | 12/1987 |
| EP | 0 278 074 | 8/1988 |
| EP | 0 304 304 | 2/1989 |
| EP | 0 368 408 | 5/1990 |
| EP | 0 453 283 | 10/1991 |
| EP | 0 495 531 | 7/1992 |
| EP | 0 513 789 | 11/1992 |
| EP | 0 612 525 | 8/1994 |
| EP | 0 625 360 | 11/1994 |
| EP | 0 649 628 | 4/1995 |
| EP | 0 736 305 | 10/1996 |
| EP | 1 266 608 | 12/2002 |
| GB | 1 577 551 | 2/1977 |
| GB | 1 577 551 | 10/1980 |
| GB | 2 153 223 | 12/1984 |
| GB | 3 170 172 | 7/1991 |
| JP | 59-95060 | 5/1984 |
| JP | 62-133937 | 6/1987 |
| JP | 3366646 | 11/2002 |
| JP | 2002/542498 | 12/2002 |
| JP | 2003/527613 | 9/2003 |
| SU | 445 433 | 11/1974 |
| SU | 556 805 | 6/1977 |
| SU | 591186 | 1/1978 |
| SU | 506 421 | 2/1978 |
| SU | 910157 | 3/1982 |
| WO | 87/07295 | 12/1987 |
| WO | 88/00001 | 1/1988 |
| WO | 90/01971 | 3/1990 |
| WO | 90/15568 | 12/1990 |
| WO | 91/12772 | 9/1991 |
| WO | 92/13567 | 8/1992 |
| WO | 94/05368 | 8/1992 |
| WO | 92/14449 | 9/1992 |
| WO | 93/05096 | 3/1993 |
| WO | 93/20745 | 10/1993 |
| WO | 94/08655 | 4/1994 |
| WO | 95/02357 | 1/1995 |
| WO | 96/00110 | 1/1996 |
| WO | 97/02811 | 1/1997 |
| WO | 97/04832 | 2/1997 |
| WO | 97/10499 | 3/1997 |
| WO | WO 97/10356 | 3/1997 |
| WO | 97/13548 | 4/1997 |
| WO | 97/18851 | 5/1997 |
| WO | 97/24059 | 7/1997 |
| WO | 97/30628 | 8/1997 |
| WO | 97/30749 | 8/1997 |
| WO | 98/00194 | 1/1998 |
| WO | 98/71184 | 4/1998 |
| WO | 98/20331 | 5/1998 |
| WO | 98/28037 | 7/1998 |
| WO | 98/34541 | 8/1998 |
| WO | 98/42252 | 10/1998 |
| WO | 99/34857 | 7/1999 |
| WO | 99/34858 | 7/1999 |
| WO | 00/04821 | 2/2000 |
| WO | 00/35351 | 6/2000 |
| WO | 00/35357 | 6/2000 |
| WO | WO 00/64533 | 11/2000 |
| WO | 01/70330 | 9/2001 |
| WO | WO 01/70330 | 9/2001 |

OTHER PUBLICATIONS

Albin et al., "Theoretical and Experimental Studies of Glucose Sensitive Membranes," 6 Journal of Controlled Release 267-291 (1987).

Allcock, H., et al., "Activity of Urea Amidohydrolase Immobilized within Poly[di(methoxy-ethoxyethoxy)phosphazene Hydrogels," Biomaterials, vol. 15, No. 7, pp. 502-506 (Jun. 1994).

Apfel, R. F., "Possibility of Microcavitation from Diagnostic Ultrasound," IEEE Trans. Ultrason Ferroelectrics Freq. Control UFFC 33:139-142 (1986).

Asakura et al. "Immobilization of Glucose Oxidase on Nonwoven Fabrics with *Bombyx mori* Silk Fibroin Gel," Journal of Applied Polymer Science, vol. 46, No. 1, pp. 49-53 (Sep. 5, 1992).

Aungst et al., "Contributions of Drug Solubilization, Partitioning, Barrier Disruption, and Solvent Permeation to the Enhancement of Skin Permeation of Various Compounds with Fatty Acids and Amines," Pharm. Res. 7:712-718 (1990).

Barry, "Mode of Action of Penetration Enhancers in Human Skin," J. Controlled Rel. 6:85-97 (1987).

Bhat, et al., "Optimization of delivery of betamethasone-dipropionate from skin preparation," Indian Drugs 32:211-14 (1995).

Blackshear, "Implantable Drug-Delivery Systems," Scientific America, p. 66-73 (604193) (Dec. 1979).

Bommer, et al., "Subcutaneous Erythropoeitin" The Lancet 406 (1988).

Boucaud et al., "Clinical, histologic, and electron microscopy study of skin exposed to low-frequency ultrasound," The Anatomical Record, vol. 264, No. 1, pp. 114-119 (Sep. 2001).

Boucaud et al., "In vitro study of low-frequency ultrasound-enhanced transdermal transport of fentanyl and caffeine across human and hairless rat skin," International J. Pharmaceuticals, vol. 228, Nos. 1-2, pp. 69-77 (Oct. 2001).

Burnette, R.R., "Iontophoresis," Transdermal Drug Delivery Development Issues and Research Initiatives 247-291 (Hadgraft and Guv. Editors, Marcel Dekker, 1989).

Burton et al., "Metabolism and Transport of Peptide Across Intestinal Mucosa," 14 Proceed. Intern. Symp. Control. Rel. Bioact. Mater 6 (Controlled Release Society, Inc. 1987).

Camel, "Ultrasound," Percutaneous Penetration Enhancers 369-382 (Eric W. Smith et al. eds. 1995).

Cleary, "Transdermal Controlled Release Systems," Medical Applications of Controlled Release 203-251 (Langer and Wise, Editors, CRCPress 1984).

Clegg and Vaz, "Translational diffusion of proteins and lipids in artificial lipid bilayer membranes, A comparison of experiment with theory," Progress in Protein-Lipid Interactions Watts, ed. Chapter 5:173-229 (Elsvier, NY 1985).

D'Emanuele, et al., "An Investigation of the Effects of Ultrasound on Degradable Polyanhydride Matrices," 25 Macromolecules 511-515 (1992).

Davis et al., "Characterization of Recombinant Human Erythropoietin Produced in Chinese Hamster Ovary Cells," Biochemistry 26:2633-2638 (1987).

Domb, et al., "Polyanhydrides-Sysnthesis and Characterization," 107 Advances in Polymer Science: 93-141 (1993).

Ebert et al., "Transbuccal Absorption of Diclofenac Sodium in a Dog Model," Controlled Release Technology Pharmaceutical Application 310-321 (Lee, et al. Editors, American Chemical Society, 1987).

Eggerth et al., "Evaluation of Hamster Cheek Pouch as a Model for Buccal Absorption," 14 Proceed. Intern. Symp. Rel. Bioact. Mater. 180-181 (Controlled Release Society, Inc. 1987).

Egorov, E.A. et al., "Use of the Variants of the Pharmacophysical Influence in Ophthalmology," 102 Ophthalmology Journal #2 (1992).

Elias, "The Microscopic Structure of the Epidermis and Its Derivatives," Percutaneous Absorption: Mechanisms—Methodology—Drug Delivery 1-12 (1989).

Eppstein, D.A. et al., "Alternative Delivery Systems for Peptides and Proteins as Drugs," 5 CRC Reviews in Therapeutic Drug Carrier Systems 99-139 (1988).

Eppstein, D.A. et al., "Applications of Liposome Formulations for Antimicrobial/Antiviral Therapy," Liposomes as Drug Carriers 311-323 (John Wiley & Sons 1988).

Eppstein, D.A. et al., "Medical Utility of Interferons: Approaches to Increasing Therapeutic Efficacy" 7 Pharmacy International 195-199 (1986).

Flynn, "Mechanism of Percutaneous Absorpotion from Physicochemical Evidence," Percutaneous Absorption: Mechanisms—Methodology—Drug Delivery, pp. 27-51 (1989).

Friedman, "Interferons: A Primer," ISBN 0-12-268280-7 (Academic Press, NY 1981).

Gaertner, W., "Frequency Dependence of Ultrasonic Cavitation," J. Acoust. Soc. Am. 26:977-980 (1954).

Ghanem et al., "The effects of ethanol on the transport of lipophilic and polar permeants across hairless mouse skin: Methods/validation of a novel approach," Int. J. Pharm. 78:137-156 (1992).

Grups and Frohmuller, "Cyclic Interferon Gamma Treatment of Patients with Metastatic Renal Carcinoma," J. Med. 64(3):218-220 (1989).

Hansch and Leo, "Substitutent Constants for Correlation Analysis in Chemistry and Biology" (1979).

Heller, J., et al. "Controlled Drug Release by Polymer Dissolution II Enzyme-Mediated Delivery Device," Journal of Pharmaceutical Sciences, vol. 68, No. 7, pp. 919-921 (Jul. 1979).

Hill-West et al. (1994) Inhibition of thrombosis and intimal thickening after balloon injury by in situ polymerization of thin hydrogel barriers. PNAS USA 91: 5967-71.

Johnson et al., "Synergistic Effects of Chemical Enhancers and Therapeutic Ultrasound on Transdermal Drug Delivery," 85 J. Pharmaceutical Sciences 670-679 (Jul. 1996).

Junginger et al., "Visualization of Drug Transport Across Human Skin and the Influence of Penetration Enhancers," Drug Permeation Enhancement 59-89 (1994).

Kamath, et al., "Biodegradable hydrogels in Drug Delivery," 11 Advanced Drug Delivery Reviews 59-84 (1993).

Kasting et al., "Prodrugs for Dermal Delivery: Solubility, Molecular Size, and Functional Group Effects," Prodrugs: Topical and Ocular Delivery 117-161 (1992).

Keith and W. Snipes, "Polymeric Carriers for Active Agents," Transdermal and Related Drug Delivery Systems pp. 223-279 (D.A. Jones ed. 1984).

Kost and Langer, "Ultrasound-Mediated Transdermal Drug Delivery," Topical Drug Bioavailability Bioequivalence and Penetration 91-104 (1993).

Kost et al., "Ultrasound Effect on Transdermal Drug Delivery," Ben Gurion University, Dept. of Chem. Engineering, Beer Sheva Israel MIT, Dept. of Applied Biological Sciences, Cambridge, MA.

Kost, J., et al., "Glucose-Sensitive Membranes Containing Glucose Oxidase: Activity, Swelling, and Permeability Studies," Journal of Biomedical Materials Research, vol. 19, pp. 1117-1133 (1985).

Krall, "World Book of Diabetes in Practice," vol. 3, pp. 2-7 (Elsvier, 1988).

Langer et al., "Chemical and Physical Structure of Polymers as Carriers for Controlled Release of Bioactive Agents: A Review," Journal of Macromolecular Science, Reviews on Macromolecular Chemistry and Physics, C23(1), 61-126 (1983).

Lee & Rashi, "Nasal Peptide and Protein Absorption Promotors: Aminopeptidase Inhibition as a Predictor of Absorption Enhancement Potency of Bile Salts," Proceed. Intern. Symp. Control. Rel. Bioact. Mater. 14, 53-54 (1987).

Lee et al., "Protease Inhibition as an Additional Mechanism for the Nasal Absorpotion Enhancement Effect of Sodium Taurodihydrofusidate," Proceed. Intern. Symp. Control. Rel. Bioact. Mater. 14, 55-56 (1987).

Lesho et al., "A Photopatterned Glucose Responsive Hydrogel for Use in a Conductimetric Sensor," Biomaterials for Drug and Cell Delivery, Materials Research Society Symposium Proceedings, vol. 331, pp. 193-198 (1994).

Levy et al., "Effect of Ultrasound on Transdermal Drug Delivery to Rats and Guinea Pigs," J. Clin. Invest. 83:2074-2078 (1989).

Liu et al., "Experimental Approach to Elucidate the Mechanism of Ultrasound-Enhanced Polymer Erosion and Release of Incorporated Substances," 25 Macromolecules 123-128 (1992).

Liu, et al., "Cotransport of Estradiol and Ethanol Through Human Skin In Vitro: Understanding the Permeant/Enhancer Flux Relationship," Pharmaceutical Research 8:938-944 (1991).

Machluf and Kost, "Ultrasonically enhanced transdermal drug delivery, Experimental approaches to elucidate the mechanism," J. Biomater. Sci. Polymer Edn. 5:147-156 (1993).

Mak et al., "Oleic Acid Concentration and Effect in Human Stratum Corneum: Non-Invasive Determination by Attenuated Total Reflectance Infrared Spectroscopy In Vivo,": J. Controlled Rel. 12:67-75 (1990).

Merriam-Webster's Collegiate Dictionary (2001) Merriam-Webster Inc. $10^{th}$ Ed. 250.

Mezei, Michael, "Liposomes as a Skin Drug Delivery System," Topics in Pharmaceutical Sciences pp. 345-357 (1985).

Mitragotri et al., "A Mechanistic Study of Ultrasonically-Enhanced Transdermal Drug Delivery," J. Pharm. Sci. vol. 84, No. 6, pp. 697-706 (1995).

Mitragotri et al., "Ultrasound-Mediated Transdermal Protein Delivery," Science 269:850-853 (Aug. 11, 1995).

Mitragotri et al., "Sonophoresis: Enhanced Transdermal Drug Delivery by Application of Ultrasound," 14 Encyclopedia of Pharmaceutical Technology 103-122 (1996).

Mitragotri, S. et al., "Synergistic Effect of Low-frequency Ultrasound and Sodium Lauryl Sulfate on Transdermal Transport," J. Pharm. Sci. vol. 89, No. 7, pp. 892-900 (2000).

Mitragotri, "Synergistic Effect of Enhancers for Transdermal Drug Delivery," Pharm Res. vol. 17, No. 11, pp. 1354-1359 (2000).

Mitragotri and Joseph Kost, "Transdermal Delivery of Heparin and Low-Molecular Weight Heparin Using Low-Frequency Ultrasound," Pharmaceutical Research, vol. 18, No. 8, pp. 1151-1156 (Aug. 2001).

Miyazaki, et al., "Controlled Drug Release by Ultrasound Irradiation," Chemical & Pharmaceutical Bulletin, 33(1), pp. 428-431 (1985).

Monti et al., "Comparison of the effect of ultrasound of chemical enhancers on transdermal permeation of caffeine and morphine through hairless mouse skin in vitro," International J. Pharmaceuticals, vol. 229, Nos. 1-2, pp. 131-137 (Oct. 2001).

Morimoto et al., "Prediction of Skin Permeability of Drugs: Comparison of Human and Hairless Rat Skin," J. Pharm. Pharmacol. 44:634-639 (1991).

Murav'ev et al., "Mechanism of the Release of Pharmaceutical Substances from Ointment Bases by Ultrasound", Chemical Abstracts, vol. 84, No. 4, Jan. 26, 1976, p. 333, Abstract No. 22054g (Jan. 26, 1996).

Nagai et al., "Buccal/Gingival Drug Delivery Systems," Journal of Controlled Release 6:353-360 (1987).

Newman et al., "Hydrocortisone Phonophoresis," J. Am. Pod. Med. Assoc. 82:432-435 (1992).

Olanoff and Gibson, "Method to Enhance Intranasal Peptide Delivery," Controlled Release Technology Pharmaceutical Application 301-309 (1987).

Ongpipattanankul et al., "Evidence that Oleic Acid Exists in a Separate Phase Within Stratum Corneum Lipids," Pharm. Res. 8:350-354 (1991).

Otsuka, et al., "Use of Ultrasonic Waves in Pharmacy—I&II. Degradation of Polymers," Chemical Abstracts, vol. 69, No. 20, pp. 7513, Abstract No. 80161r & No. 80162 (Nov. 11, 1968).

"Pharmaceutical Sciences," Chapter 19—Disperse Systems pp. 267-272 Chapter 87—Medicated Applications pp. 1600-1606, 1614 Chapter 91—Sustained-Release Drug Delivery Systems pp. 1690-1693, Mack Publishing Co, Easton PA (1990).

Pishko et al., "Amperometric Glucose Microelectrodes Prepared through Immobilization of Glucose Oxidase in Redox Hydrogels," Anal. Chem. 63:2268-2272 (1991).

Potts and Guy, "Predicting Skin Permeability," Pharm. Res. 9:663-669 (1992).

Prausnitz et al., "Electroporation of mammalian skin: A mechanism to enhance transdermal drug delivery," 90 Proc. Natl. Acad. Sci. USA 10504-10508 (Nov. 15, 1993).

Quillen, "Phonophoresis: A Review of the Literature and Technique," Athletic Training 15:109-110 (1980).

Robinson & Lee, "Influence of Drug Properties on Design," Controlled Drug Delivery 42-43.

Rosell et al., "Skin Impedance from 1 Hz to 1 MHz," IEEE Trans. Biomed. Eng. 35:649-651 (1988).

Schreier & Bouwstra, "Liposomes and noisomes as topical drug carriers: dermal and transdermal drug delivery," 30 Journal of Controlled Release 1-15 (1994).

Skauen & Zentner, "Phonophoresis," Int. J. Pharm. 20, 235-245 (1984).

Stringfellow, "Clinical Applications of Interferons and Their Inducers," (Marcel Dekker ed., 2d ed. 1986).

Tamada et al., "Correlation of Blood Glucose With Iontophoretic Glucose Flux in Human Subjects for Glucose Monitoring," Proceed. Intern. Symp. Control. Rel. Bioact. Mater. 22, 129-130 (1995).

Tang, H. et al., "Theoretical description of transdermal transport of hydrophilic permeants: application to low-frequency sonophoresis," 90 J. Pharmaceutical Sciences 545-568 (Mar. 28, 2001).

Tezel et al., "Synergistic Effect of Low-Frequency Ultrasound and Surfactants on Skin Permeability," J. Pharmaceutical Sciences, vol. 91, No. 1, pp. 91-100 (Jan. 2002).

Tocanne et al., "Lipid lateral diffusion and membrane organization," FEBS Letters, vol. 257, pp. 10-16 (1989).

Tyle and Agrawala, "Drug Delivery by Phonophoresis," Pharm. Res. 6:355-361 (1989).

Veillard et al., "Buccal Controlled Delivery of Peptides," 14 Proceed. Intern. Symp. Control. Rel. Bioact. Mater 22 (Controlled Release Society, Inc. 1987).

Walker and Hadgraft, "Oleic Acid—a membrane 'fluidiser' or fluid within the membrane," Int. J. Pharm. 71:R1-R4 (1991).

Walmsley, "Applications of Ultrasound in Dentistry," Ultrasound in Med. and Biol. 14:7-14 (1988).

Walters, K.A., "Penetration Enhancers and Their Use in Transdermal Therapeutic Systems," Transdermal Drug Delivery: Developmental Issues and Research Initiatives, 197-246 (Hadgraft et al. eds. 1989).

Wester and Mailbach, "Animal Models for Percutaneous Absorption," Topical Drug Bioavailability Bioequivalence and Penetration 333-349 (1993).

Wheatley et al., "Use of Ussing Chamber for Investigation of Drug Delivery Across Viable Nasal Tissue Membranes," 14 Proceed. Intern. Symp. Rel. Bioact. Mater. 26-27 (Controlled Release Society, Inc. 1987).

Williams et al., "On the non-Gaussian distribution of human skin permeabilities," 86 Int. J. Pharm. 69-77 (1992).

Wilschut et al., "Estimating Skin Permeation. The Validation of Five Mathematical Skin Permeation Models," Chemosphere 30:1275-1296 (1995).

Chuang et al., Clinical Evaluation of a Continuous Minimally Invasive Glucose Flux Sensor Placed Over Ultrasonically Permeated Skin, Diabetes Tech & Therap., 2004, 6:21-30 (Abstract Only).

U.S. Patent and Trademark Office Action in U.S. Appl. No. 11/223,957, filed mailed Dec. 1, 2006.

U.S. Patent and Trademark Office Action in U.S. Appl. No. 11/223,971, filed mailed Apr. 2, 2009.

Extended European Search Report for European Application No. 05824881.6, mailed Jul. 7, 2011.

Official Notice of Rejection issued in Japanese Patent Application No. 2007-539116, mailed Jun. 28, 2011.

Comments to Official Rejection of Jun. 28, 2011 in Japanese Patent Application No. 2007-539116, dated Jul. 14, 2011.

Current Pending Claims in Japanese Patent Application No. 2007-539116, dated Jul. 14, 2011.

* cited by examiner

Fig. 24

| Subject number | Gender | Age | Diabetes Type | Duration | Insulin Pump | Disease Complications |
|---|---|---|---|---|---|---|
| 1 | Female | 34 | Type I | 15 years | no | None |
| 2 | Male | 46 | Type I | 40 years | no | Poor circulation and dehydration |
| 3 | Male | 33 | Type I | 20 years | yes | None |
| 4 | Female | 42 | Type I Brittle | 10 years | no | Ischemia, neuropathy, vascular disease which has an affect on her circulation |
| 5 | Male | 37 | Type 2 | 3 years | no | Poor insulin control, fasting glucose of 238, overweight |
| 6 | Female | 42 | Type 1 Brittle | 30 years | no | Loss of eye due to retinopathy, poor circulation, permanent disability |
| 7 | Male | 32 | Type 1 | 20 years | yes | Very athletic, problem with hypoglycemia |
| 8 | Male | 24 | Type 1 | 5 years | yes | None |
| 9 | Male | 19 | Type 1 | 5 years | yes | None |
| 10 | Male | 33 | Type 1 | 20 years | no | poor circulation and dehydration |
| 11 | Male | 43 | Type 2 | 5 years | no | Poor circulation and insulin control, dehydration, high fasting |
| 12 | Female | 39 | Type 2 | 5 years | no | Overweight, hypoglycemic tendencies |

EGA, individually optimized

SYSTEM AND METHOD FOR ANALYTE SAMPLING AND ANALYSIS WITH HYDROGEL

The present application is a divisional of U.S. application Ser. No. 11/201,334, filed Aug. 11, 2005, now abandoned, which is a continuation of U.S. application Ser. No. 10/974,963, filed Oct. 28, 2004, now abandoned, both of which are hereby incorporated by reference in their entireties. The present application is related to the following patent and applications, each of which is incorporated herein by reference it its entirety: U.S. application Ser. No. 09/979,096, filed Mar. 16, 2001; U.S. application Ser. No. 09/868,442, filed Dec. 17, 1999; U.S. Provisional Application No. 60/112,953, filed Dec. 18, 1998; U.S. Provisional Application No. 60/142,941, filed Jul. 12, 1999; U.S. Provisional Application No. 60/142,950, filed Jul. 12, 1999; U.S. Provisional Application No. 60/142,951, filed Jul. 12, 1999; U.S. Provisional Application No. 60/142,975, filed Jul. 12, 1999; U.S. Pat. No. 6,190,315; and U.S. Provisional Application No. 60/070,813, filed Jan. 8, 1998.

BACKGROUND OF THE INVENTION

1. Field of the Invention

The present invention relates to non-invasive sampling of body fluids, and, more particularly, to a system, method, and device for non-invasive body fluid sampling and analysis.

2. Description of the Related Art

Diabetics frequently prick their fingers and forearms to obtain blood in order to monitor their blood glucose concentration. This practice of using blood to perform frequent monitoring can be painful and inconvenient. New, less painful methods of sampling body fluids have been contemplated and disclosed. For example, these painless methods include the use of tiny needles,
the use of iontophoresis, and the use of ultrasound to sample body fluid, such as blood and interstitial fluid.

It has been shown that the application of ultrasound can enhance skin permeability. Examples of such are disclosed in U.S. Pat. No. 4,767,402, U.S. Pat. No. 5,947,921, and U.S. Pat. No. 6,002,961, the disclosures of which are incorporated, by reference, in their entireties. Ultrasound may be applied to the stratum corneum via a coupling medium in order to disrupt the lipid bilayers through the action of cavitation and its bioacoustic effects. The disruption of stratum corneum, a barrier to transport, allows the enhanced diffusion of analyte, such as glucose or drugs, through, into, and out of the skin.

Transport of analytes and body fluids can be enhanced further by the action of a motive force. These motive forces include, inter alia, sonophoretic, iontophoretic, electromotive, pressure force, vacuum, electromagnetic motive, thermal force, magnetic force, chemomotive, capillary action, and osmotic. The use of active forces provide a means for obtaining fluid for subsequent analysis.

The application of a motive force before, during, and after making the skin permeable has been disclosed in U.S. Pat. No. 5,279,543, U.S. Pat. No. 5,722,397, U.S. Pat. No. 5,947,921, U.S. Pat. No. 6,002,961, and U.S. Pat. No. 6,009,343, the disclosures of which are incorporated by reference in their entireties. The purpose of using a motive force is to actively extract body fluid and its content out of the skin for the purpose of analysis. As mentioned, active forces, such as vacuum, sonophoresis, and electrosmotic forces, can create convective flow through the stratum corneum. Although these forces can be used for extraction of body fluids, there are certain limitations that may apply when the forces are applied to human skin. For example, a major limitation is the flow and volume of body fluid that can be transported across the stratum corneum. In general, high-pressure force is necessary in order to transport fluid across an enhanced permeable area of stratum corneum. The application of vacuum on skin for an extended period may cause physical separation of the epidermis from the dermis, resulting in bruises and blisters.

Another example of a limitation is the amount of energy that can be applied to the skin in order to create convective flow. Extraction of usable volume of body fluid has the potential to cause pain and skin damage with prolonged exposure to ultrasound. In a similar manner, electro-osmotic extraction of body fluid through stratum corneum has the potential to cause skin damage due the need to use high current density. It is evident that there are limitations to the use of the mentioned extraction methods when applied to human skin.

SUMMARY OF THE INVENTION

Therefore, a need has arisen for a system, method, and device for noninvasive body fluid sampling and analysis that overcomes these and other drawbacks of the related art.

Therefore, a need has arisen for a method of enhancing the permeability of a biological membrane, such as skin, buccal, and nails, for an extended period of time, and a method for extracting body fluid to perform blood, interstitial fluid, lymph, or other body fluid analyte monitoring in a discrete or continuous manner that is noninvasive and practical.

According to one embodiment, the invention relates to a transdermal analyte monitoring system comprising a medium adapted to interface with a biological membrane and to receive an analyte from the biological membrane, wherein the medium comprises a hydrogel selected from the group consisting of vinyl acetate based hydrogels, agarose based hydrogels, polyethylene glycol diacrylate (PEG-DA) based hydrogels and mixtures thereof, and an electrode assembly, wherein the medium is adapted to react continuously with the analyte, and wherein an electrical signal is detected by the electrode assembly, and the electrical signal correlates to an analyte value.

According to another embodiment, the invention relates to a transdermal analyte monitoring system comprising a medium adapted to interface with a biological membrane and to receive an analyte from the biological membrane, and an electrode assembly comprising a plurality of electrodes, wherein a surface region of at least one of the electrode consists essentially of pure platinum, wherein the medium is adapted to react continuously with the analyte, and wherein an electrical signal is detected by the electrode assembly, and the electrical signal correlates to an analyte value.

According to another embodiment, the invention relates to a transdermal analyte monitoring system comprising a medium adapted to interface with a biological membrane and to receive an analyte from the biological membrane, an electrode assembly, and an interference filter located between the biological membrane and the electrode assembly for reducing interference from non-target biological moieties in the transdermal analyte monitoring system.

According to another embodiment, the invention relates to a transdermal analyte monitoring system comprising a medium adapted to interface with a biological membrane and to receive an analyte from the biological membrane, a sensor comprising an electrode assembly, the electrode assembly comprising a plurality of electrodes, and a processor programmed to implement an error correction method that corrects for sensor drift, wherein the medium is adapted to react continuously with the analyte, and wherein an electrical signal is detected by the electrode assembly, and the electrical signal correlates to an analyte value.

A method for non-invasive body fluid sampling and analysis is disclosed. According to one embodiment of the present invention, the method includes the steps of (1) identifying an area of biological membrane having a permeability level; (2) increasing the permeability level of the area of biological membrane; (3) contacting the area of biological membrane with a receiver; (4) extracting body fluid through and out of the area of biological membrane; (5) providing an external force to enhance the body fluid extraction; (6) collecting the body fluid in the receiver; (7) analyzing the collected body fluid for the presence of at least one analyte; and (8) providing the results of the step of analyzing the body fluid.

The area of biological membrane may be made permeable using ultrasound with controlled dosimetry. Extraction of body fluid may be performed on the area exposed to ultrasound using osmotic transport. The body fluid may be collected using a receiver. The receiver may be attached to the biological membrane in a form of a patch, a wearable reservoir, a membrane, an absorbent strip, a hydrogel, or an equivalent. The receiver may be analyzed for the presence of various analytes indicative of blood analytes. The analysis may comprise the use of electrochemical, biochemical, optical, fluorescence, absorbance, reflectance, Raman, magnetic, mass spectrometry, infra-red (IR) spectroscopy measurement methods and combinations thereof. The receiver may also be attached to a secondary receiver where the concentration of analyte in the secondary receiver is continuously maintained substantially lower than that in the body fluid so the chemical concentration driving force between body fluid and secondary receiver is maximized. This may be achieved by chemical reaction or volume for dilution or similar means. In one embodiment, the receiver and the secondary receiver may operate on different principles (e.g., osmosis, dilution, etc.). In another embodiment, the receivers may operate on the same principle.

A system for non-invasive body fluid sampling and analysis is disclosed. According to one embodiment of the present invention, the system includes a controller that controls the generation of ultrasound; an ultrasonic applicator that applies the ultrasound to an area of biological membrane; a receiver that contacts the area of biological membrane and receives body fluid through and out of the area of biological membrane; and a meter that interacts with the receiver and detects the presence of at least one analyte in the body fluid in the receiver. The receiver may include a membrane and a medium, such as a hydrogel, a fluid, or a liquid, that is contained within the membrane.

A method for noninvasive body fluid sampling and analysis is disclosed. According to one embodiment of the present invention, the method includes the steps of (1) enhancing a permeability level of an area of biological membrane; (2) attaching a receiver to the area of biological membrane; (3) extracting an analyte through and out of the area of biological membrane; (4) collecting the body fluid in the receiver; and (5) determining a concentration of at least one analyte in the body fluid.

A device for noninvasive body fluid sampling and analysis is disclosed. According to one embodiment of the present invention, the device includes a receiver that is attached to an area of biological membrane with an enhanced permeability and receives body fluid through and out of the area of biological membrane, and a wearable meter that detects the presence of at least one analyte in the received body fluid and indicates a concentration of that analyte. The receiver may include a membrane and a medium, such as a hydrogel, a fluid, or a liquid, that is contained in the membrane. The meter may include a processor and a device that detects the presence of the analyte. The detecting device may include an electrochemical detector; a biochemical detector; a fluorescence detector; an absorbance detector; a reflectance detector; a Raman detector; a magnetic detector; a mass spectrometry detector; an IR spectroscopy detector; and combinations thereof.

According to one embodiment of the present invention, osmotic forces may be used to sample body fluid from and through a biological membrane in an on-demand manner. The osmotic agent in solution, gel, hydrogel, or other form may be applied to the ultrasound-treated biological membrane using a receiver, such as a thin liquid reservoir, whenever the concentration of an analyte needs to be determined for diagnosis and monitoring. The receiver may be attached to the biological membrane using an adhesive. The receiver may be attached to the biological membrane for a brief duration. The solution in the receiver may be subsequently removed and analyzed for the presence of analytes. In one embodiment, the receiver may be constructed in the form of a patch. The receiver may contain a hydrogel and osmotic agent. The receiver may combine the osmotic agent and the chemical reagents to detect the presence of the analyte. The reagents may allow the use of electrochemical, biochemical, optical, fluorescence, absorbance, reflectance, Raman, magnetic, mass spectrometry, infrared (IR) spectroscopy measurement methods and combinations thereof to be performed on the receiver.

In another embodiment, osmotic forces may be used to sample body fluid from or through a biological membrane in a periodic or a continuous manner. The osmotic agent in solution form may be applied to the ultrasound-treated biological membrane using a thin receiver, such as a thin liquid reservoir, whenever the concentration of analyte needs to be determined for diagnosis and monitoring. The receiver may be attached to biological membrane using an adhesive. In one embodiment, the receiver may be constructed in the form of a patch. The receiver may contain a hydrogel that contains the osmotic agent. The receiver may contain means for manipulating the intensity and duration of the osmotic force. The intensity of the osmotic force may be manipulated using electric field forces, magnetic field forces, electromagnetic field forces, biochemical reactions, chemicals, molarity adjustment, adjusting solvents, adjusting pH, ultrasonic field forces, electro-omostic field forces, iontophoretic field forces, electroporatic field forces and combinations thereof. The duration of the osmotic force may be manipulated using electric field forces, magnetic field forces, electromagnetic field forces, biochemical reactions, chemicals, molarity adjustment, adjusting solvents, adjusting pH, ultrasonic field forces, electroomostic field forces, iontophoretic field forces, electroporatic field forces and combinations thereof. The receiver may combine the osmotic agent and the biochemical reagents to detect the presence of the analyte. The reagents may allow the use of electrochemical, biochemical, optical, fluorescence, absorbance, reflectance, Raman, magnetic, mass spectrometry, IR spectroscopy measurement methods and combinations thereof to be performed on the receiver. The receiver may also be removed periodically for detection.

In one embodiment, the intensity, duration, and frequency of exposure of biological membrane to osmotic forces may be manipulated by using an electric current to cause a change in the concentration of the osmotic agent that is in contact with the ultrasound-exposed biological membrane. The osmotic agent may be a multi-charged agent that can dissociate into several charged species. These charged species may be transported using electric field forces. A membrane may be used to isolate the charged species. The charged species freely diffuse and combine upon removal of the electric field force.

In one embodiment, the intensity, duration, and frequency of exposure of biological membrane to osmotic forces may be manipulated by using active forces to cause a change in the concentration of the osmotic agent that is in contact with the ultrasound-exposed biological membrane. The osmotic agent may be a neutral charge agent. The agent may be transported using a variety of field forces. The field force depends on the constitutive and colligative properties of the chosen agent. The field force generates a force necessary to move the osmotic agent toward and away from the biological membrane surface. The movement of the osmotic agent modulates the periodic and continuous extraction of body fluid through the stratum corneum.

In one embodiment, the intensity, duration, and frequency of exposure of biological membrane to osmotic forces may be manipulated by changing the concentration of the osmotic agent that is in contact with the ultrasound-exposed biological membrane. Manipulating the volume of the solvent and the volume of the hydrogel containing the osmotic agent may cause a change in the concentration of the osmotic agent. The volume of the hydrogel can be changed by constructing a hydrogel wherein its volume is sensitive to the concentrations of molecules that can diffuse into the gel. One example is a hydrogel constructed to be sensitive to the molecule glucose. The hydrogel volume can also be changed by manipulating its temperature and by changing the pH of the gel.

A receiver that is attached to an area of biological membrane with an enhanced permeability and receives body fluid through and out of the area of biological membrane is disclosed. According to one embodiment of the present invention, the receiver includes a first grid; a medium layer comprising at least one agent; a membrane that induces a concentration gradient barrier for the at least one agent; a counter grid; an oxidase layer; a detection layer; and a voltage source that provides a potential difference between the first grid and the counter grid. The body fluid, which may include blood, interstitial fluid, analyte, and lymph, may flow out of, or through, the biological membrane, to the detector layer via the first grid, the counter grid, and the oxidase layer.

It is a technical advantage of the present invention that a system, method, and device for non-invasive sampling and analysis of body fluids is disclosed. It is another technical advantage of the present invention that a concentration of an analyte may be measured continuously or periodically.

BRIEF DESCRIPTION OF THE DRAWINGS

For a more complete understanding of the present invention, the objects and advantages thereof, reference is now made to the following descriptions taken in connection with the accompanying drawings in which:

FIG. 24 shows patient data for participants in a clinical study;

DETAILED DESCRIPTION OF THE INVENTION

The preferred embodiments of the present invention and their advantages are best understood by referring to FIGS. 1 through 28 of the drawings, like numerals being used for like and corresponding parts of the various drawings.

As used herein, the term "body fluid" may include blood, interstitial fluid, lymph, and/or analyte. In addition, as used herein, the term "biological membrane" may include tissue, mucous membranes and cornified tissues, including skin, buccal, and nails. Further, as used herein, the term "force" may also include force gradients.

Although the present invention may be described in conjunction with human applications, veterinary applications are within the contemplation and the scope of the present invention.

Figure 1:
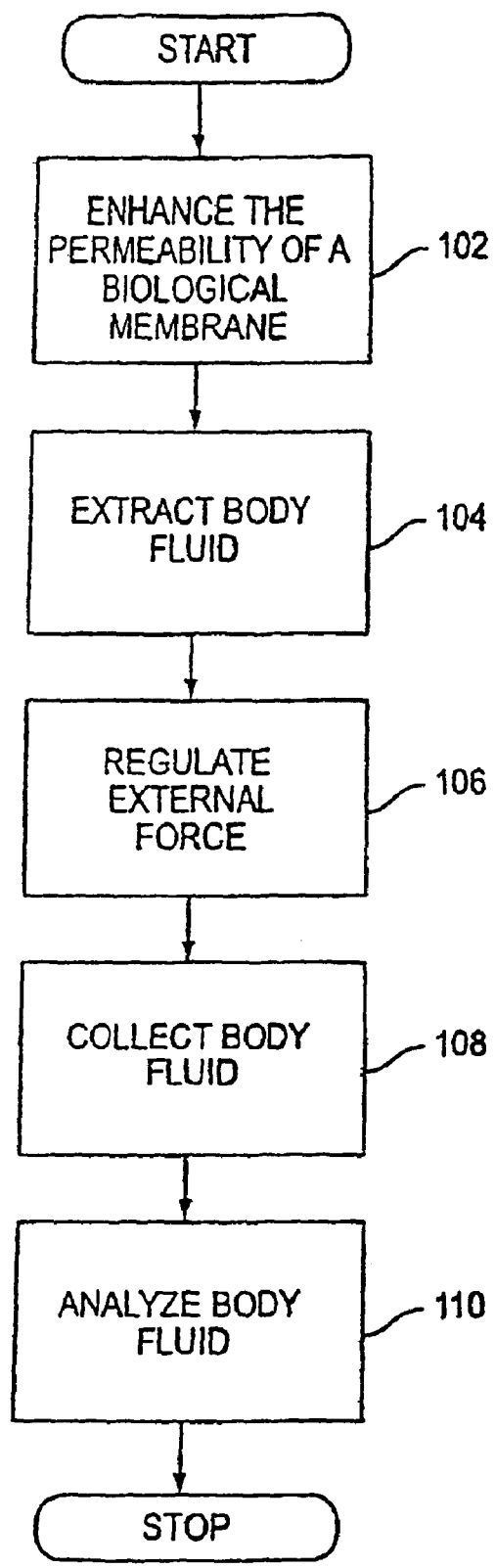
FIG. 1 is a flowchart depicting a method for non-invasive body fluid sampling according to one embodiment of the present invention.

Referring to FIG. 1, a flowchart depicting a method for non-invasive body fluid sampling and analysis according to one embodiment of the present invention is provided. In step 102, the permeability of an area of biological membrane is enhanced. In one embodiment, the area of biological membrane may be located on the volar forearm of a mammalian subject. In another embodiment, the area of biological membrane may be located on a thigh of a mammalian subject. In yet another embodiment, the area of biological membrane may be located on the abdomen. In still another embodiment, the area of biological membrane may be located on the back. Other body locations may also be used.

In general, several techniques may be used to enhance the permeability of the biological membrane, such as creating physical micropores, physically disrupting the lipid bilayers, chemically modifying the lipid bilayers, physically disrupting the stratum corneum, and chemically modifying the stratum corneum. The creation of micropores, or the disruption thereof, may be achieved by physical penetration using a needle, a microneedle, a silicon microneedle, a laser, a laser in combination with an absorbing dye, a heat source, an ultrasonic needle, an ultrasonic transducer, cryogenic ablation, RF ablation, photo-acoustic ablation, and combinations thereof.

In a preferred embodiment, ultrasound may be applied to the area of biological membrane to enhance its permeability. Ultrasound is generally defined as sound at a frequency of greater than about 20 kHz. Therapeutic ultrasound is typically between 20 kHz and 5 MHz. Near ultrasound is typically about 10 kHz to about 20 kHz. It should be understood that in addition to ultrasound, near ultrasound may be used in embodiments of the present invention.

In general, ultrasound, or near ultrasound, is preferably applied to the area of biological membrane at a frequency sufficient to cause cavitation and increase the permeability of the biological membrane. In one embodiment, ultrasound may be applied at a frequency of from about 10 kHz to about 500 kHz. In another embodiment, ultrasound may be applied at a frequency of from about 20 kHz to about 150 kHz. In yet another embodiment, the ultrasound may be applied at 50 kHz. Other frequencies of ultrasound may be applied to enhance the permeability level of the biological membrane.

In one embodiment, the ultrasound may have an intensity in the range of about 0 to about 100 watt/cm$^2$, and preferably in the range of 0 to about 20 watt/cm$^2$. Other appropriate intensities may be used as desired.

Techniques for increasing the permeability of a biological membrane are disclosed in U.S. Pat. No. 6,190,315 to Kost et al., the disclosure of which is hereby incorporated by reference in its entirety.

In step 104, body fluid is extracted through or out of the area of biological membrane. In one embodiment, an external force, such as an osmotic force, may assist in the extraction. In one embodiment, the osmotic force may be controlled before, during, and after the permeability of the biological membrane is enhanced.

In one embodiment, the osmotic force may be generated by the application of an osmotic agent to the area of biological membrane. The osmotic agent may be in the form of an element, a molecule, a macromolecule, a chemical compound, or combinations thereof. The osmotic agent may also be combined with a liquid solution, a hydrogel, a gel, or an agent having a similar function.

In step 106, the magnitude, intensity, and duration of the external force may be regulated by at least one additional first energy and/or force. In one embodiment, the first additional energy and/or force may be applied to control and regulate the movement and function of the osmotic agent for extraction of body fluid through and out of the biological membrane. The first additional energy and/or force may be provided in the form of heat, a temperature force, a pressure force, an electromotive force, a mechanical agitation, ultrasound, iontophoresis, an electromagnetic force, a magnetic force, a photothermal force, a photoacoustic force, and combinations thereof. The effect of an electric field and ultrasound on transdermal drug delivery is disclosed in U.S. Pat. No. 6,041,253, the disclosure of which is incorporated, by reference, in its entirety.

In one embodiment, if the first additional energy and/or force is provided by ultrasound, the frequency of the ultrasound may be provided at a different frequency than the frequency used to enhance the permeability of the biological membrane. In one embodiment, the frequency of the first additional energy/force ultrasound may be higher than the frequency of the permeability enhancing ultrasound.

In step 108, the body fluid may be collected in a receiver. In one embodiment, the receiver may be contacted with the biological membrane in a form of a patch, a wearable reservoir, a membrane, an absorbent strip, a hydrogel, or a structure that performs an equivalent function. Other types and configurations of receivers may be used.

In one embodiment, the receiver may be provided with a secondary receiver having an analyte concentration that is continuously maintained to be substantially lower than the analyte concentration in the body fluid, so the chemical concentration driving force between body fluid and secondary receiver is maximized. This may be achieved by chemical reaction or volume for dilution or similar means.

In one embodiment, a second external energy/force may be applied between the first receiver and the secondary receiver. In one embodiment, the second external energy/force may be different (e.g., a different type of external force) from the first external energy/force. In another embodiment, the second external energy/force may be the same (e.g., the same type of external force) as the first external energy/force. The first and second external energy/force may vary in type, duration, and intensity, and may be controlled through different additional energy and/or forces.

In step 110, the collected body fluid may be analyzed. In one embodiment, the analysis may include the use of appropriate methods, such as electrochemical, biochemical, optical, fluorescence, absorbance, reflectance, Raman, magnetic, mass spectrometry, infra-red (IR) spectroscopy measurement, and combinations thereof.

In one embodiment, multiple analytes may be analyzed simultaneously, in parallel, or in series. The results from these multiple analyses may be used in combination with algorithms, for example, to increase the accuracy, or precision, or both, of the analysis and measurements.

In one embodiment, the receiver may be removed from contact with the biological membrane in order to analyze the collected body fluid. In another embodiment, the receiver may remain in contact with the biological membrane as the collected body fluid is analyzed.

Figure 2:
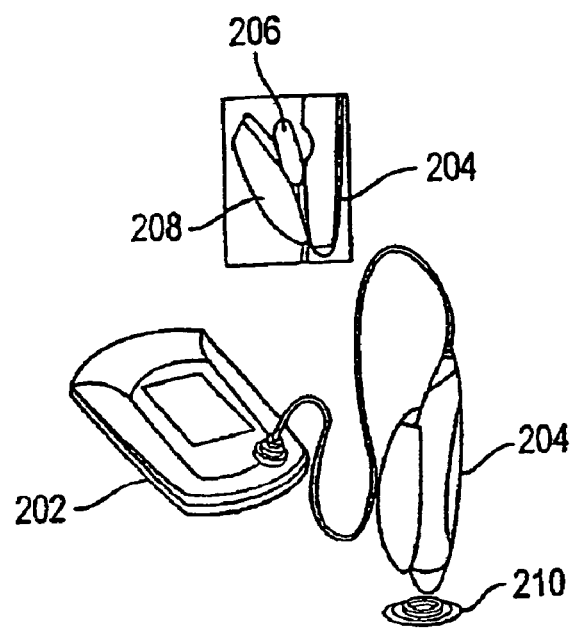
FIG. 2 depicts a device for controlled application of ultrasound to a biological membrane to enhance the permeability of the biological membrane according to one embodiment of the present invention.

Referring to FIG. 2, a device for the controlled application of ultrasound to biological membrane to enhance the permeability of a biological membrane according to one embodiment of the present invention is shown. Device 200 includes controller 202, which interfaces with ultrasound applicator 204 by any suitable means, such as a cable. Controller 202 controls the application of ultrasound to the area of biological membrane. In one embodiment, ultrasound or near ultrasound having an intensity in the range of about 0 to about 20 watt/cm$^2$ may be generated by controller 202 and ultrasound applicator 204. In one embodiment, the ultrasound may have a frequency of about 20 kHz to about 150 kHz. In another embodiment, the ultrasound may have a frequency of 50 kHz. Other ultrasound frequencies may also be used.

In addition, controller 202 may include a display, such as a LCD or a LED display, in order to convey information to the user as required. Controller 202 may also include a user interface as is known in the art.

Ultrasound applicator 204 may be provided with cartridge 206, which contains ultrasound coupling solution 208. Cartridge 206 may be made of any material, such as plastic, that may encapsulate ultrasound coupling solution 208. Suitable ultrasound coupling solutions 208 include, but are not limited to, water, saline, alcohols including ethanol and isopropanol (in a concentration range of 10 to 100% in aqueous solution), surfactants such as Triton X-100, SLS, or SDS (preferably in a concentration range of between 0.001 and 10% in aqueous solution), DMSO (preferably in a concentration range of between 10 and 100% in aqueous solution), fatty acids such as linoleic acid (preferably in a concentration range of between 0.1 and 2% in ethanol-water (50:50) mixture), azone (preferably in a concentration range of between 0.1 and 10% in ethanol-water (50:50) mixture), polyethylene glycol in a concentration range of preferably between 0.1 and 50% in aqueous solution, histamine in a concentration range of preferably between 0.1 and 100 mg/ml in aqueous solution, EDTA in a concentration range of preferably between one and 100 mM, sodium hydroxide in a concentration range of preferably between one and 100 mM, sodium octyl sulfate, N-taurosylsarcosine, octyltrimethyl ammoniumbromide, dodecyltrimethyl ammoniumbromide, tetradecyltrimethyl ammoniumbromide, hexadecyltrimethyl ammoniumbromide, dodecylpyridinium chloride hydrate, SPAN 20, BRIJ 30, glycolic acid ethoxylate 4-ter-butyl phenyl ether, IGEPAL CO-210, and combinations thereof.

In one embodiment, the coupling medium may also include a chemical enhancer. Transport enhancement may be obtained by adding capillary permeability enhancers, for example, histamine, to the coupling medium. The concentration of histamine in the coupling medium may be in the range of between 0.1 and 100 mg/ml. These agents may be delivered across the biological membrane during application of ultrasound and may cause local edema that increases local fluid pressure and may enhance transport of analytes across the biological membrane. In addition, the occurrence of free fluid due to edema may induce cavitation locally so as to enhance transport of analytes across the biological membrane.

In one embodiment, cartridge 206 may be pierced when inserted into ultrasound applicator 204, and ultrasound coupling solution 208 may be transferred to a chamber (not shown).

A target identifying device, such as target ring 210, may be attached to the area of biological membrane that will have its permeability increased. Target ring 210 may be attached to the area of biological membrane by a transdermal adhesive (not shown). In one embodiment, target ring 210 may have the transdermal adhesive pre-applied, and may be disposed after each use. In another embodiment, target ring 210 may be reusable.

Target ring 210 may be made of any suitable material, including plastic, ceramic, rubber, foam, etc. In general, target ring 210 identifies the area of biological membrane for permeability enhancement and body fluid extraction. In one embodiment, target ring 210 may be used to hold receiver 214 in contact with the biological membrane after the permeability of the biological membrane has been increased.

In one embodiment, target ring 210 may be used to monitor the permeability level of the biological membrane, as disclosed in PCT International Patent Appl'n Ser. No. PCT/US99/30067, entitled "Method and Apparatus for Enhancement of Transdermal Transport," the disclosure of which is incorporated by reference in its entirety. In such an embodiment, target ring 210 may interface with ultrasound applicator 204.

Ultrasound applicator 204 may be applied to target ring 210 and activated to expose ultrasound coupling solution 208 to the biological membrane. Controller 202 controls ultrasound applicator 204 to transmit ultrasound through ultrasound coupling solution 208. During ultrasound exposure, controller 202 may monitor changes in biological membrane permeability, and may display this information to the user.

Controller 202 may cease, or discontinue, the application of ultrasound once a predetermined level of biological membrane permeability is reached. This level of permeability may be preprogrammed, or it may be determined in real-time as the ultrasound is applied. The predetermined level of permeability may be programmed for each individual due to biological membrane differences among individuals.

After the predetermined level of permeability is reached, ultrasound coupling solution 208 may be vacuated from chamber (not shown) into cartridge 206, which may then be discarded. In another embodiment, ultrasound coupling solution 208 may be vacuated into a holding area (not shown) in ultrasound applicator 204, and later discharged. Ultrasound applicator 204 may then be removed from target ring 210.

Figure 3:
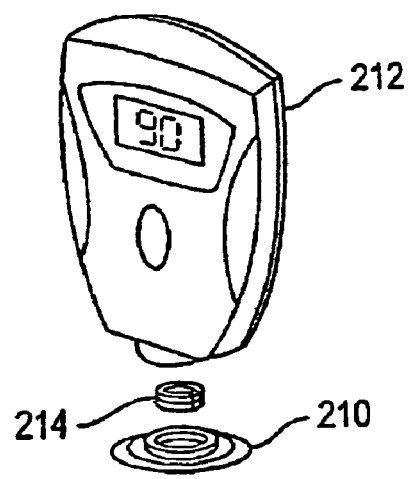
FIG. 3 depicts the components to perform discrete extraction and measurement of body fluid to infer analyte concentrations according to one embodiment of the present invention.

Referring to FIG. 3, an device for the analysis of body fluid according to one embodiment of the present invention is provided. Receiver 214 may be placed into target ring 210 to perform a discrete, or on-demand, extraction of body fluid through and/or out of the biological membrane. Receiver 214 may contain a medium, such as a hydrogel layer, that incorporates an osmotic agent. In one embodiment, the hydrogel may be formulated to contain phosphate buffered saline (PBS), with the saline being sodium chloride having a concentration range of about 0.01 M to about 10 M. The hydrogel may be buffered at pH 7. Other osmotic agents may also be used in place of, or in addition to, sodium chloride. Preferably, these osmotic agents are non-irritating, non-staining, and non-immunogenic. Examples of such osmotic agents include, inter alia, lactate and magnesium sulfate.

In another embodiment, receiver 214 may include a fluid or liquid medium, such as water or a buffer, that is contained within a semi-permeable membrane. Receiver 214 may also include a spongy material, such as foam.

Receiver 214 may be applied to the biological membrane to contact the ultrasound exposed biological membrane. In one embodiment, receiver 214 may be applied to the biological membrane for a time period sufficient to collect an amount of body fluid sufficient for detection. In another embodiment, receiver 214 may be applied to the biological membrane for a sufficient time period to collect a predetermined amount of body fluid. In yet another embodiment, receiver 214 may be applied to the biological membrane for a predetermined time. In one embodiment, the contact between receiver 214 and the biological membrane may last for 15 minutes or less. In another embodiment, the contact between receiver 214 and the biological membrane may last for 5 minutes or less. In still another embodiment, the contact between receiver 214 and the biological membrane may last for 2 minutes or less. The actual duration of contact may depend on the sensitivity of the detection method used for analysis.

In one embodiment, the medium of receiver 214 may contain at least one reagent (not shown) in order to detect the presence of certain analytes in the body fluid that has been extracted from or through the biological membrane. In one embodiment, the hydrogel layer of receiver 214 may contain the reagents, and the reagents may be attached to the hydrogel by ionic and/or covalent means, or may be immobilized by gel entrapment. The reagents may also be arranged as an adjacent layer to the hydrogel wherein the analyte from the body fluid that has been extracted into the hydrogel can diffuse into and react to generate by-products. The by-products may then be detected using electrochemical, biochemical, optical, fluorescence, absorbance, reflectance, Raman, magnetic, mass spectrometry, IR spectroscopy measurement methods and combinations thereof.

The detection methods may be performed by meter 212. Meter 212 may include a processor (not shown) and a display, such as an LCD display. Other suitable displays may be provided.

In one embodiment, meter 212 may provide an interface that allows information be downloaded to an external device, such as a computer. Such an interface may allow the connection of interface cables, or it may be a wireless interface.

Meter 212 may be configured to determine body fluid glucose concentration by incorporating glucose oxidase in the medium of receiver 214. In one embodiment, glucose from extracted body fluid may react with glucose oxidase to generate hydrogen peroxide. Hydrogen peroxide may be detected by the oxidation of hydrogen peroxide at the surface of electrodes incorporated into receiver 214. The oxidation of hydrogen peroxide transfers electrons onto the electrode surface which generates a current flow that can be quantified using a potentiostat, which may be incorporated into meter 212. A glucose concentration proportional to the concentration of hydrogen peroxide may be calculated, and the result may be reported to the user via a display. Various configurations of electrodes and reagents, known to those of ordinary skill in the art, may be incorporated to perform detection and analysis of glucose and other analytes.

Meter 212 may also be configured to simultaneously measure the concentration of an analyte, such as glucose, where the body fluid concentration is expected to fluctuate, and an analyte, like creatinine or calcium, where the body fluid concentration is expected to remain relatively stable over minutes, hours, or days. An analyte concentration, which may be determined by an algorithm that takes into account the relative concentrations of the fluctuating and the more stable analyte, may be reported to the user via a display.

In another embodiment, meter 212 may analyze multiple analytes simultaneously, in parallel, or in series. The results from these multiple analyses may be used in combination with algorithms, for example, to increase the accuracy, or precision, or both, of the analysis and measurements.

Receiver 214 may be discarded after the extraction and measurement steps. In another embodiment, receiver 214 may be reused. In one embodiment, receiver 214 may be cleaned, sanitized, etc. before it may be reused. Various configurations of electrodes and reagents, known to those of ordinary skill in the art, may be incorporated to perform detection and analysis of glucose and other analytes.

Figure 4:
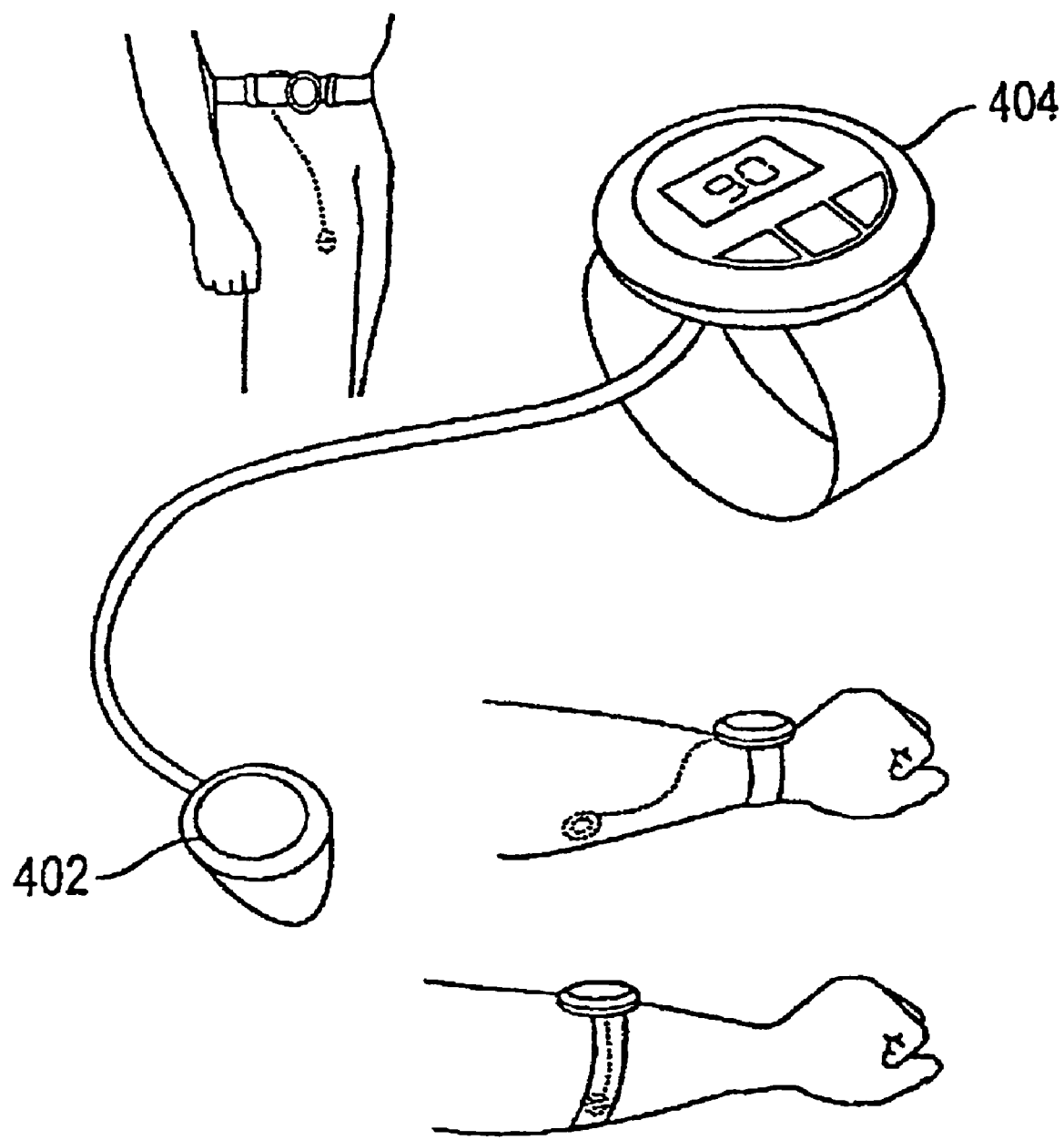
FIG. 4 depicts the components to perform continuous extraction and measurement of body fluid to infer analyte concentrations according to one embodiment of the present invention.

Referring to FIG. 4, a device for the continuous extraction and analysis of body fluid to infer analyte concentrations according to another embodiment of the present invention is provided. As shown in the figure, a biological membrane site on the forearm, the abdomen, or thigh may be exposed to ultrasound; other biological membrane sites, such as those on the back, may also be used. Receiver 402, which may be similar to receiver 214, may contact the ultrasound exposed biological membrane site to perform continuous extraction of body fluid. In one embodiment, receiver 402 may contain a medium, such as a hydrogel layer, that may incorporate an osmotic agent, such as sodium chloride. The hydrogel is formulated to contain phosphate buffered saline (PBS), with the saline being sodium chloride in the concentration range of 0.01 M to 10 M. The hydrogel may be buffered at pH 7.

Other osmotic agents may also be used in place of, or in addition to, sodium chloride. These osmotic agents are preferably non-irritating, non-staining, and non-immunogenic. Examples of these other osmotic agents may include, inter alia, lactate and magnesium sulfate. Receiver 402 may be applied to contact the ultrasound exposed biological membrane. In one embodiment, the duration of this contact may be 12-24 hours, or more. In another embodiment, other durations of contact, including substantially shorter durations, and substantially longer durations, may be used as desired.

In another embodiment, receiver 402 may include a fluid or liquid medium, such as water or a buffer, that is contained within a semi-permeable membrane. Receiver 402 may also include a spongy material, such as foam.

In one embodiment, the medium of receiver 402 may contain at least one reagent (not shown) that detects the presence of analytes in the body fluid that has been extracted thorough and out of the biological membrane. In one embodiment, the hydrogel layer of receiver 402 may contain reagents that may be attached by ionic and covalent means to the hydrogel, or may be immobilized by gel entrapment. The reagents may also be arranged as an adjacent layer to the hydrogel wherein the analyte from the body fluid that has been extracted into the hydrogel may diffuse into and react to generate by-products. The by-products may be detected using electrochemical, biochemical, optical, fluorescence, absorbance, reflectance, Raman, magnetic, mass spectrometry, IR spectroscopy measurement methods and combinations thereof.

The detection methods and results may be performed and presented to the user by meter 404, which may be similar in function to meter 212, discussed above. In one embodiment, meter 404 may be wearable. For example, as depicted in the figure, meter 404 may be worn in a manner similar to the way a wristwatch is worn. Meter 404 may also be worn on a belt, in a pocket, etc.

Meter 404 may incorporate power and electronics to control the periodic extraction of body fluid, to detect analyte, and to present the analyte concentration in a continuous manner. Meter 404 may contain electronics and software for the acquisition of sensor signals, and may perform signal processing, and may store analysis and trending information.

In one embodiment, meter 404 may provide an interface that allows information be downloaded to an external device, such as a computer. Such an interface may allow the connection of interface cables, or it may be a wireless interface.

Meter 404 may be configured to determine body fluid glucose concentration by incorporating glucose oxidase in the medium. In one embodiment, glucose from extracted body fluid may react with glucose oxidase to generate hydrogen peroxide. Hydrogen peroxide may be detected by the oxidation of hydrogen peroxide at the surface of electrodes incorporated into receiver 402. The oxidation of hydrogen peroxide transfers electrons onto the electrode surface which generates a current flow that can be quantified using a potentiostat, which may be incorporated into meter 404. A glucose concentration proportional to the concentration of hydrogen peroxide may be calculated and the result may be reported to the user via a display. Various configurations of electrodes and reagents, known to those of ordinary skill in the art, may be incorporated to perform detection and analysis of glucose and other analytes.

In one embodiment, meter 404 may also be configured to simultaneously measure concentration of an analyte, such as glucose, where the body fluid concentration is expected to fluctuate, and an analyte, like creatinine or calcium, where the body fluid concentration is expected to remain relatively stable over minutes, hours, or days. An analyte concentration, which may be determined by an algorithm that takes into account the relative concentrations of the fluctuating and the more stable analyte, may be reported to the user via a display.

In another embodiment, meter 404 may analyze multiple analytes simultaneously, in parallel, or in series. The results from these multiple analyses may be used in combination with algorithms, for example, to increase the accuracy, or precision, or both, of the analysis and measurements.

In another embodiment, receiver 402 may be removed from contact with the biological membrane for analysis by meter 404. Receiver 402 may be put in contact with the biological membrane after such analysis.

Meter 404 may provide analyte readings to the user in a periodic or a continuous manner. For example, in one embodiment, in continuous monitoring of the analyte glucose, glucose concentration may be displayed to the user every 30 minutes, more preferably every 15 minutes, most preferable every 5 minutes, or even more frequently. In another embodiment, the glucose concentration may be displayed continuously. The period may depend on the sensitivity and method of analyte detection. In continuous glucose monitoring, in one embodiment, glucose detection may be performed by an electrochemical method using electrodes and reagents incorporated into receiver 402 and detection and analysis performed by meter 404. During the measurement period, osmotic extraction of body fluid may be performed continuously by the hydrogel layer of receiver 402. Body fluid may accumulate in the hydrogel of receiver 402. Glucose in body fluid diffuses to react with glucose oxidase and is converted into hydrogen peroxide. The hydrogen peroxide is consumed by poising the working electrode with respect to a reference electrode. During the resting period, hydrogen peroxide accumulates and is consumed or destroyed before the measuring period. The magnitude of the working potential can be applied to rapidly consume the build up of hydrogen peroxide.

Figure 5:
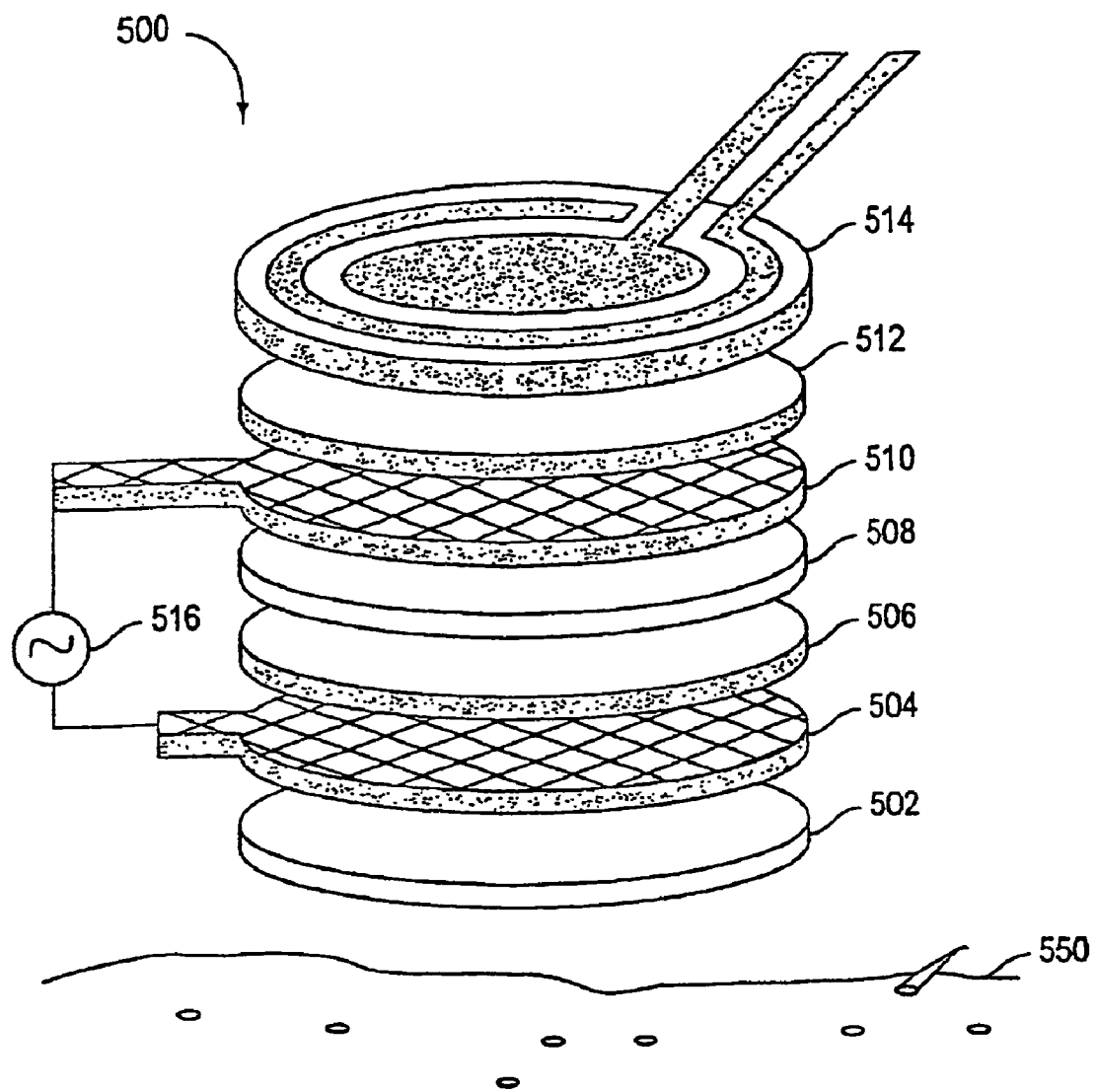
FIG. 5 depicts an approach to periodic monitoring of an analyte by performing periodic osmotic extractions of body fluid according to one embodiment of the present invention.

Referring to FIG. 5, an approach to periodic monitoring of an analyte by performing periodic osmotic extractions of body fluid according to another embodiment of the present invention is shown. The osmotic extraction intensity and frequency may be manipulated by using an osmotic agent that dissociates into multiple charged species, and an electrical potential may be used to move the concentration of charges toward and away from biological membrane surface 550. Receiver 500 may include grid, mesh, or screen 504; medium 506, which may be a hydrogel layer; membrane 508; counter grid, mesh, or screen 510; oxidase layer 512; and detection layer 514. Grid 504 and counter grid 510 may be connected to voltage source 516. Membrane 508 may be a semi-permeable membrane that is used to induce a concentration gradient barrier for the osmotic agent contained in medium 506. The preferable osmotic agent may contain negative and positive species or counter ions. Manipulating the concentration of charged species at the boundary adjacent to the stratum corneum of the ultrasound-exposed biological membrane may provide periodic extraction of body fluid.

In one embodiment, receiver 500 may make contact with the skin though contact medium 502, which may be a hydrogel, or other suitable medium.

The concentration of the charged species may be manipulated by applying a potential difference between grid 504 and counter grid 510 using voltage source 516. In one embodiment, the potential difference may be of a magnitude that is sufficient to manipulate the osmotic agent. The polarity of the grid may also be changed to transport charges toward and away from biological membrane surface 550. Grid 504 and counter grid 510 may be configured with optimum porosity as to allow body fluid and/or analyte to travel out of stratum corneum, through grid 504, through grid 510, and into oxidase layer 512, and ultimately to detection layer 514. Oxidase layer 512 may be used with an appropriate catalyst, or enzyme, to confer specificity of analyte detection. Detection layer 514 may include working and reference electrodes (not shown) that allow for the detection of the by-products of oxidase layer 512 to quantify the concentration of the desired analyte of detection.

Example 1

The following example does not limit the present invention in any way, and is intended to illustrate an embodiment of the present invention.

The following is a description of experiments which implemented painless extraction, collection, and analysis of body fluid to determine body fluid glucose concentration in a human using a hyperosmotic extraction fluid and comparing this condition with iso-osmotic extraction fluid, in accordance with one embodiment of the present invention. Although body fluid glucose concentration serves as an example to demonstrate feasibility, other analytes are within the contemplation of the present invention. In addition, multiple analytes may be measured and/or analyzed simultaneously, in parallel, or in series, and results from these multiple measurements may be used in combination with algorithms, for example, to increase the accuracy or precision or both of measurements. As may be recognized by one of ordinary skill in the art, these steps may be automated and implemented with the device described above.

Four sites on the volar forearm of a human volunteer were treated with ultrasound using the device described in FIG. 2. The ultrasound transducer and its housing were placed on the volar forearm of the volunteer with enough pressure to produce a good contact between the skin and the outer transducer housing, and to prevent leaking. The area surrounding the transducer was then filled with a coupling medium of sodium dodecyl sulfate and silica particles in phosphate-buffered saline (PBS). Ultrasound was briefly applied (5-30 s), the transducer apparatus was removed from the biological membrane, and the skin was rinsed with tap water and dried.

Figure 6:
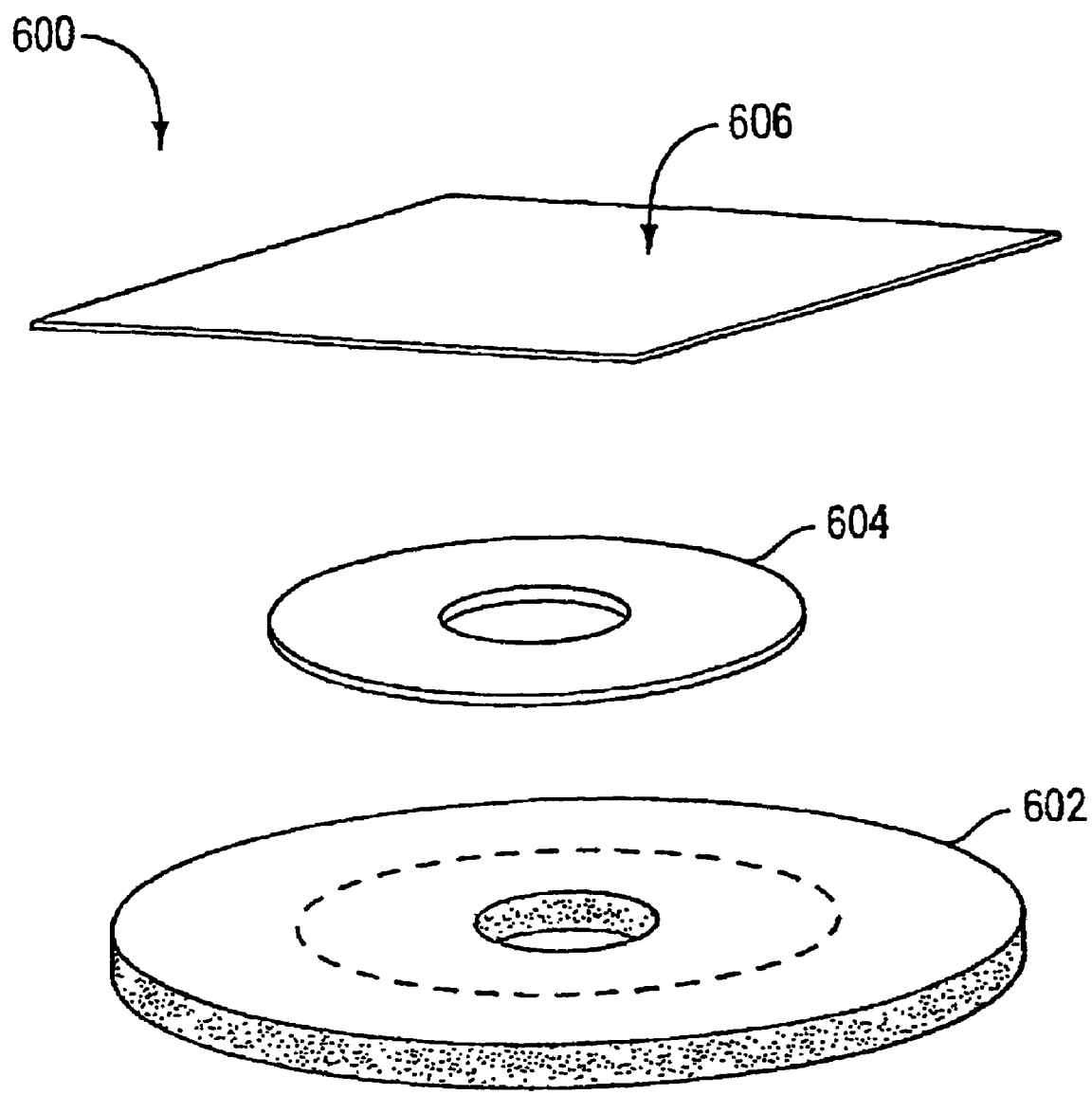
FIG. 6 depicts the components of a wearable extraction chamber according to one embodiment of the present invention.

FIG. 6 describes the components of wearable extraction chamber 600. Four extraction chambers were placed on each sonicated site of the human volunteer. Thin circular foam chamber 602 was constructed using foam MED 5636 Avery Dennison (7/16" ID×1 1/8" OD). Foam chambers 602 were attached concentrically to the sonicated biological membrane sites using double-sided adhesive (Adhesive Arcade 8570, 7/16" ID×7/8" OD) attached to one side of element 602. The other side of foam chamber 602 was attached concentrically to double-sided adhesive 604 (Adhesive Arcade 8570, 7/16" ID×7/8" OD). Thin transparent lid 606 was made of 3M Polyester 1012 (1 1/8"×1 1/8"). Double-sided adhesive 604 permitted thin transparent lid 606 to be attached to foam chamber 602 after placement of liquid into the inner diameter of foam chamber 602 when attached to biological membrane. Thin transparent lid 606 acted as a lid to prevent liquid from leaking out of the extraction chamber, and to allow the extraction chambers to be wearable for an extended period of time.

Each extraction chamber was alternately filled with 100 µl of extraction solution for 15 min and 100 µl hydration solution for 10-40 min. Extraction solution was PBS; on two sites the PBS contained additional NaCl to bring the total concentration of NaCl to 1 M. Hydration solution was PBS for all sites.

Figure 7:
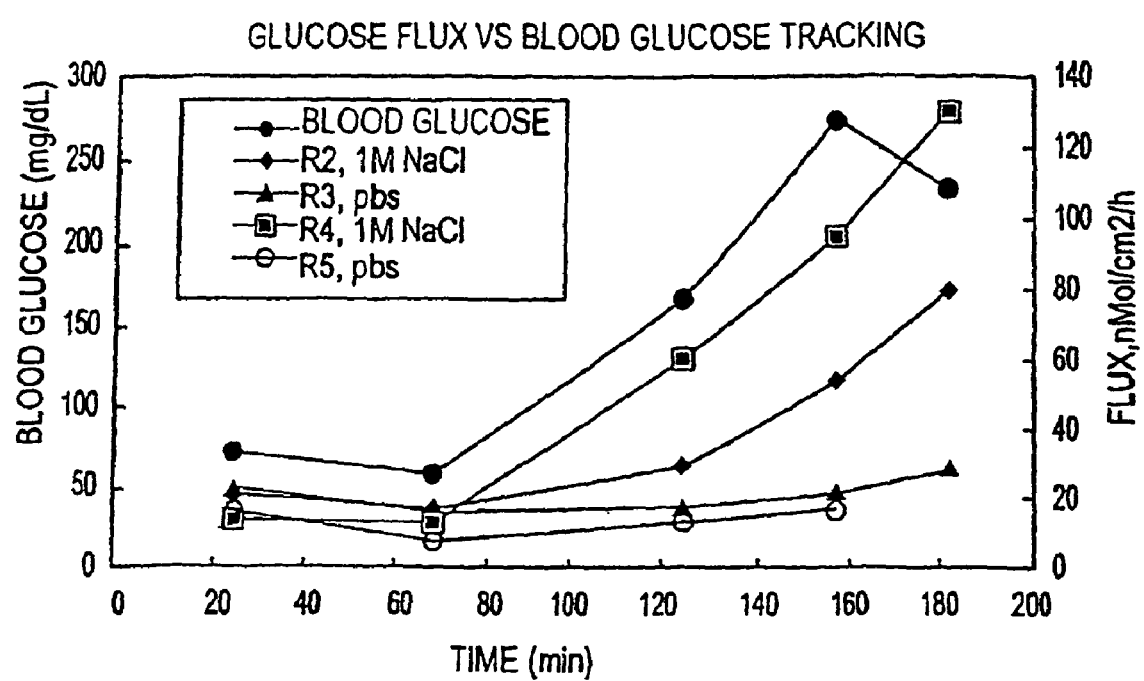
FIG. 7 depicts a graph of glucose flux versus blood glucose concentration according to one embodiment of the present invention.

Solutions were collected and analyzed for glucose concentration using high-pressure liquid chromatography. The results of the HPLC concentration were normalized for the injection amount and the total solution volume, and were reported as glucose flux ($Q_g$), the mass of glucose that crossed the sonicated site per unit time per unit area. Body fluid glucose concentrations ($C_{bg}$) were obtained by testing capillary blood obtained from a lanced finger in a Bayer Glucometer Elite meter. It was hypothesized that $Q_g$ would be linearly proportional to $C_{bg}$. FIG. 7 shows a graph of $Q_g$ versus $C_{bg}$. Unexpectedly, $Q_g$ from the sonicated sites exposed to 1 M NaCl correlated to $C_{bg}$ much more strongly than $Q_g$ from the sonicated sites exposed to 0.15 M NaCl.

According to another aspect of the present invention, an apparatus and method for regulating the degree of skin permeabilization through a feedback system is provided. This apparatus and method may be similar to what has been described above, with the addition of further regulation of the degree of skin permeabilization. Feedback control as a method of monitoring the degree of skin permeability is described in more detail in U.S. application Ser. No. 09/868,442, entitled "Methods and Apparatus for Enhancement of Transdermal Transport," which is hereby incorporated by reference in its entirety. In this embodiment, the application of the skin permeabilizing device is terminated when desired values of parameters describing skin conductance are achieved. As the discussion proceeds with regard to FIG. 8, it should be noted that the descriptions above may be relevant to this description.

Figure 8:
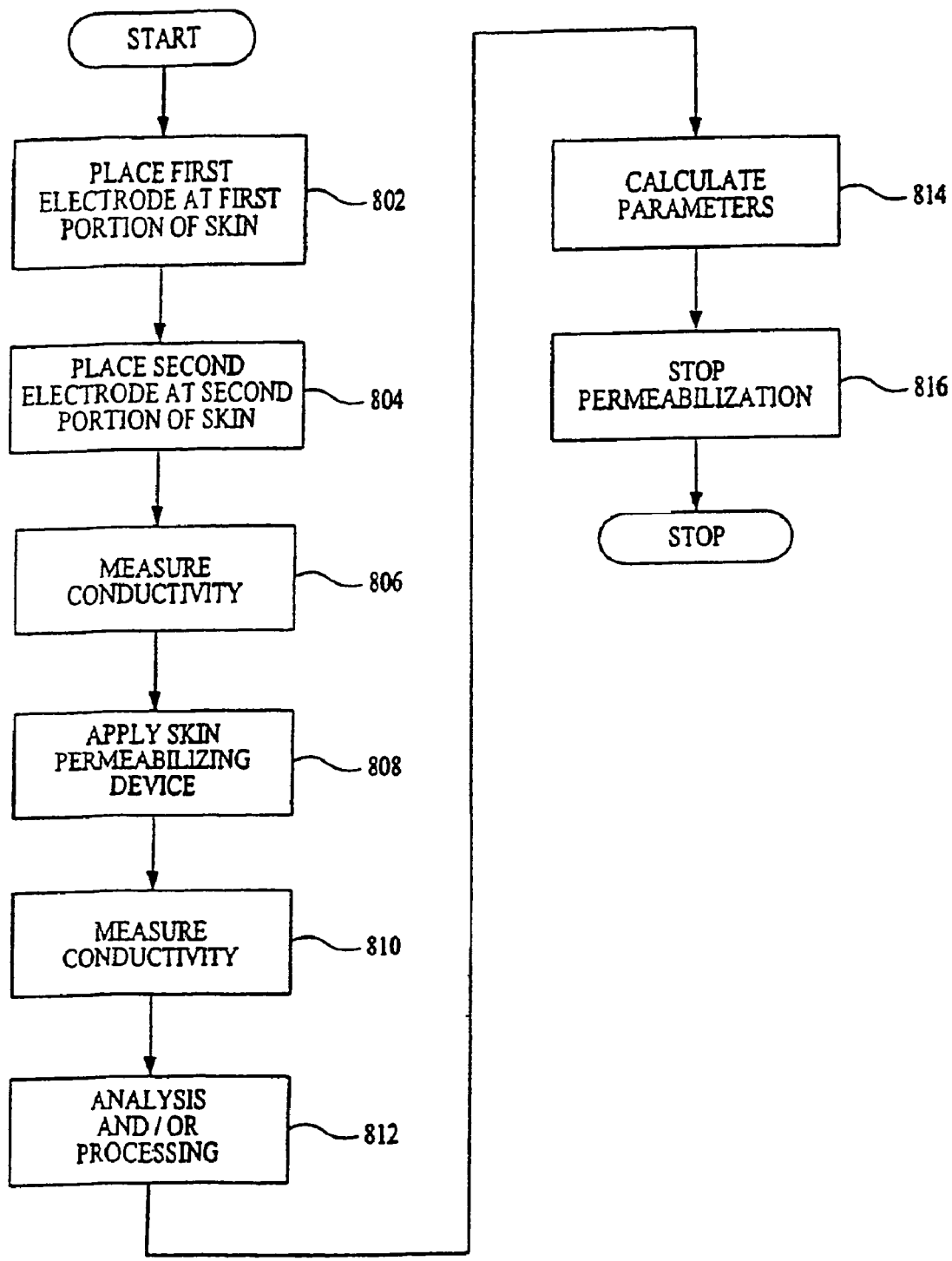
FIG. 8 depicts a flow chart of a method for controlled enhancement of transdermal delivery according to one embodiment of the present invention.

Referring to FIG. 8, a flowchart of the method is provided. In step 802, a first, or source, electrode is coupled in electrical contact with a first area of skin where permeabilization is required. The source electrode does not have to make direct contact with the skin. Rather, it may be electrically coupled to the skin through the medium that is being used to transmit ultrasound. In one embodiment, where an ultrasound-producing device is used as the skin permeabilizing device, the ultrasonic transducer and horn that will be used to apply the ultrasound doubles as the source electrode through which electrical parameters of the first area of skin may be measured and is coupled to the skin through a saline solution used as an ultrasound medium. In another embodiment, a separate electrode is affixed to the first area of skin and is used as the source electrode. In still another embodiment, the housing of the device used to apply ultrasound to the first area of skin is used as the source electrode. The source electrode can be made of any suitable conducting material including, for example, metals and conducting polymers.

Next, in step 804, a second, or counter, electrode is coupled in electrical contact with a second area of skin at another chosen location. This second area of skin can be adjacent to the first area of skin, or it can be distant from the first area of skin. The counter electrode can be made of any suitable conducting material including, for example, metals and conducting polymers.

When the two electrodes are properly positioned, in step 806, an initial conductivity between the two electrodes is measured. This may be accomplished by applying an electrical signal to the patch of skin through the electrodes. In one embodiment, the electrical signal supplied may have sufficient intensity so that the electrical parameter of the skin can be measured, but have a suitably low intensity so that the electrical signal does not cause permanent damage to the skin, or any significant electrophoresis effect for the substance being delivered. In one embodiment, a 10 Hz AC source is used to create a voltage differential between the source electrode and the counter electrode. The voltage supplied should not exceed 500 mV, and preferably not exceed 100 mV, or there will be a risk of damaging the skin. In another embodiment, an AC current source is used. The current source may also be suitably limited. The initial conductivity measurement is made after the source has been applied using appropriate circuitry. In one embodiment, a resistive sensor is used to measure the impedance of the patch of skin at 10 Hz. In another embodiment, a 1 kHz source is used. Sources of other frequencies are also possible.

In step 808, a skin permeabilizing device is applied to the skin at the first site. Any suitable device that increases the permeability of the skin may be used. In one embodiment, ultrasound is applied to the skin at the first site. According to one embodiment, ultrasound having a frequency of 20 kHz and an intensity of about 10 W/cm$^2$ is used to enhance the permeability of the patch of skin to be used for transdermal transport.

In step 810, the conductivity between the two sites is measured. The conductivity may be measured periodically, or it may be measured continuously. The monitoring measurements are made using the same electrode set up that was used to make the initial conductivity measurement.

In step 812, mathematical analysis and/or signal processing may be performed on the time-variance of skin conductance data. Experiments were performed on human volunteers according to the procedure above, with ultrasound used as the method of permeabilization. Ultrasound was applied until the subjects reported pain. Skin conductivity was measured once every second during ultrasound exposure. After plotting the conductance data, the graph resembled a sigmoidal curve. The conductance data was in a general sigmoidal curve equation:

$$C = C_i + (C_f - C_i)/(1 + e^{S(t-t^*)})$$

where:
C is current;
$C_i$ is current at t=0;
$C_f$ is the final current;
S is a sensitivity constant;

t* is the exposure time required to achieve an inflection point; and t is the time of exposure.

Referring again to FIG. 8, in step 814, the parameters describing the kinetics of skin conductance changes are calculated. These parameters include, inter alia, skin impedance, the variation of skin impedance with time, final skin impedance, skin impedance at inflection time, final current, exposure time to achieve the inflection time, etc.

In step 816, the skin permeabilizing device applied in step 808 is terminated when desired values of the parameters describing skin conductance are achieved. For instance, when the skin conductance increases to a certain value, the permeabilizing device may be deactivated. Alternatively, when the rate of change in the value of skin conductance is a maximum, the permeabilizing device may be deactivated. Additional details of the method for regulating the degree of skin permeabilization are disclosed in the aforementioned U.S. application Ser. No. 09/868,442.

A preferred embodiment of a continuous transdermal glucose monitoring system and method is described in connection with FIGS. 9-11. As discussed above, the term "body fluid" may include blood, interstitial fluid, lymph, and/or analyte. Body fluids include, for example, both complete fluids as well as molecular and/or ionic components thereof. Preferred embodiments of the invention may involve extraction and measurement of just the analyte.

Figure 9:
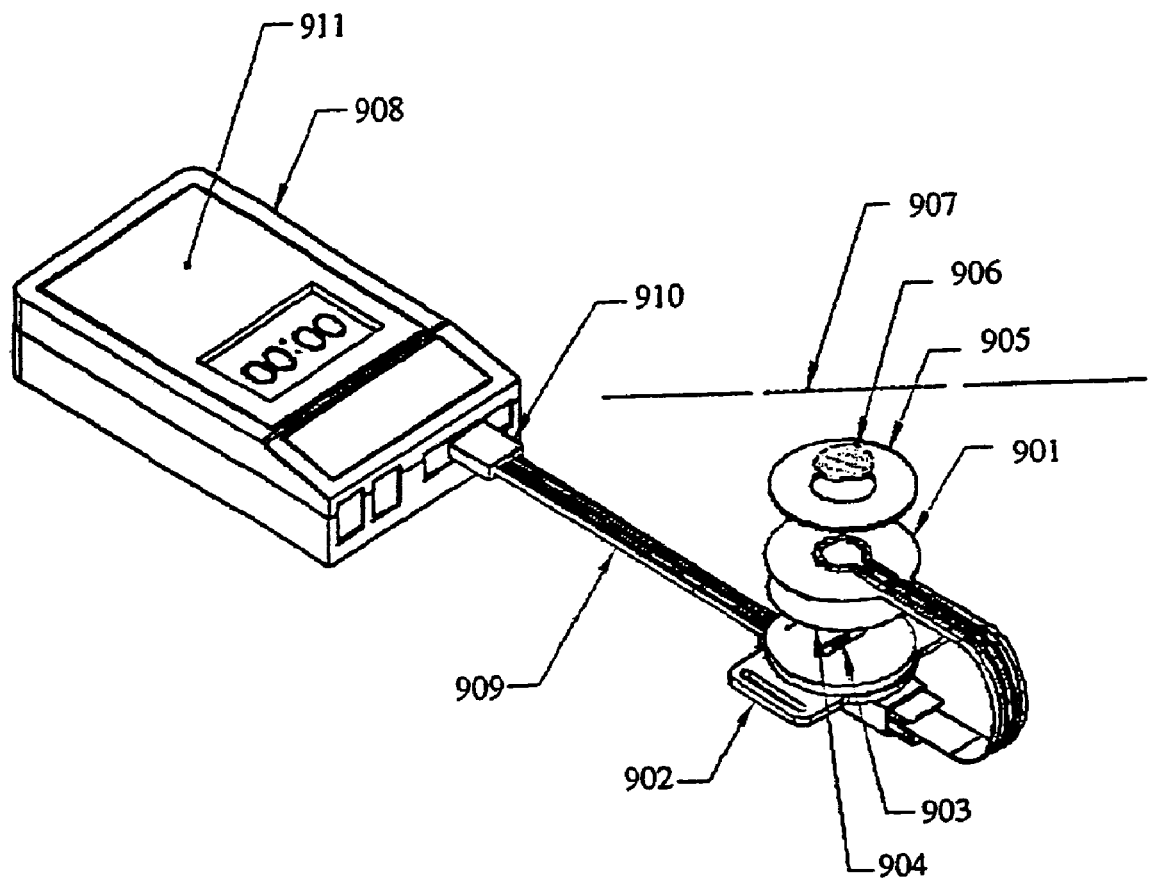
FIG. 9 depicts an apparatus for performing continuous transdermal analyte monitoring according to one embodiment of the present invention.

FIG. 9 is a drawing of a continuous glucose monitoring system according to an exemplary embodiment of the invention. In this embodiment, the system includes a sensor assembly generally including a sensor body 901 and a backing plate 902 as well as other components as described herein. The sensor body may include electrodes, as shown in FIG. 10, on its surface for electrochemical detection of analytes or reaction products that are indicative of analytes. A thermal transducer 903, which may be housed in a housing with a shape that corresponds to that of the sensor body 901, is located between the sensor body 901 and the backing plate 902. Electrochemical sensors, such as hydrogen peroxide sensors, can be sensitive to temperature fluctuation. The thermal transducer 903 may be used to normalize and report only those changes attributed to a change in analyte or analyte indicator. An adhesive disc 904 may be attached to the side of the sensor body 901 that faces the thermal transducer 903. An adhesive ring 905 may be attached to the side of the sensor body 901 that is opposite the adhesive disc 904. The cut-out center portion of the adhesive ring 905 preferably exposes some or all of the sensor components on the sensor body 901. The adhesive ring 905 and adhesive disc 904 may have a shape that corresponds to that of the sensor body as shown in FIG. 9. A hydrogel disc 906 may be positioned within the cut-out center portion of the adhesive ring 905 adjacent a surface of the sensor body 901. During operation, the sensor assembly may be positioned adjacent a permeable region 907 of a user's skin as shown by the dashed line in FIG. 9. The sensor assembly may be attached to a potentiostat recorder 908, which may include a printed circuit board 911, by way of a flexible connecting cable 909. The connecting cable 909 preferably attaches to the potentiostat recorder 908 using a connector 910 that facilitates removal and attachment of the sensor assembly.

The system shown in FIG. 9 can be used to carry out continuous monitoring of an analyte such as glucose as follows. First, a region of skin on the user is made permeable using, for example, sonication as described above. The sensor assembly, such as that shown in FIG. 9, is then attached to the permeable region 907 of skin so that the hydrogel disc 906 is in fluid communication with the permeable skin. An analyte may be extracted through the permeable region 907 of the user's skin so that it is in contact with the hydrogel disc 906 of the sensor assembly. For example, an analyte such as glucose may be transported by diffusion into the hydrogel disc 906 where it can contact glucose oxidase. The glucose can then react with glucose oxidase present in the hydrogel disc 906 to form gluconic acid and hydrogen peroxide. Next, the hydrogen peroxide is transported to the surface of the electrode in the sensor body 901 where it is electrochemically oxidized. The current produced in this oxidation is indicative of the rate of hydrogen peroxide being produced in the hydrogel, which is related to the amount of glucose flux through the skin (the rate of glucose flow through a fixed area of the skin). The glucose flux through the skin is proportional to the concentration of glucose in the blood of the user. The signal from the sensor assembly can thus be utilized to continuously monitor the blood glucose concentration of a user by displaying blood glucose concentration on the potentiostat 908 in a continuous, real-time manner.

Figure 10:
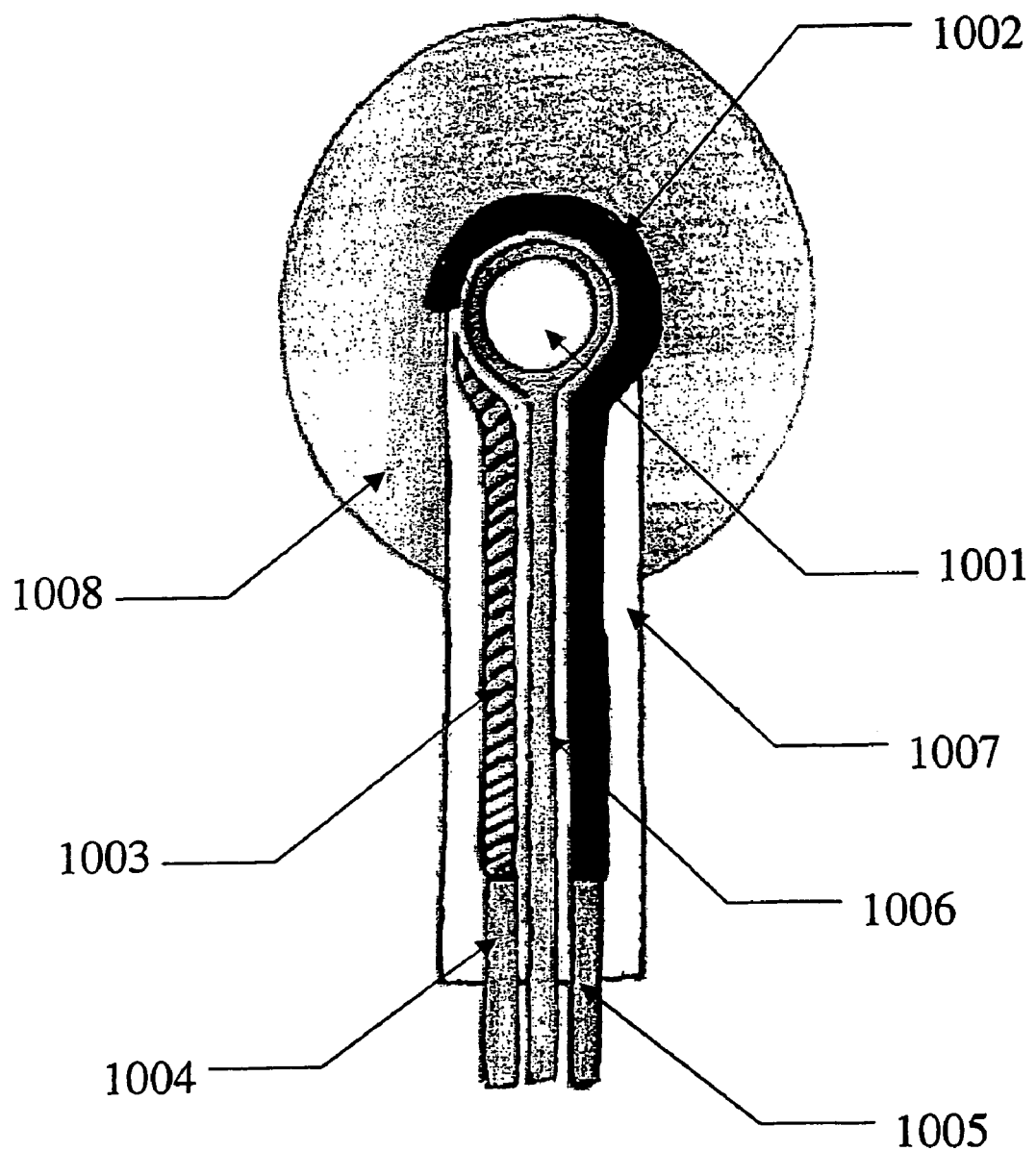
FIG. 10 is a drawing of the sensor body shown in FIG. 9 from a first view.

Detailed views of a preferred embodiment of the sensor body 901 are shown in FIG. 10. The sensor body 901 includes a body layer 1007 upon which leads 1004, 1005, and 1006 are patterned. The leads may be formed, for example, by coating metal over the body layer 1007 in the desired locations. A working electrode 1001, is typically located at the center of the sensor body 901. The working electrode 1001 may comprise pure platinum, platinized carbon, glassy carbon, carbon nanotube, mezoporous platinum, platinum black, paladium, gold, or platinum-iridium, for example. The working electrode 1001 may be patterned over lead 1006 so that it is in electrical contact with the lead 1006. A counter electrode 1002, preferably comprising carbon, may be positioned about the periphery of a portion of the working electrode 1001, as shown in FIG. 10. The counter electrode 1002 may be patterned over lead 1005 so that it is in electrical contact with the lead 1005. A reference electrode 1003, preferably comprising Ag/AgCl, may be positioned about the periphery of another portion of the working electrode 1001 as shown in FIG. 10. The electrodes 1001, 1002, and 1003 can be formed to roughly track the layout of the electrical leads 1006, 1005, 1004, respectively, that are patterned in the sensing area of the device. The electrodes 1001, 1002, and 1003 may be screen printed over the electrical leads 1006, 1005, 1004, respectively. The leads can be pattered, using screen printing or other methods known in the art, onto the sensor body 901 in a manner that permits electrical connection to external devices or components. For example, the leads may form a 3× connector pin lead including leads 1004, 1005, and 1006 at the terminus of an extended region of the sensor body as shown in FIG. 10. A standard connector may then be used to connect the sensor electrodes to external devices or components.

The electrochemical sensor utilizes the working electrode 1001, the counter electrode 1002, and the reference electrode 1003 to measure the rate hydrogen peroxide or glucose is being generated in the hydrogel. The electrochemical sensor is preferably operated in potentiostat mode during continuous glucose monitoring. In potentiostat mode, the electrical potential between the working and reference electrodes of a three-electrode cell are maintained at a preset value. The current between the working electrode and the counter electrode is measured. The sensor is maintained in this mode as long as the needed cell voltage and current do not exceed the current and voltage limits of the potentiostat. In the potentiostat mode of operation, the potential between the working and reference electrode may be selected to achieve selective electrochemical measurement of a particular analyte or analyte indicator. Other operational modes can be used to investigate the kinetics and mechanism of the electrode reaction occurring on the working electrode surface, or in electroanalytical applications. For instance, according to an electrochemical cell mode of operation, a current may flow between the working and counter electrodes while the potential of the working electrode is measured against the reference electrode. It will be appreciated by those skilled in the art that the mode of operation of the electrochemical sensor may be selected depending on the application.

Figure 11:
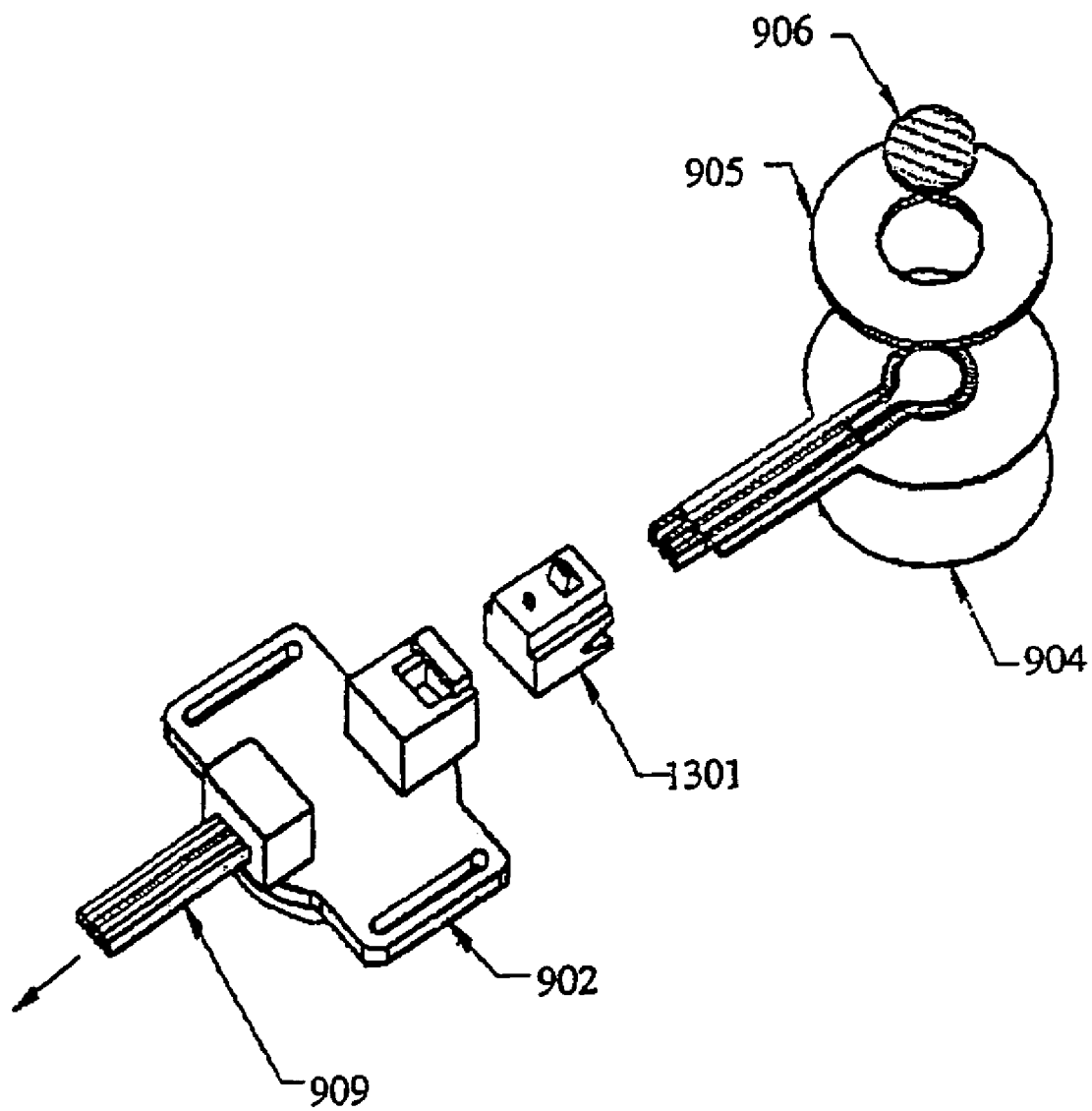
FIG. 11 is a drawing of the apparatus shown in FIG. 9 from a second view.

The sensor assembly described generally in relation to FIG. 9 is show in expanded detail from another angle in FIG. 11. The sensor body 901, which is covered on each side by adhesive disc 904 and adhesive ring 905, is shown in relation to the backing plate 902. The hydrogel disc 906 may be positioned in such a manner that it will face toward the user after folding over onto the backing plate 902 as shown in FIG. 9. The sensor body may be connected to the backing plate 902 using standard connectors such as a SLIM/RCPT connector 1301 with a latch that mates with a corresponding connector interface that is mounted onto the backing plate 902.

The sensor assembly shown in FIGS. 9-11 may be incorporated into any one of a number of detection devices. For instance, this sensor assembly may be incorporated into the receiver of FIG. 4 to provide for discrete and/or continuous glucose monitoring. Additionally, the sensor assembly may be connected to a display or computing device through a wireless connection or any other means for electrical connection in addition to the cable 909.

Continuous glucose monitoring as described herein can be achieved without accumulation of a certain volume of body fluid in a reservoir before measuring the concentration of the withdrawn fluid. Continuous glucose monitoring is capable of measuring the blood concentration of glucose without relying on accumulation of body fluids in the sensor device. In continuous glucose monitoring, for instance, one may prefer to minimize accumulation of both glucose and hydrogen peroxide in the hydrogel so that the current measured by the electrochemical sensor is reflective of the glucose flux through the permeable region of skin in real-time. This advantageously permits continuous real-time transdermal glucose monitoring.

According to another aspect of the invention, a step of skin hydration may be employed prior to or concurrently with increasing the porosity of the skin (e.g. by applying ultrasound) to improve the continuous transdermal analyte monitoring. Skin hydration prior to or concurrently with increasing the porosity, and prior to attaching the sensor may improve sensor performance by establishing or stabilizing liquid pathways between the skin and the sensor, improving the moisture balance over the sensor-skin interface, and/or continuing to maintain ample water to the hydrogel to maintain enzyme activity. The skin hydration procedure can be performed, for example, by applying a hydrating agent to the target skin site. The hydrating agent may be applied in combination with a delipidation or cleansing agent. Where both hydrating and cleansing agents are utilized, they may be applied in a single application using a single solution. Alternatively, the cleansing agent and the hydrating agent can be applied using successive application of two different solutions. In one aspect, one or both solutions are applied using a pad applicator. In another aspect, the solution can be held in contact with the skin by positioning it in the bellows of a sonication device or another device that might function to hold a liquid in contact with skin.

In one embodiment, a glycerin/water prep pad solution may be prepared for skin hydration. The following batch formulation can be used to prepare the glycerin/water prep pad solution. 300.00 grams of glycerin 99% USP is added to the first container. 2.70 grams of Nipagin M (methylparaben), 0.45 grams of Nipasol M (propylparaben), and 30.00 grams of benzyl alcohol NF are dissloved in a second container and then added to the first container. The glycerin and benzyl alcohol solutions are then mixed in the first container until the solution clears. 133.85 grams of deionized water is then added to the solution in the first container and mixed until homogeneous. 1.50 grams of Potassium Sorbate NF is added to the solution in the first container and mixed until homogenious. 1.50 grams of Glydant 2000 is then added to the solution in the first container and mixed until homogenious. Lastly, 30.00 grams of deionized water is added to the solution in the first container and mixed until homogeneous.

In one embodiment, a 1 3/16" prep pad is utilized. Preferably the prep pads are composed of 70% polypropylene/30% cellulose. In one embodiment, the prep pad has a width that ranges from 1 1/16" to 1 5/16. In one embodiment, the thickness of the prep pad is 21-29 mils. In another embodiment, the thickness of the prep pad is 26-34 mils. In one embodiment the prep pad has a basis weight of 1.43-1.87 g/yd using ATM#102. In another embodiment, the prep pad has a basis weight of 1.72-2.24 g/yd using ATM#102. Preferably, the prep pad is utilized with a prep pad solution, such as the prep pad solution above, to hydrate a biological membrane before increasing its porosity.

According to another aspect of the invention, the working electrode 1001 of FIG. 10 may include a surface layer of pure platinum. The pure platinum working electrode 1001 may be screen printed or otherwise coated onto the surface of a lead 1006. Using pure platinum as the working electrode can enhance sensitivity and increase the rate of conversion of hydrogen peroxide. This can provide advantages for continuous transdermal glucose monitoring as the conversion of hydrogen peroxide is preferably fast to prevent its accumulation, which may cause positive sensor drift and/or enzyme deactivation. In transdermal glucose sensing applications, pure platinum can offer advantages over traditional platinized carbon materials.

Figure 13:
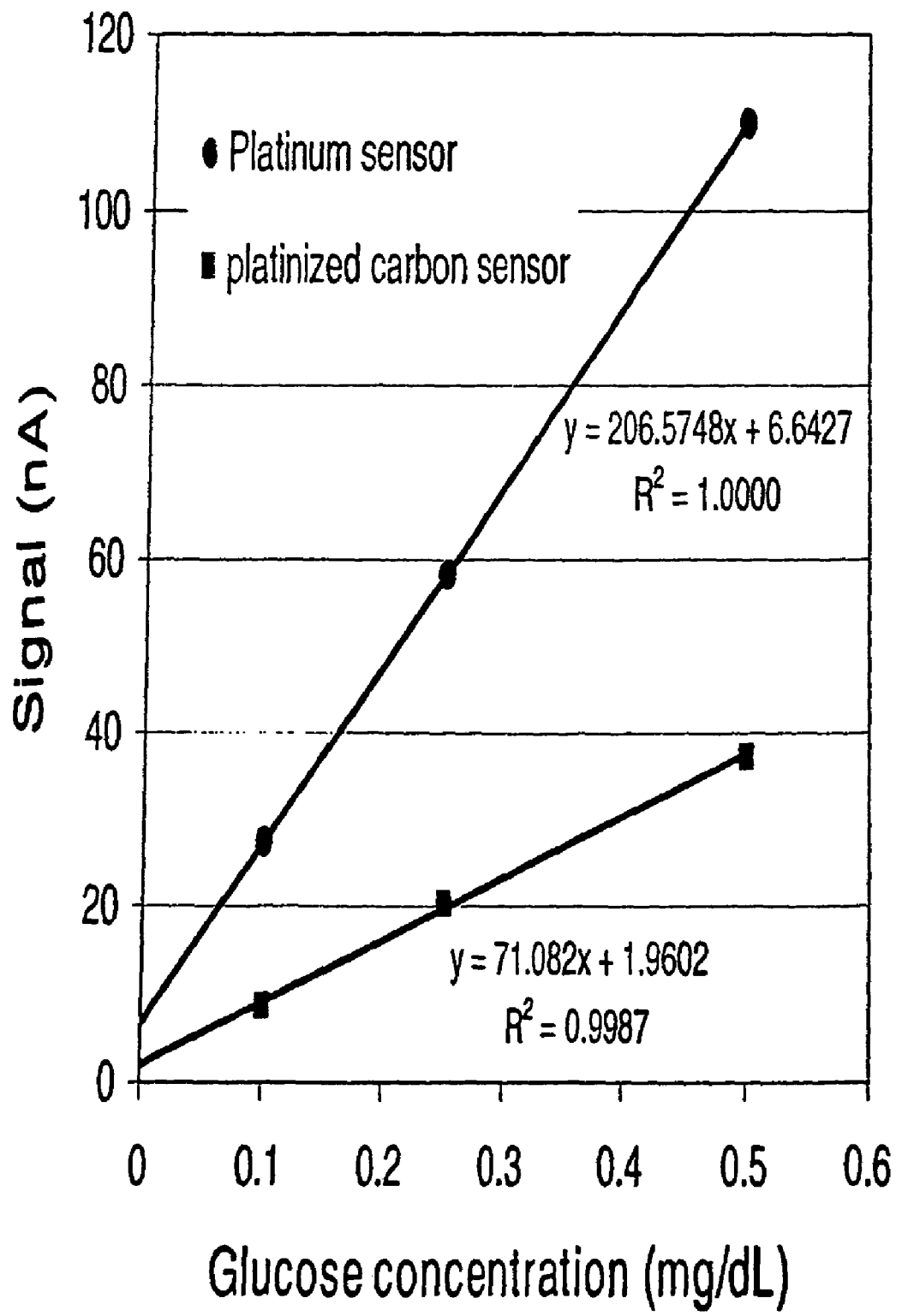
FIG. 13 shows the signal response versus glucose concentration for pure platinum versus platinized carbon as the working electrode.

One advantage that pure platinum can offer relative to platinized carbon is an enhanced sensitivity to glucose concentration. FIG. 13 shows the glucose sensitivity of both pure platinum and platinized carbon. As shown by this comparison, the glucose sensitivity of pure platinum is about 2.9 times that of platinized carbon. The glucose sample size used to generate the data of FIG. 13 was 2 microliters.

Figure 14:
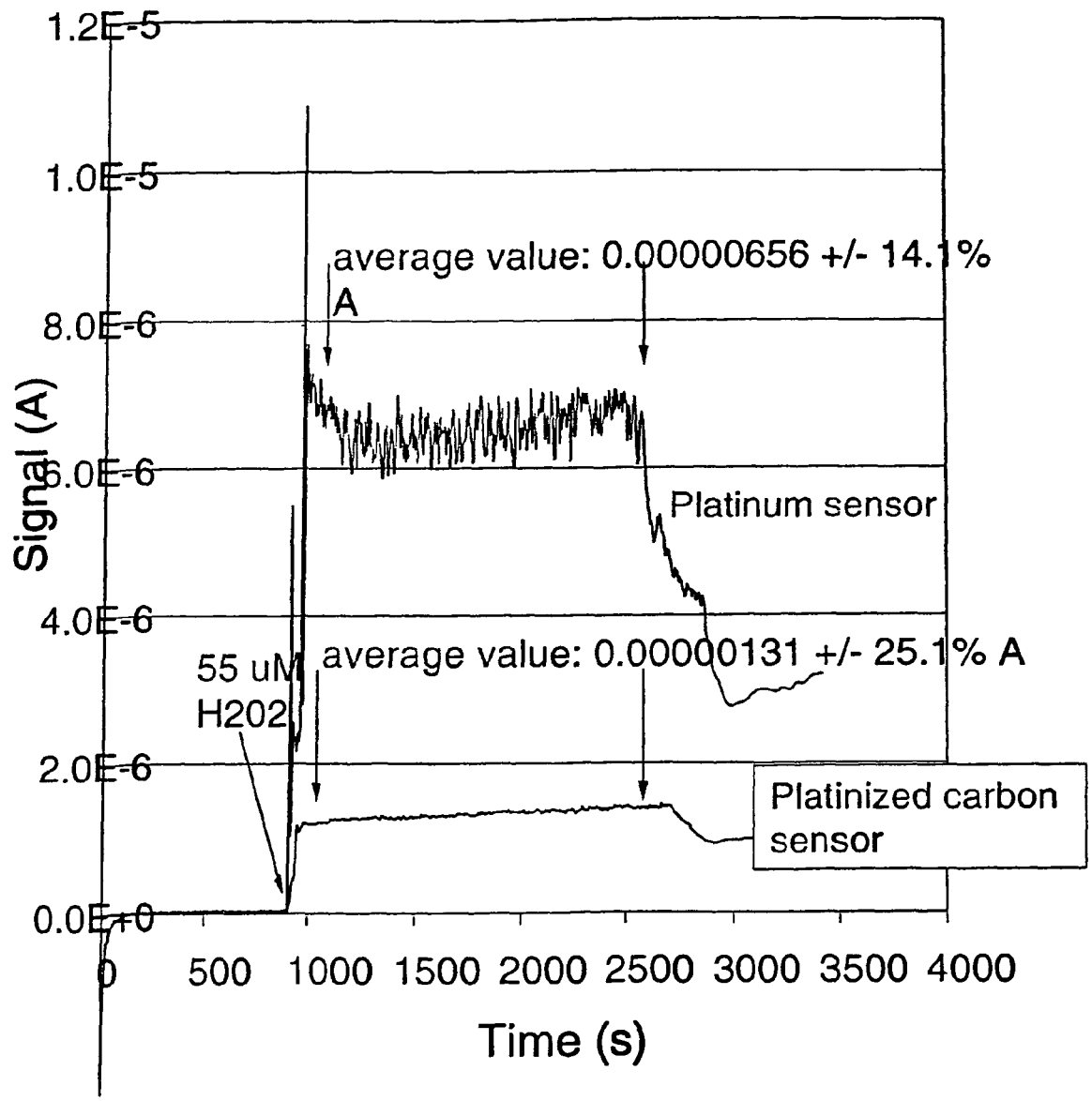
FIG. 14 shows the current-time profiles of a glucose sensor responding to the addition of hydrogen peroxide using platinum and platinized carbon as the working electrode.

Another advantage that pure platinum can offer relative to platinized carbon is enhanced sensitivity to hydrogen peroxide. FIG. 14 shows the hydrogen peroxide sensitivity of both pure platinum and platinized carbon. Specifically, FIG. 14 shows the current-time profiles of a glucose sensor responding to the addition of hydrogen peroxide (sometimes referred to as a hydrogen peroxide "challenge") using platinum and platinized carbon as the working electrode. As shown by this comparison, the hydrogen peroxide sensitivity of pure platinum is about 5 times that of platinized carbon.

Another advantage that pure platinum can offer relative to platinized carbon is a higher success rate for glucose monitoring. The percentage success rate for glucose monitoring using pure platinum was 83% versus 60% for platinized carbon (correlation coefficient $R^2 >= 0.5$ as the passing criteria). R refers to the correlation between conventional whole blood glucose measurements and measurements of blood glucose using the system of FIG. 9. R is calculated by comparing the continuous data from the system of FIG. 9 with discrete whole blood measurements (taken every 20 minutes). A linear regression analysis is run on the two data sets to generate an R value. The correlation between sensor signal and blood glucose levels using pure platinum was $R^2=0.87$ versus $R^2=0.71$ for platinized carbon.

According to another aspect of the invention, a protective interference filter can be provided to reduce or even eliminate interference effects from unwanted electrochemical oxidation and/or biofouling. One form of interference, for example, involves the production of unwanted anodic signal by electrochemical oxidation of ascorbic acid, uric acid, and/or acetaminophen, which can all be oxidized electrochemically at voltage levels applied in glucose monitoring. Another form of interference can involve biofouling, which can occur when biological species deposit on a sensor surface thereby limiting the sensor's free access to analyte or deactivating its functionality by reacting with the electrode. It is generally advantageous to reduce or eliminate the effects of interfering species through the use of an interference filter since many of these species may be present in body fluids during glucose monitoring.

According to an exemplary embodiment of the invention, the interference filter comprises a Nafion film coated onto one or more surfaces of the sensor assembly. Other interference filter materials such as (3-mercaptopropyl)trimethylsilane, cellulose acetate, electropolymerized films such as 1,8-diaminonapthaline and phenylenediamine, PTFE or other hydrophobic, Nylon or other hydrophylic membranes may be used. Nafion is a biocompatible anionic fluoropolymer that can be coated on sensor surfaces as a protective layer against physiological interferents and biofouling based on hydrophobicity, charge selection, and size exclusion, for example. Nafion is available from Aldrich Chemical of Milwaukee, Wis. A Nafion film may be coated directly on the surface of at least the working electrode 1001 of the sensor body 901. Alternatively, a Nafion film may be coated on an outer surface of the sensor assembly such as the hydrogel layer 906. In general, one or more interference filter layers may be provided between the working electrode surface and any other layer or on the outermost surface of the sensor assembly that contacts the user's skin during operation.

Figure 15:
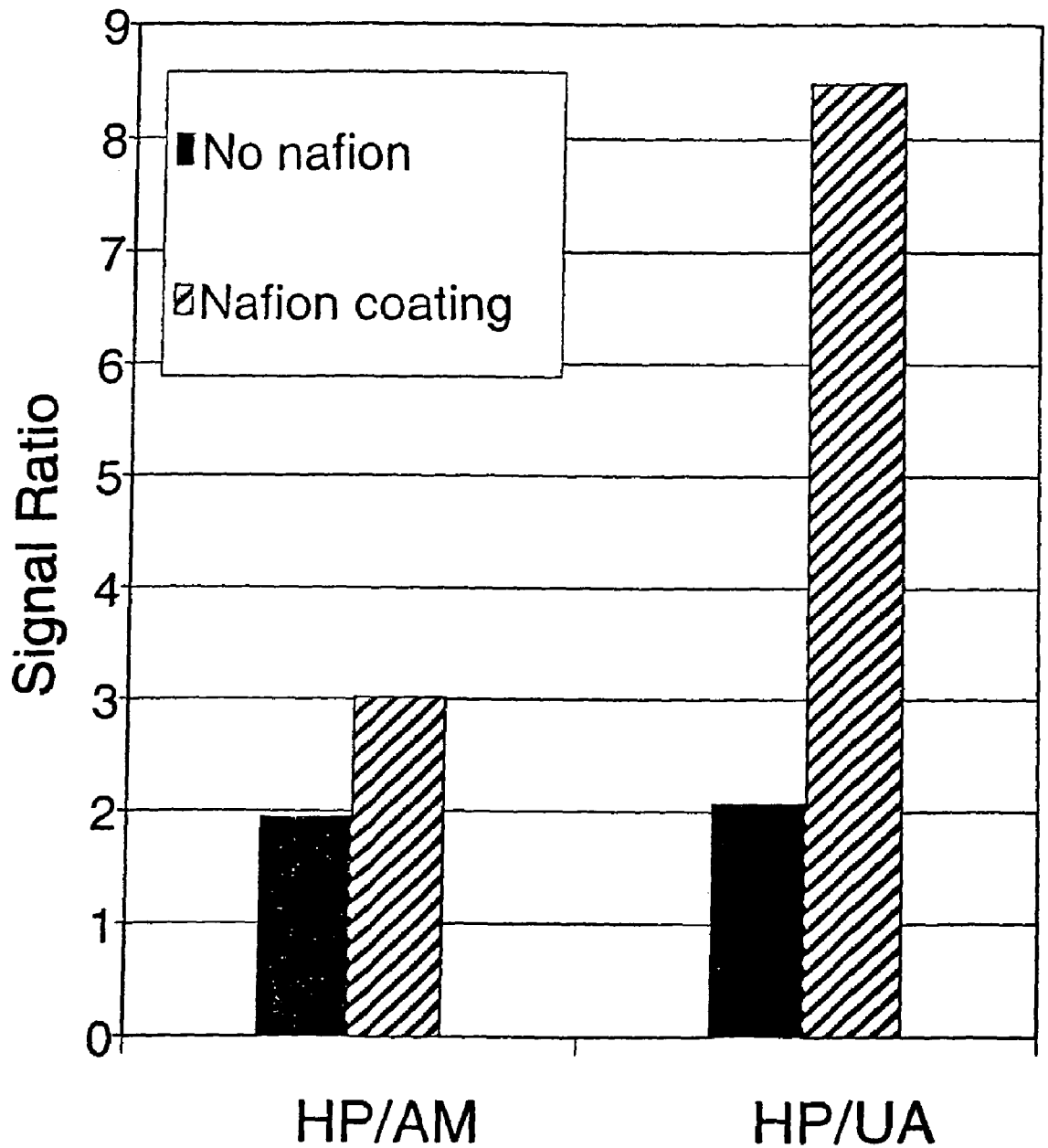
FIG. 15 shows the sensor response to hydrogen peroxide (HP) over acetominophen (AM) and hydrogen peroxide over uric acid (UA) for sensors with and without a Nafion interference filter.

A Nafion layer can be conveniently coated on a sensor surface using a micropipette, for example, or by dip-coating the sensor in aqueous or organic Nafion solution followed by air drying for several hours before use. FIG. 15 shows the effect of a Nafion coating on the sensor response to glucose relative to the interferents acetaminophen and uric acid. The plot shows the hydrodynamic sensor response to 0.294 mM of hydrogen peroxide (HP) over acetominophen (AM) and uric acid (UA) in phosphate buffered saline with 0.5 V of applied voltage. The amperometric current produced by acetaminophen and uric acid is greatly reduced for a sensor coated with Nafion relative to an uncoated sensor. Thus, Nafion can significantly improve the analyte/interferent signal ratio.

In various embodiments of the invention described herein, hydrogels can be used as part of the analyte monitoring system. Hydrogels constitute an important class of biomaterials utilized for medical and biotechnological applications such as in contact lenses, biosensors, linings for artificial implants and drug delivery devices. FIGS. 9 and 11 show a preferred hydrogel disc 906 in relation to the sensor assembly. The hydrogel disc 906 may be located over the sensor body 901 within the cutout center portion of the adhesive ring 905 of the sensor assembly. The continuous transdermal analyte monitoring system may utilize one or more of the preferred hydrogel materials described below. Classes of hydrogel materials that may be used in exemplary embodiments of the invention include: agarose based hydrogels, polyethylene glycol diacrylate (PEG-DA) based hydrogels, and vinyl acetate based hydrogels, for example. Following a general description of these gels are examples detailing the procedures used to produce and/or characterize the various hydrogels.

Agarose based hydrogels can offer advantages for continuous transdermal analyte monitoring. For instance, agarose can offer one or more of the following features: good response to glucose and hydrogen peroxide due to its high water content, high enzyme loading, good bio-compatibility, and excellent permeation and diffusion properties. In addition, agarose hydrogels may offer cleanliness, low cost, and/or ease of preparation.

An agarose gel may be formed, for example, from 1-20% agarose in buffer solution containing 0-1 M sodium or potassium phosphate, 0-1 M sodium chloride, 0-1 M potassium chloride, 0-2 M lactic acid, surfactant such as 0-1 M Triton X-100, Tween 80 or sodium lauryl sulfate, and any other biocompatible components. Loading of glucose oxidase in agarose hydrogel can be up to 0-20% (by weight), for example, by soaking the solid hydrogel in concentrated glucose oxidase solution, or alternatively by mixing concentrated glucose oxidase powder or solution with agarose solution during its melting stage (15-65° C.), followed by cooling and gelling at lower temperature (40° C. or lower).

PEG based hydrogels can offer several advantages for continuous transdermal analyte monitoring. Structurally, PEG is highly hydrophilic and presents a high degree of solvation in aqueous solvents. The preferential solvation of PEG molecules can effectively exclude proteins from the PEG chain volume, thereby protecting the surface from bio-fouling by proteins. An advantage that can be provided by chemically crosslinked PEG-based hydrogels is that their physical and chemical properties can be modulated by varying the molecular weight of the PEG chains and varying the initiator concentration. For example, increasing the molecular weight of the polyethylene oxide backbone increases the network mesh size. The release of a bioactive molecule such as an enzyme can be controlled by control of the network density. Therefore, a hydrogel comprised of PEGs of molecular weight 8000 daltons would have a higher rate of release of an entrapped drug than a hydrogel comprised of PEGs of molecular weight 3.3K. Furthermore, ionic moieties can be incorporated into the hydrogels to impart added functionalities such as bioadhesiveness, etc. For example, hyaluronic acid or polyacrylic acid can be added to the PEG macromer prior to crosslinking to create bioadhesive hydrogels. In another example, an ionic character can be imparted to the crosslinked hydrogels to provide molecular interaction with entrapped drugs to slow down rates of release of drug from the matrix.

PEG-hydrogels used in biosensors can provide one or more of the following features: (a) a biocompatible, non-biofouling surface appropriate for long-term exposure to biological fluids without compromise of sensor function, (b) a reservoir for glucose oxidase, (c) a matrix that can be incorporated with ionic moieties to enhance entrapment of glucose oxidase, (d) a matrix that can be modulated in terms of its physical and chemical properties (network density, swelling) by varying the molecular weight of the backbone and (e) a matrix that can be rendered bioadhesive by addition of ionic excipients such as chitosan gluconate, polyacrylic acid, poly(amidoamine), poly(ethyleneimine) and hyaluronic acid.

Vinyl acetate based hydrogels, such as n-vinylpyrolidone/ vinyl acetate copolymer, can exhibit features such as transparency, tackiness, non-toxicity, flexibility, and/or hydrophobicity. Vinyl acetate based hydrogels typically have a good ability to retain moisture and entrap enzymes such as glucose oxidase, biocompatibility, and tackiness to skin to improve skin-sensor coupling. A glucose flux sensor using n-vinylpyrolidone/vinyl acetate copolymer as the hydrogel material shows good performance in tracking the plasma glucose levels of a patient with diabetes during a glucose clamping study.

The following examples set forth exemplary hydrogels that can be used with transdermal analyte monitoring according to embodiments of the present invention.

Example 2

Vinyl acetate based hydrogels for use with glucose monitoring can be prepared as follows. A 1:1 mixture of n-vinylpyrolidone and vinyl acetate can be polymerized by ultraviolet radiation using 0-0.5% Irgacure as the photoinitiator. A nonwoven plastic scrim (such as Delstar product# RB0707-50P) is used to provide mechanic support. The hydrogel's equilibrium water content is 20-95% with its aqueous composition containing 0-1 M sodium or potassium phosphate, 0-1 M sodium chloride, 0-1 M potassium chloride, 0-2 M lactic acid, surfactant such as 0-1 M Triton X-100, Tween 80 or sodium lauryl sulfate, and any other biocompatible components. Glucose oxidase can be loaded by soaking the solid hydrogel layer in concentrated glucose oxidase solution for a period of time.

A particular example of a vinyl acetate based hydrogel was made with the following constituents: 15% n-vinylpyrolidone, 15% vinyl acetate, 0.05% Irgacure, 0.05 M potassium phosphate, 0.30 M sodium chloride, 0.025 M potassium chloride, 0.5 M lactic acid, 0.1% Triton X-100, 0.5% GOx, and the remaining composition is water, approximately 65%

Figure 25:
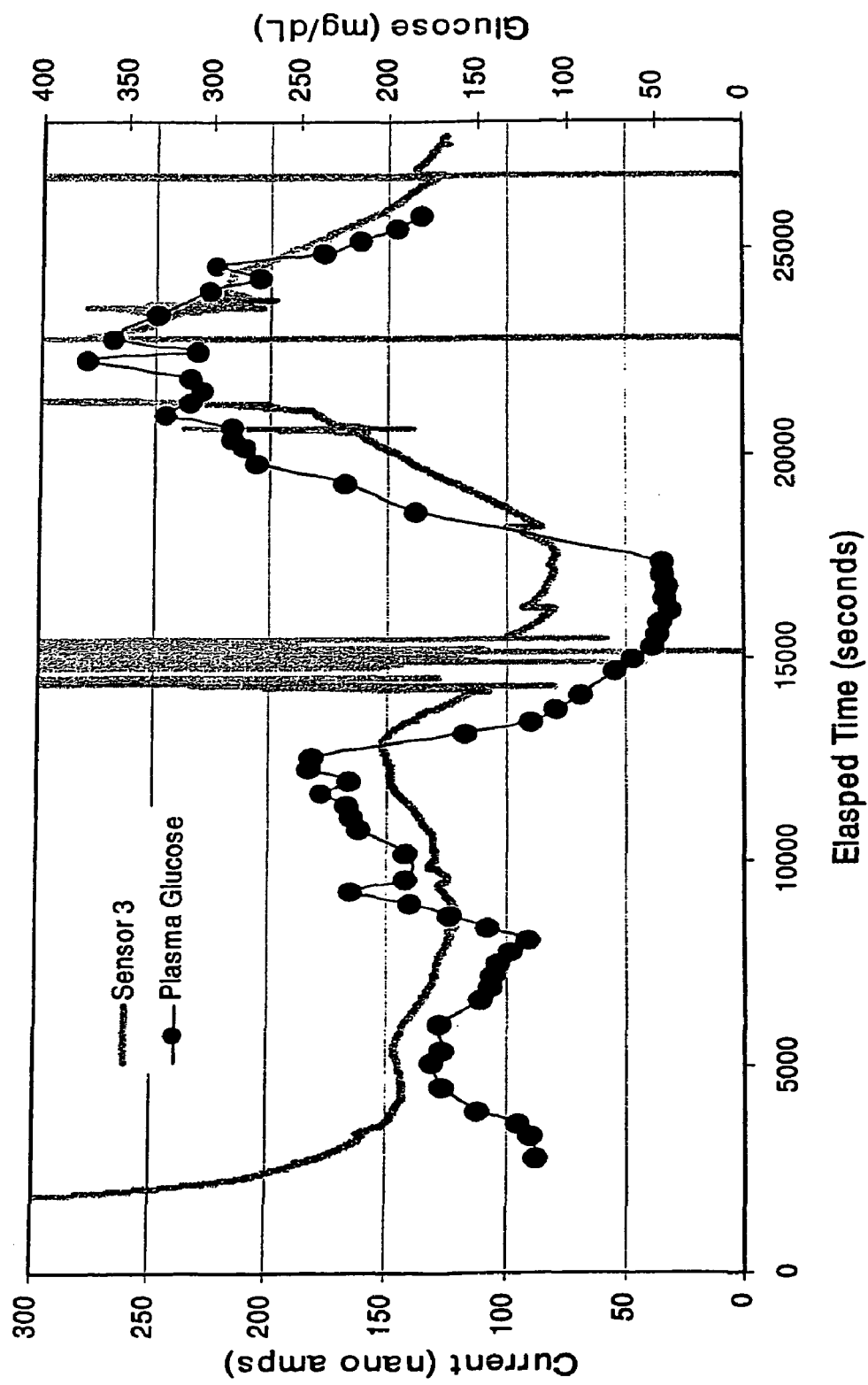
FIG. 25 shows a noisy data set from the clinical study.
Figure 26:
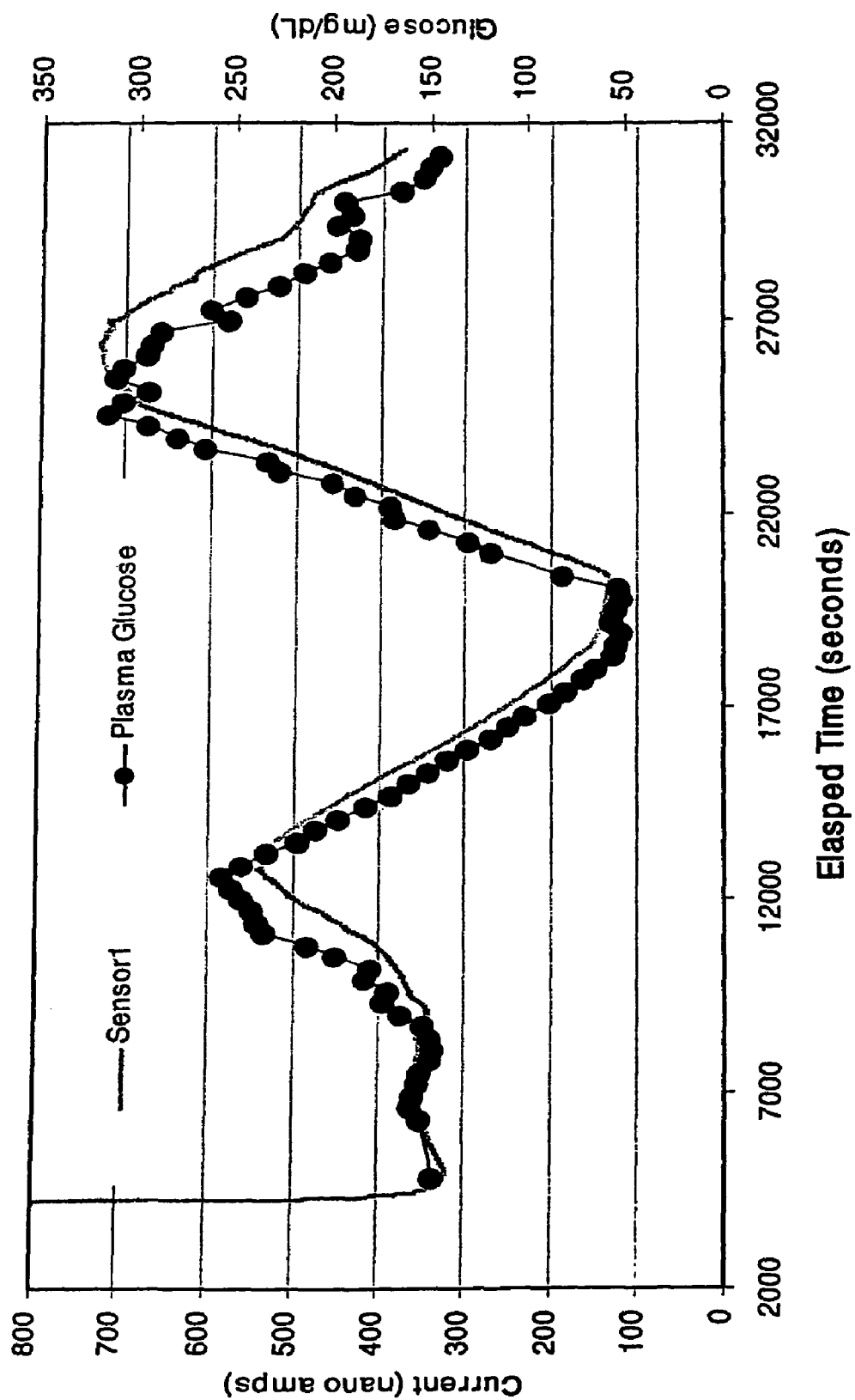
FIG. 26 shows another data set from the clinical study.
Figure 27:
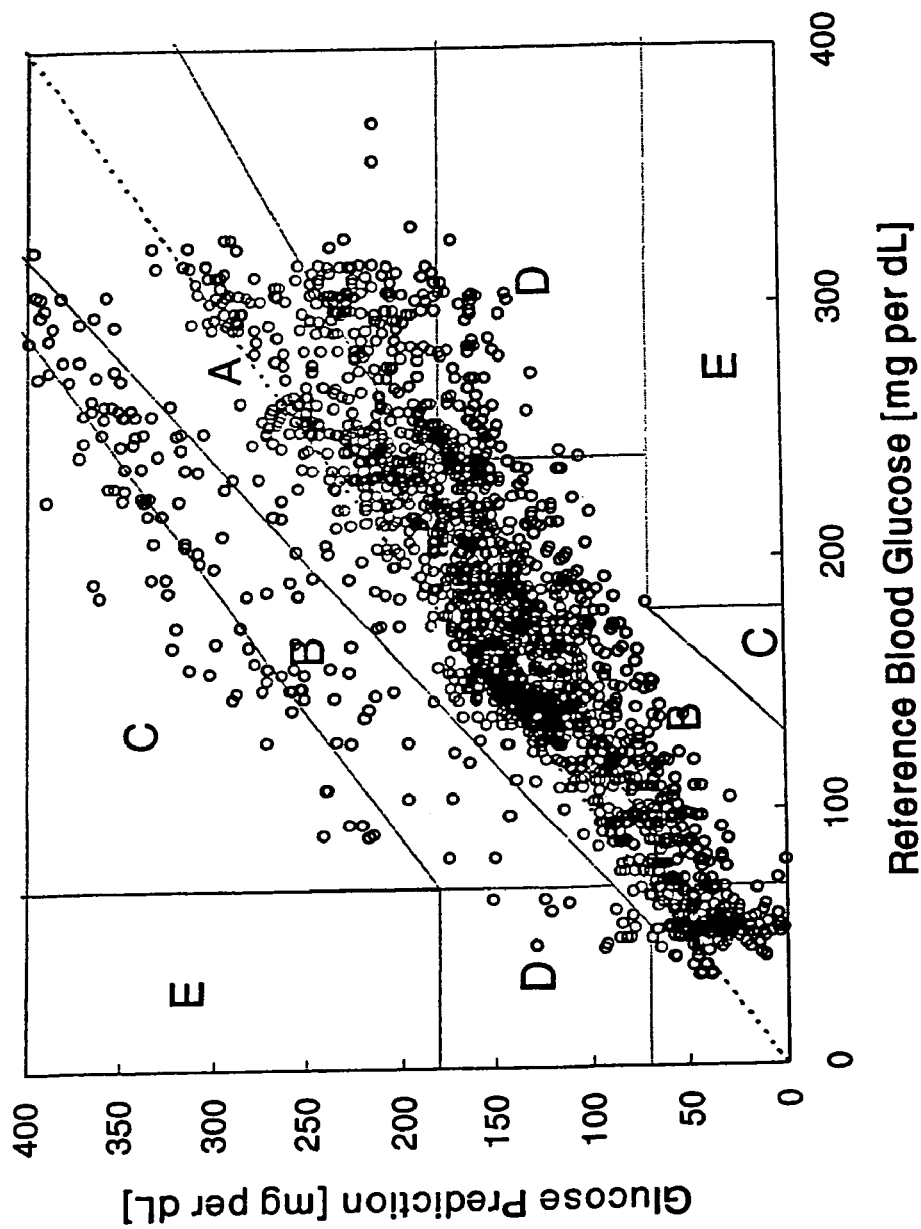
FIG. 27 shows a Clark Error Grid for sensor data from the clinical study according to one embodiment of the invention.
Figure 28:
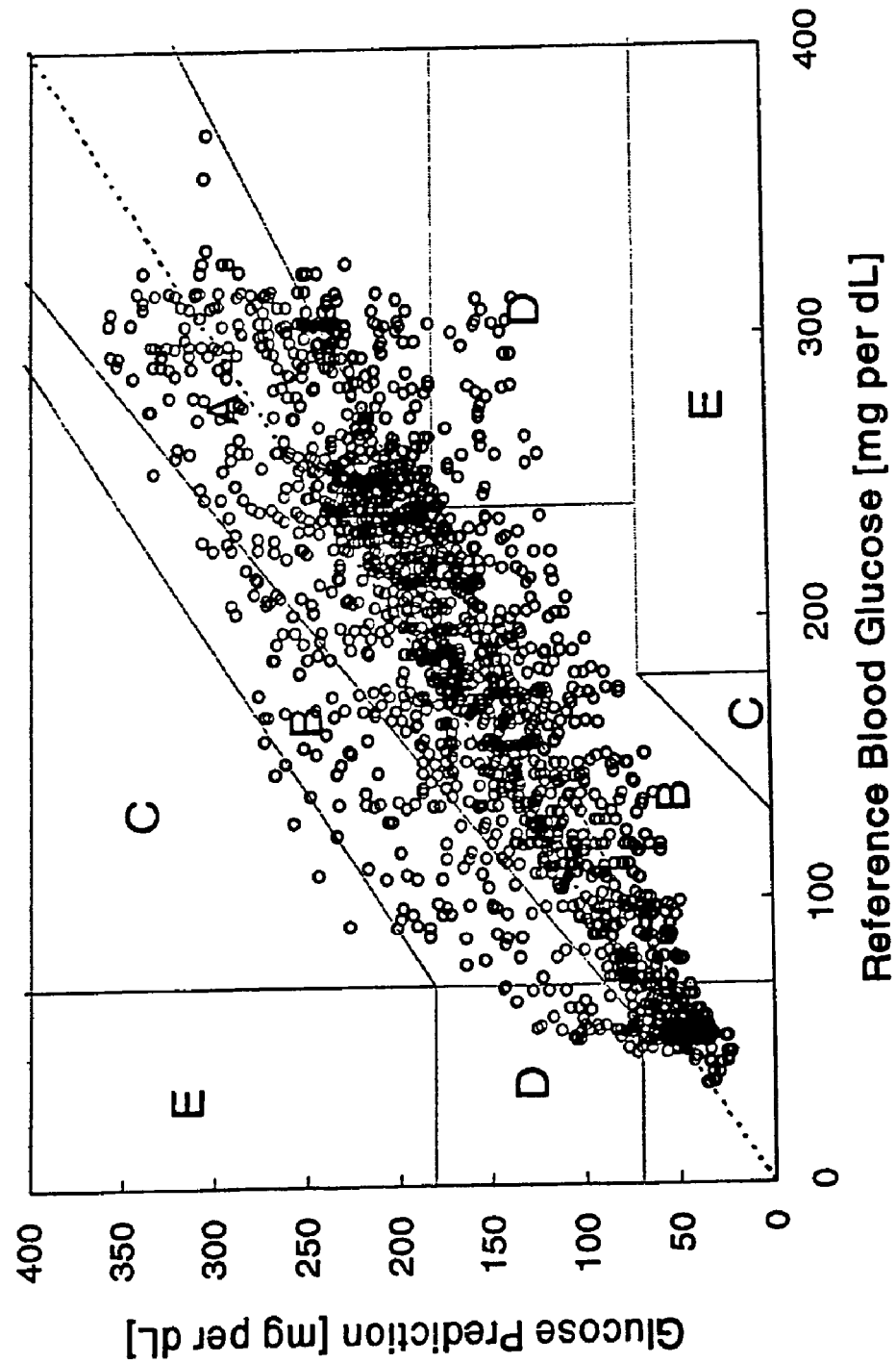
FIG. 28 shows a Clark Error Grid for sensor data from the clinical study according to another embodiment of the invention.

The continuous transdermal analyte monitoring system according to an exemplary embodiment of the present invention was used to reliably predict hypoglycemia (blood glucose<70 mg/dl) with 96% specificity and 77% sensitivity using a vinyl acetate hydrogel. In a study, thirty six glucose flux biosensors (3 per patient) were placed on the skin of twelve adults with either Type 1 or Type 2 diabetes. Patient data for participants in the study are shown in FIG. 24. Blood glucose measurements were collected over an eight hour period. These measurements included collecting current versus time data from the patients using a continuous transdermal analyte monitoring system as described herein. The blood glucose of each patient was rapidly increased or decreased through the administration of insulin or glucose intravenously in a controlled manner at a rate of change two times greater than that usually experienced by patients with diabetes. Specifically, the ranges tested were 35-372 mg/dl blood glucose, with a rate of glucose concentration decrease of 21 mg/(dl*min) and rate of glucose concentration increase of 11 mg/(dl*min). As a control, blood glucose measurements were collected from an intravenous catheter. A total of 2039 sensor-blood glucose data pairs from 29 data sets were generated. Five of the data sets had significant noise as shown in FIG. 25. The typical data set, however, kept noise below an excessive level as shown, for example, in FIG. 26. The data sets were analyzed with both an individually optimized algorithm and an independent algorithm, and the results are shown in FIGS. 27 and 28, respectively. The individually optimized algorithm used each data set's optimal lag time and baseline for data analysis. The independent algorithm was developed from a separate glucose clamping study, from which a single lag time value and a single baseline value were found, then were used in the algorithm for data analysis. As will be described below in connection with FIG. 17, an additional algorithm can also be utilized to compensate for temperature change and sensor drift. Completed data sets from the glucose biosensors showed a 90 percent (R=0.9) correlation to blood glucose measurements obtained via intravenous catheter over a period of 8 hours. Ninety six percent of the sensor-blood glucose pairs fell within the A+B regions in the Clark Error Grid. Seventy seven percent (164 out of 212) hypoglycemic events (BG<70 mg/dL) were successfully predicted. Sonication treatment (using Sonoprep) averaged 15 seconds and the glucose sensor required only 89+/−6 minutes on average to break in. No pain or irritation was reported during the sonication procedure. Accordingly, the glucose biosensor was able to reliably predict hypoglycemia (blood glucose<70 mg/dl) with 96% specificity and 77% sensitivity.

Example 3

Agarose based hydrogels for use with glucose monitoring were prepared as follows. 0.0116 g of sodium chloride, 0.015 g of potassium chloride, 0.0348 g of dibasic potassium phosphate and 0.002 g of Triton X-100 were dissolved in 10 mL of water. The pH of the solution was adjusted to 7.0 using 0.5 M hydrochloric acid with the aid of a pH meter. The solution was diluted with water to 20 mL. This was Solution A. 0.2 g of agarose powder was mixed and dispersed in Solution A. Agarose was heated and dissolved until boiling in a water bath. This was Solution B. Solution B was allowed to cool down to 35° C. 0.01 g of glucose oxidase powder was completely mixed and dissolved in Solution B. This was Solution C. Solution C was cast and filled onto a warm, flat mold surface. The mold was transferred to room temperature or lower to form gels.

Figure 12:
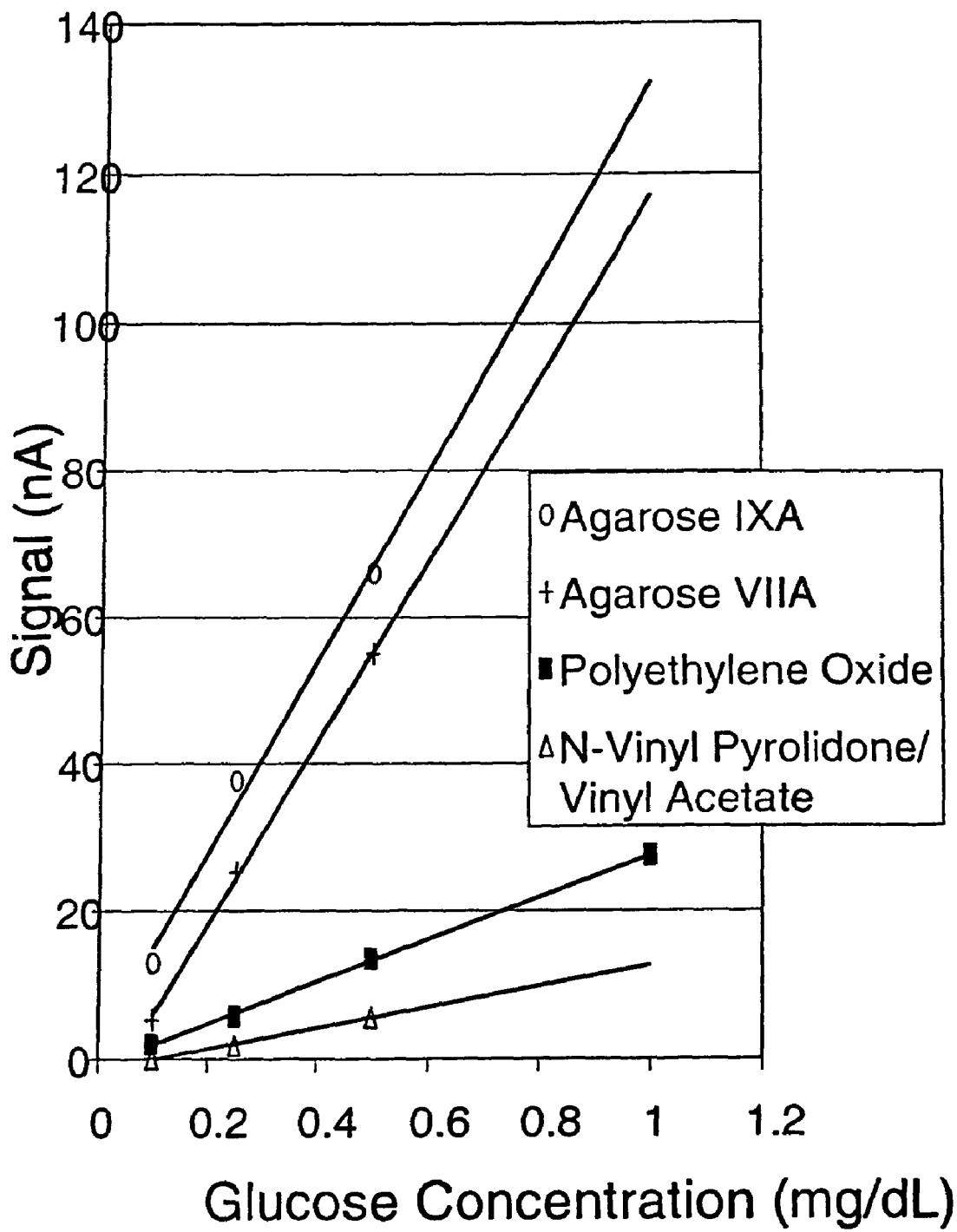
FIG. 12 shows the signal response versus glucose concentration for various hydrogels.

FIG. 12 shows sensor signal response as a function of glucose concentration for two types of agarose hydrogels relative to a polyethylene oxide polymer, and a n-vinyl pyrolidone/vinyl acetate copolymer. It can be seen from FIG. 12 that agarose offers improved signal response relative to polyethylene oxide polymer and n-vinyl pyrolidone/vinyl acetate copolymer.

Example 4

Agarose based hydrogels for use with glucose monitoring can also be prepared as follows. Mix and disperse 0.2 g of agarose powder in water. Heat and dissolve agarose until boiling in a water bath. Cast and fill the solution onto a warm, flat mold surface. Transfer the mold to room temperature or lower to form gels. Dissolve 0.01 g of glucose oxidase powder in Solution A to form Solution D. Soak the gel in Solution D overnight or longer to ensure sufficient loading of glucose oxidase in the gel.

Example 5

PEG-diacrylate (PEGDA) hydrogels utilized in glucose monitoring were prepared according to the following procedures.

10% weight/volume ("w/v") solutions of (100 mg/ml) PEG2K-diacrylate, PEG3.4K-diacrylate and PEG8K-diacrylate (SunBio, Korea) were prepared in 0.01M phosphate buffered saline (PBS), pH 7.4 (ultrapure, Spectrum Chemicals, Gardena, Calif.). The solutions all contained Irgacure 2959 (Ciba Specialty Chemicals, Tarrytown, N.Y.) as the photoinitiator. Irgacure concentrations were varied to determine the effect of photoinitiator concentration on gel strength. Similarly, the polymer molecular weights were varied (2K, 3.4K, 8K) to determine the effect of molecular weight on the strength of the gelled network. As used herein, the notation "PEG2K" refers to PEG having a molecular weight of 2,000, etc.

100 mg of dry polymer was weighed into a scintillation vial. 900 µl of phosphate buffered saline (PBS) containing 500 ppm of Irgacure 2959 was added to the vial and the final weight of the solution was recorded. The vial was screw-capped and the vial swirled gently to dissolve the PEGDA. The gel solution was stored in the drawer (in the dark) for 5 minutes to ensure homogeneity. 900 µl of the gel solution was placed between two glass plates (250µ spacers) and clamped. The glass assembly containing the polymer solution was placed under a UV Blak-Ray lamp, at an intensity of 15-20 mW/cm$^2$ and photo-crosslinked between 5-30 minutes. The gel was removed carefully from the glass and weighed before transferring to 10 ml of PBS in a plastic petri dish. After removal from the glass plates, the hydrogels were placed in approximately 10 ml of PBS. The hydrogels were then qualitatively assessed for bulk gel properties such as brittleness, gel strength and photo-yellowing as a function of molecular weight and initiator concentration.

The following procedure was used to measure the equilibrium hydration of the gels. The gels were weighed after curing was complete. The initial weight of the gel was obtained, post wiping gently with a Kim-wipe. 10 ml of PBS was added to the petri dish containing the gels. The petri dishes were placed on an orbital shaker. The buffer was replaced at pre-determined time intervals. The retrieved buffer solutions were saved to analyze for residual Irgacure. At each time interval, the gel was wiped dry with a Kim Wipe and weighed. The percent swelling (% hydration) was calculated by the change in total weight as compared to the initial weight of the gel.

By qualitative assessment, the gels varied in gel strength in the following order (strongest gel to weakest gel): PEG8K>PEG3.4K>PEG2K. Gel strength was ascertained by degree of pliability, ease of handling, and brittleness. Gel strength was also noted to vary with concentration of the photoinitiator, with higher concentrations yielding hydrogels that were hard and brittle. Photoyellowing from Irgacure photoinitiation was noted in hydrogels in the following order (most photoyellowing to least photoyellowing): 5000 ppm>2500 ppm>1500 ppm>500 ppm. The photoinitiator concentration of 500 ppm and a PEGDA molecular weight of 8K resulted in the highest gel strength.

The following procedures were performed to incorporate glucose oxidase (GOx) into the gels. First, the gels were tested for residual Irgacure 2959. Next a glucose oxidase solution was prepared. The glucose oxidase was then loaded into the PEGDA hydrogels. The glucose oxidase concentration in the gels was measured. Lastly, the bioactivity of the gels was measured. The following describes these steps in detail.

The hydrogels were washed twice with buffer until there was no detectable residual Irgacure extracted from the hydrogels. The wash solutions were scanned on the UV-Vis from 200-400 nm, for the presence of Irgacure 2959. Non-detectable levels of Irgacure were determined to be an absorbance at 280 nm<0.010, equivalent to 0.13 ppm, as compared to a 25 ppm Irgacure solution that had an absorbance of 1.8 at 280 nm.

An LPT buffer solution was prepared by mixing 5% w/v glucose oxidase in PBS solution with 0.25 M lactic acid and 0.05% Triton X-100. This was accomplished by adding 0.5 grams of GOx to a total volume of 10 ml of a stock solution comprised of 0.25 M lactic acid and 0.05% Triton X-100 dissolved in PBS. The solution was kept at 4° C.

PEGDA hydrogels comprised of varying PEG molecular weights (2K, 3.4K, 8K) were soaked in the glucose oxidase solution. The gels were soaked for overnight or longer at 4° C., but no more than seven days.

Figure 18:
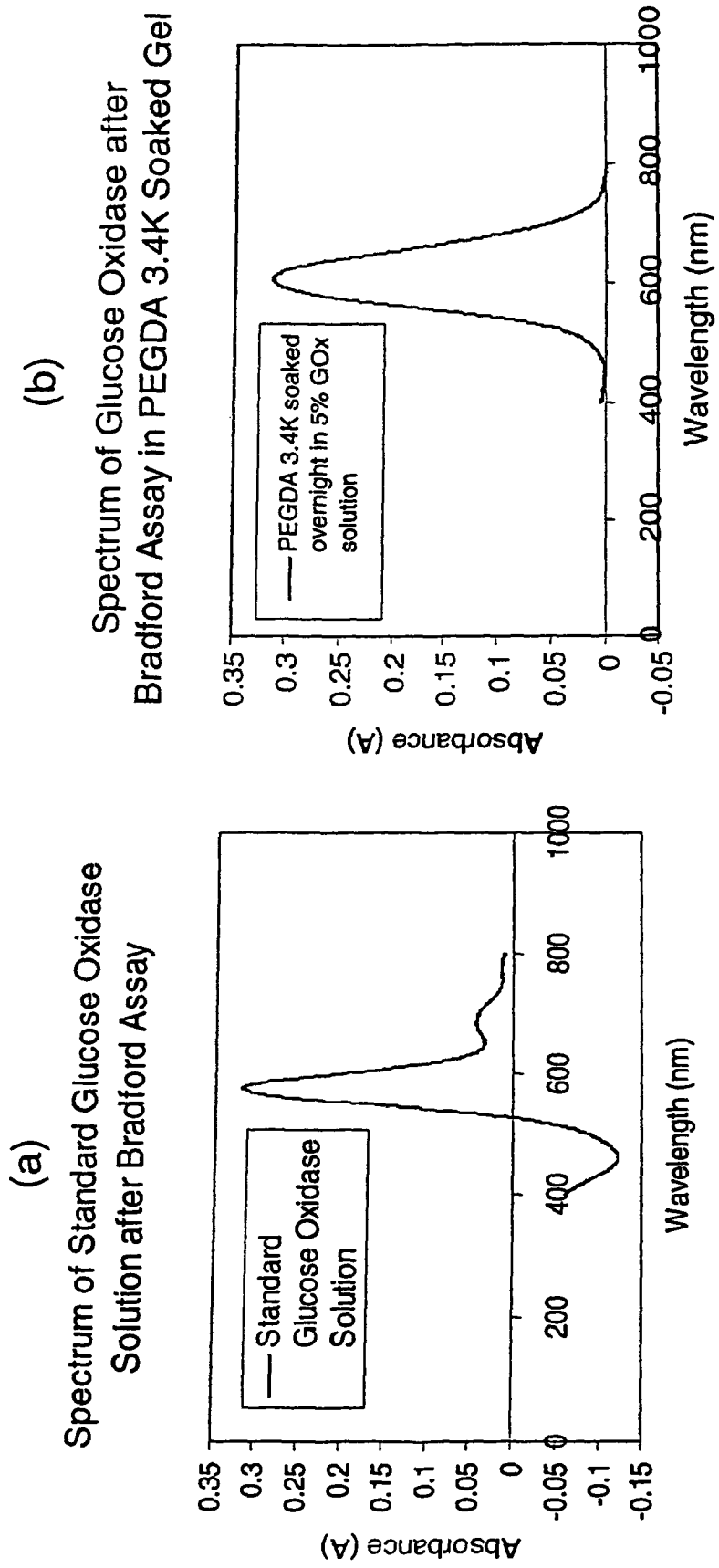
FIG. 18 shows the absorbance spectrum of a standard glucose oxidase solution before and after incorporation into a PEGDA 3.4K gel.

Glucose oxidase concentrations were measured by the Bradford Assay, a method commonly used to determine concentrations of solubilized protein. The method involves addition of an acidic blue dye (Coomassie Brilliant Blue G-250) to a protein solution. The dye binds primarily to basic and aromatic amino acid residues, especially arginine, with the absorption maximum shifting from 465 nm to 595 nm with complete dye-protein binding. The molar extinction coefficient of the dye-protein complex has been determined to be constant over a 10-fold concentration range; therefore, Beer-Lambert's Law can be utilized to accurately determine concentrations of protein. A standard curve of glucose oxidase solutions at concentrations 0.125%, 0.25%, 0.375%, 0.5% and 2.5% w/v was obtained by UV-Vis Spectroscopy at 595 nm after treatment of the standard solutions and the gel fragments with standard Bradford protein assay dye procedure. See Bradford Assay, BioRad Laboratories Brochure. A linear correlation of 0.999 was obtained for the standard curve. GOx incorporation in the hydrogels was determined in the following method: (a) a piece of gel was soaked in 4 ml LPT solution containing 1 ml of protein assay dye concentrate, (b) A piece of GOx-soaked then dyed (Coomassie dye) hydrogel was sandwiched between two glass cuvettes, (c) a non-GOx soaked and dyed hydrogel was used in the reference cell, (d) The gels were scanned from 400-800 nm and (e) the concentration of GOx incorporated in the hydrogels were calculated from Beer Lambert's Law: $A=\epsilon bc$, where $A$=absorbance, $\epsilon$=molar extinction coefficient, $b$=path length and $c$=concentration of the analyte. Concentrations of glucose oxidase incorporated in 2K, 3.4K and 8K molecular weight PEG hydrogels were determined. FIG. 18(*a*) is a UV-Vis spectrum of a standard glucose oxidase solution. FIG. 18(*b*) is an UV-Vis spectrum of Coomassie-bound glucose oxidase. The concentration in the gels is approximately 0.6%.

Figure 19:
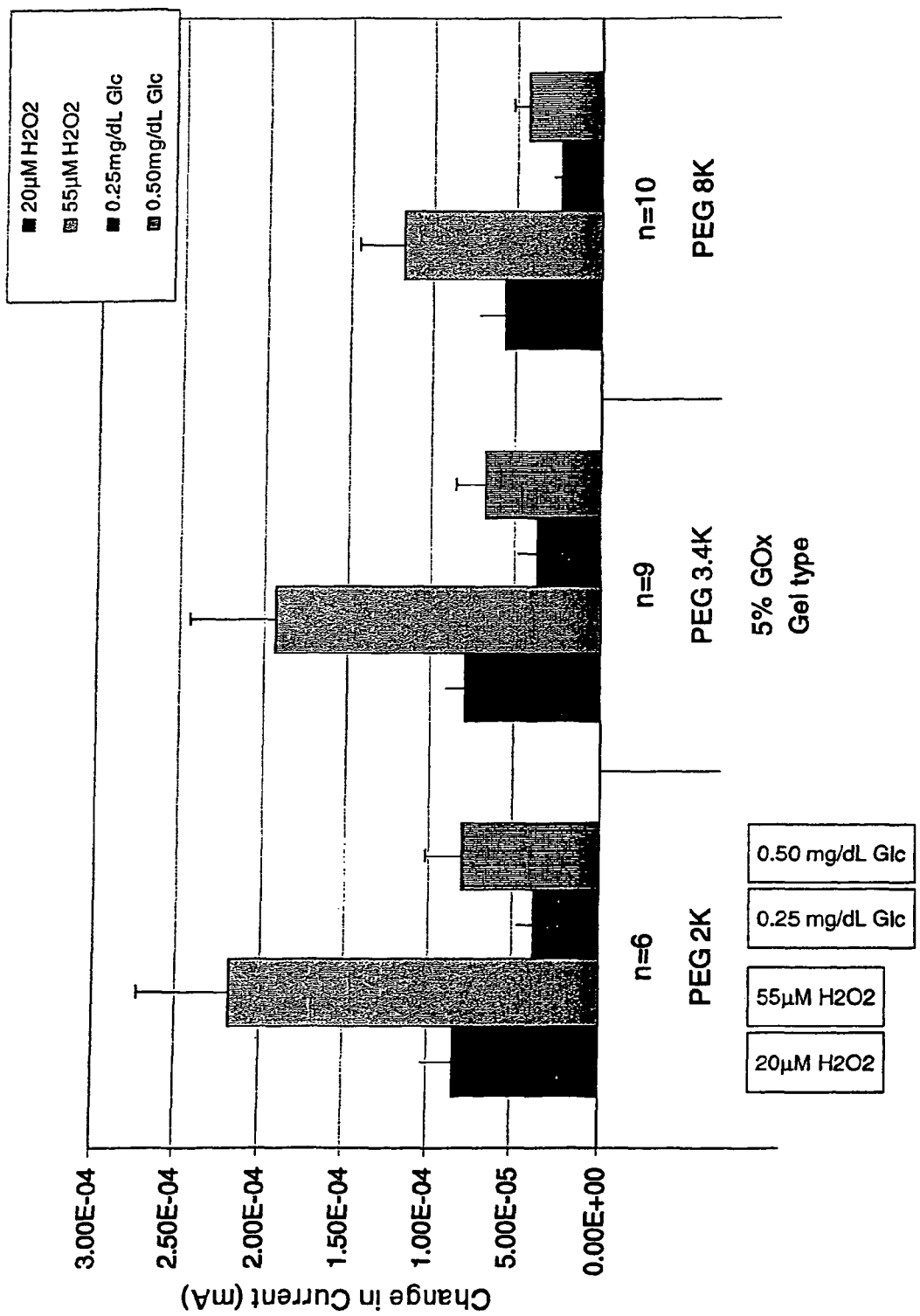
FIG. 19 shows the signal response to glucose of glucose oxidase (GOx) loaded PEG gels of varying molecular weight.
Figure 20:
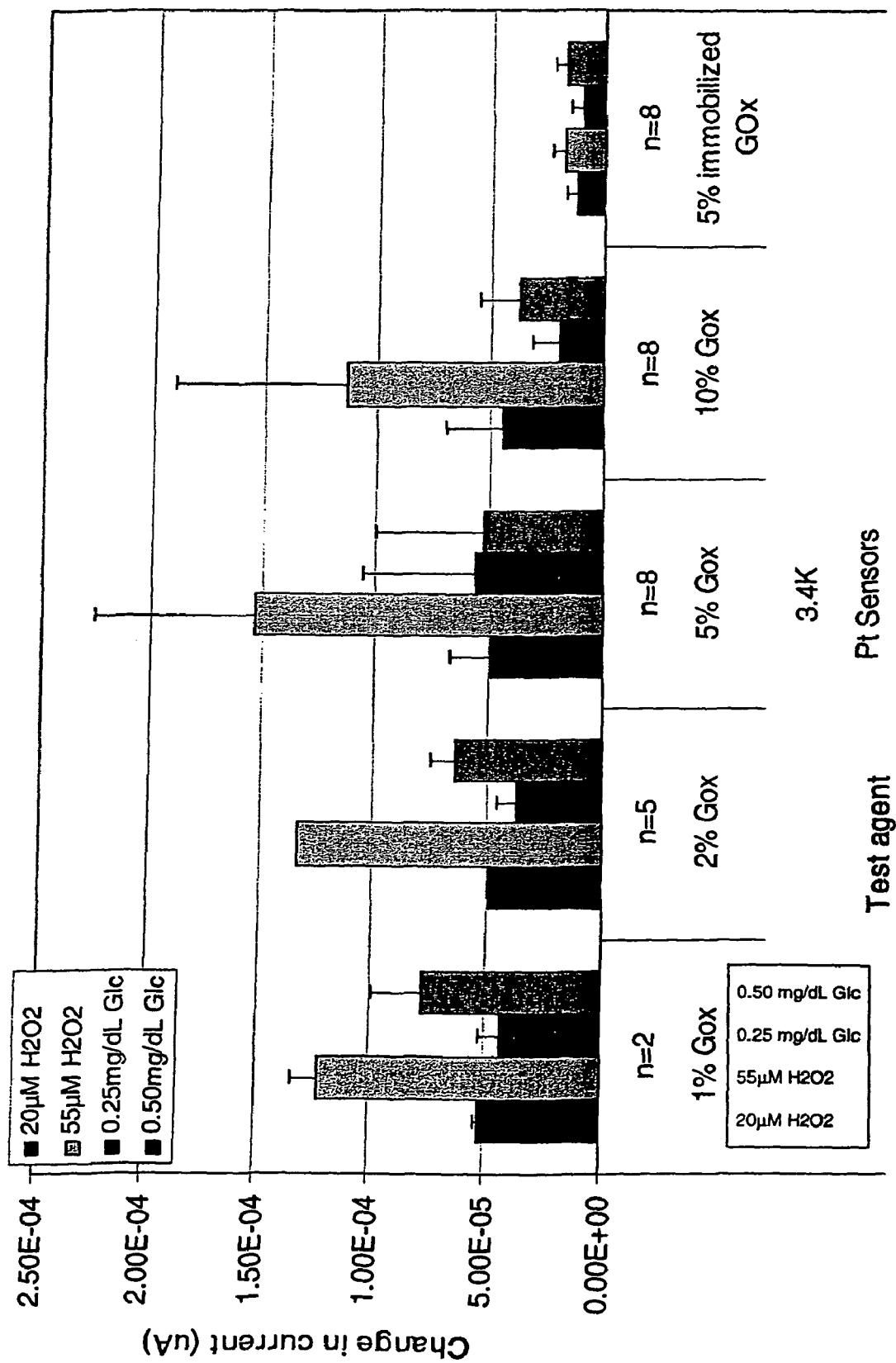
FIG. 20 shows signal response to glucose of 3.4K PEG hydrogel loaded with varying concentrations of GOx.
Figure 21:
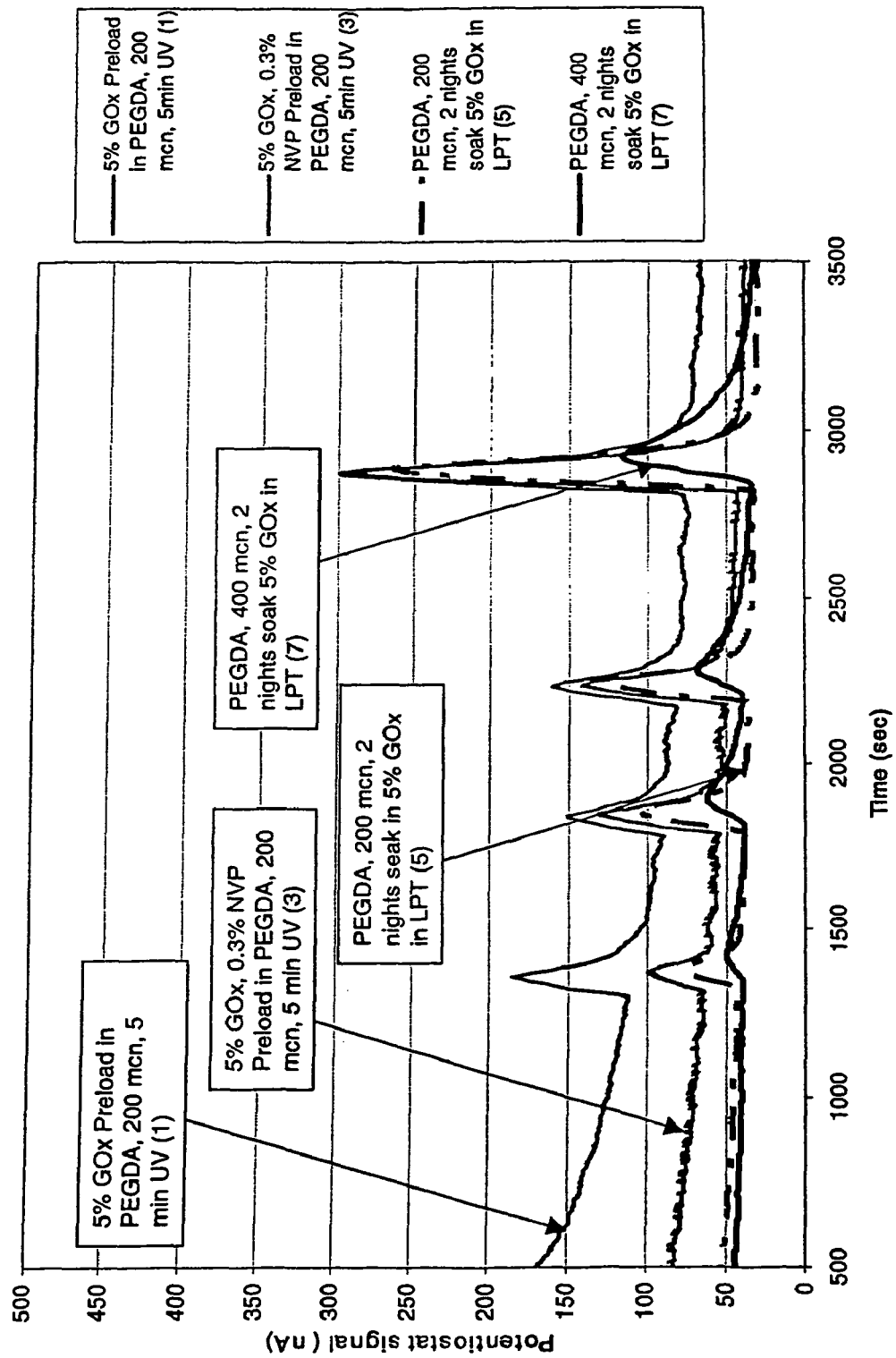
FIG. 21 shows raw data of the potentiometric signals elicited from PEGDA hydrogels with GOx incorporated in the gel formulation prior to photocrosslinking.
Figure 22:
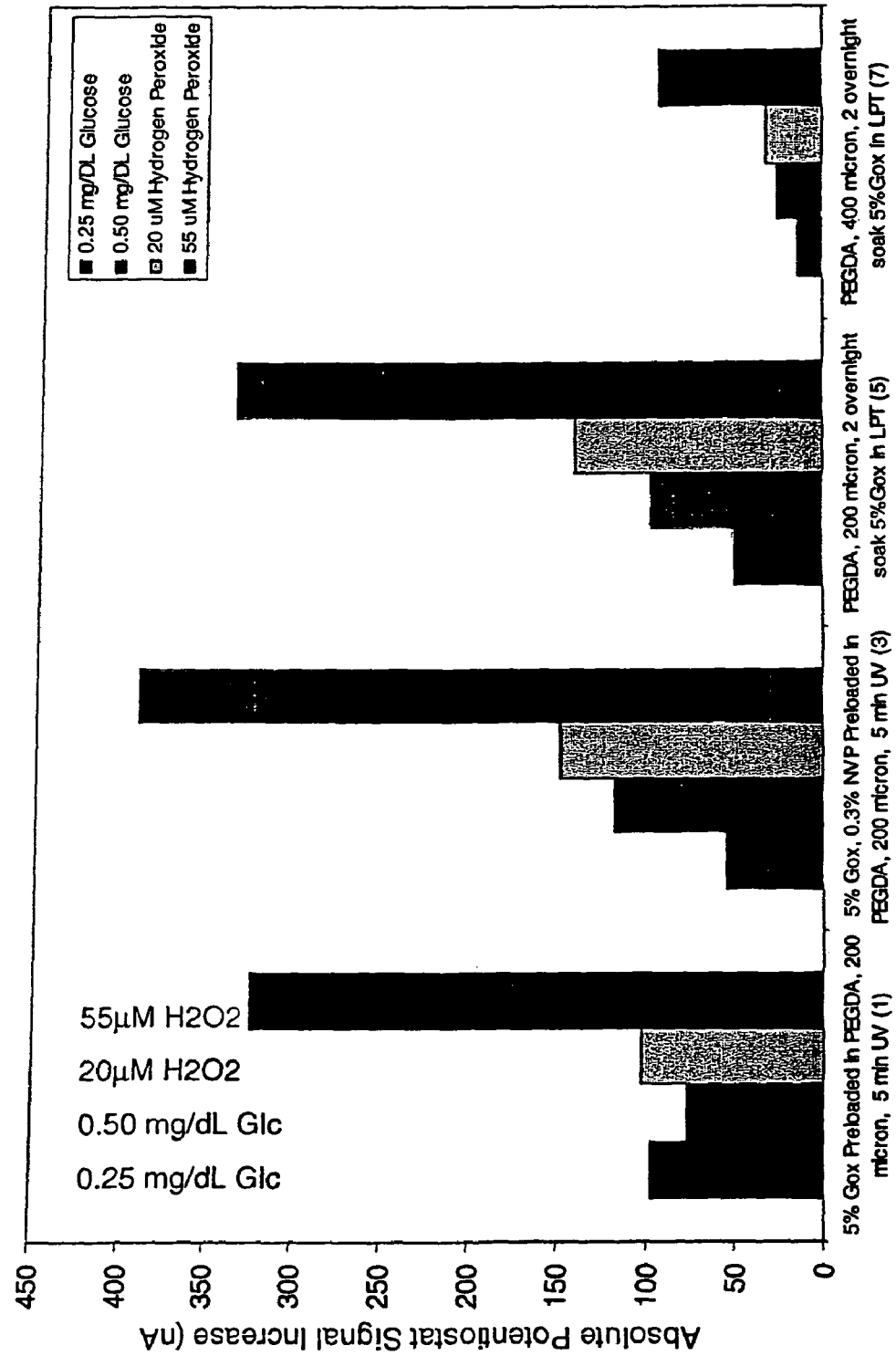
FIG. 22 shows the change in signal between GOx-presoaked versus pre-incorporated hydrogels at different thickness and compositions (PEGDA-nVP, PEGDA)
Figure 23:
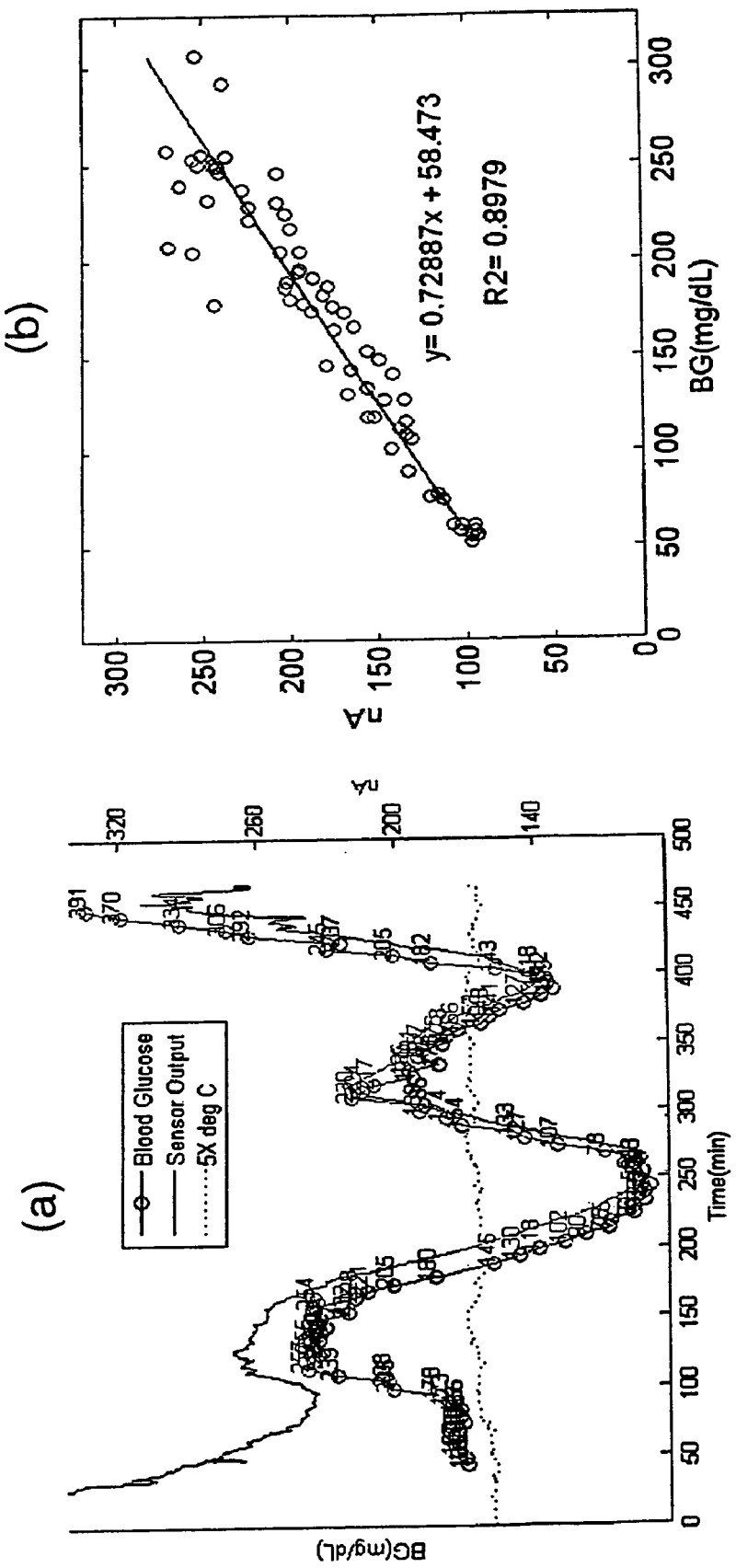
FIG. 23(a) shows blood glucose versus time utilizing an embodiment of the continuous transdermal analyte monitoring system.
FIG. 23(b) shows a correlation plot of electrode signal in nanoamps versus blood glucose for an embodiment of the invention.

Electrochemical sensors were used to test the enzymatic activity of the hydrogel-incorporated GOx. Prior to the placement on sensor, the PEGDA hydrogels are cut to the diameter of the sensor surface and rinsed briefly in LPT to remove surface residual GOx. Solutions of glucose (0.25 and 0.50 mg/dl) in PBS were used as the standard test solutions and solutions of hydrogen peroxide (20 and 55 µM) in PBS were used as the positive controls. Hydrogen peroxide, the reaction product of glucose and GOx, produced amperometric current, which was recorded by a potentiostat connecting to the sensor. Therefore, positive sensor signal in response to a glucose challenge (addition of glucose) indicates that the incorporated enzyme was bioactive, while a positive sensor signal in response to a hydrogen peroxide challenge (addition of hydrogen peroxide) indicates that the eletrochemical sensor is functioning. PEGDA hydrogels with incorporated GOx were tested for peak signal strength and baseline stability. These tests demonstrate that all hydrogels (2K, 3.4K, 8K) contain bioactive GOx, and that 2K and 3.4K are advantageous for signal strength and baseline stability (See FIGS. 19-20). FIG. 19 shows the signal response to glucose of glucose oxidase loaded PEG gels of varying molecular weight. FIG. 19 demonstrates that the PEG gels contain bioactive GOx and that 2K and 3.4K molecular weight PEG hydrogels are advantageous for signal strength and baseline stability. FIG. 20 shows signal response to glucose of PEG3.4K-diacrylate hydrogel loaded with varying concentrations of GOx in the gel as well as for GOx immobilized on the sensor surface. The label "n" in FIGS. 19-20 corresponds to the number of data sets that were taken with respect to each condition tested. FIG. 21 shows the raw data of the potentiometric signals elicited from PEGDA hydrogels with GOx incorporated in the gel formulation prior to photocrosslinking. The data from FIG. 21 demonstrates that hydrogels with a thickness of 400 µm had significant non-Gaussian peak shapes and tailing relative to gels at 200 µm, which is indicative of slow diffusion of glucose and hydrogen peroxide through the hydrogel. FIG. 22 shows the change in signal between GOx-presoaked versus pre-incorporated, i.e., pre-loaded, hydrogels at different gel thickness and gel compositions (PEGDA-nVP, PEGDA). Among the variations of gels tested were PEGDA hydrogels at varied thickness (200 µm, 400 µm) and PEGDA-nVP at 200 µm. The data from FIG. 22 demonstrates that the GOx incorporated in the hydrogels is bioactive. Baseline stability was acceptable for all formulations and signals were not compromised.

The following describes ex vivo glucose testing on a patient with diabetes using GOx loaded PEGDA hydrogel in a complete sensor assembly. The ultrasonic skin permeation procedure, sensing mechanism, sensor configuration and protocols for clinical trials are described in Chuang H, Taylor E, and Davison T., "Clinical Evaluation of a Continuous Minimally Invasive Glucose Flux Sensor Placed Over Ultrasonically Permeated Skin," Diabetes Technology & Therapeutics, 6:21-30 (2004). In this clinical trial, PEGDA3.4K and pure platinum were used as the hydrogel and sensor materials, respectively.

Glucose sensor function using PEGDA hydrogel is shown in FIGS. 23(a)-(b). FIG. 23(a) shows an example of sensor signal (nA) responding continuously to changes of blood glucose (BG) levels in a glucose-clamping clinical study over a period of seven hours. The corresponding nA-BG correlation plot shown in FIG. 23b has a Perason's correlation coefficient R=0.9476 ($R^2$ square=0.8979), revealing excellent sensor's function to monitor BG levels. Use of GOx loaded PEGDA hydrogel enables successful, continuous transdermal glucose monitoring.

Example 6

PEG-diacrylate-n-vinyl pyrrolidone-GOx hydrogels (PEGDA-NVP) for use with glucose monitoring were prepared according to the following procedures. PEGDA-NVP are slightly cationic, which provides ionic interaction that retains GOx. Incorporating GOx within the hydrogel prior to crosslinking also contributes to physical entrapment of GOx in the matrix. PEGDa-NVP hydrogels were prepared and characterized according to the following procedure.

100 mg of dry polymer was weighed into a tared scintillation vial. 500 µl PBS containing 1000 ppm of Irgacure 2959, 250 µl of 20% GOx in PBS, and 150 µl of 2% n-vinyl pyrrolidone ("n-VP") was added to the vial and the final weight of the solution was recorded. The vial was screw-capped and the vial swirled gently to dissolve the PEGDA. The gel solution was stored in the drawer (in the dark) for 5 minutes to ensure homogeneity. 900 µl of the gel solution was placed between two glass plates (200µ spacers) and clamped. The glass assembly containing the polymer solution was placed under an UV Blak-Ray lamp, at an intensity of 15-20 mW/cm$^2$ and cured for 5 minutes. The gel was removed carefully from the glass and weighed before transferring to 10 ml of LPT in a plastic petri dish.

The 200 micron hydrogels were transparent, easy to handle, pliable with considerable gel strength, as assessed qualitatively. Water content of the hydrogels were approximately 90%. The GOx was incorporated in the hydrogels prior to crosslinking, resulting in semi-interpenetrating networks. The hydrogels retained their yellow color (due to the GOx), post hydration. This indicated higher retention of the enzyme within the hydrogel.

Bioactivity of the incorporated enzyme was determined by potentiometry. This experiment demonstrated that glucose oxidase incorporated with PEG diacrylate-n-vinyl pyrrolidone hydrogels is bioactive and chemically compatible with the hydrogel delivery system. Data in FIGS. 21-22 demonstrate that GOx incorporated within the hydrogels are bioactive and functional.

Example 7

PEG-diacrylate/Polyethyleneimine (PEGDA-PEI) hydrogels for use with glucose monitoring can be prepared according to the following procedures. PEGDA-PEI are cationic hydrogels. Polyethyleneimine (branched, or dendrimer, Sigma Chemicals) can be incorporated within PEG diacrylate hydrogels to impart cationic character. A cationic hydrogel can ionically interact with slightly anionic glucose oxidase to provide a controlled release reservoir for the enzyme. A solution comprised of 0.3-0.5% PEI, 10% PEGDA, 500 ppm Irgacure 2959 and 5% glucose oxidase can be photocrosslinked with a BlakRay UV light, as described in previous sections. Incorporation of the highly cationic PEI can provide a high-binding substrate for GOx resulting in enhanced retention of the enzyme in the matrix. Furthermore, the highly cationic character of the hydrogels can provide the added functionality of bioadhesivity to the skin. Other cationic, bioadhesive macromolecules that can be incorporated into PEGDA hydrogels are chitosan, polyamidoamine, poly (n-vinyl pyrrolidone), etc.

Figure 16:
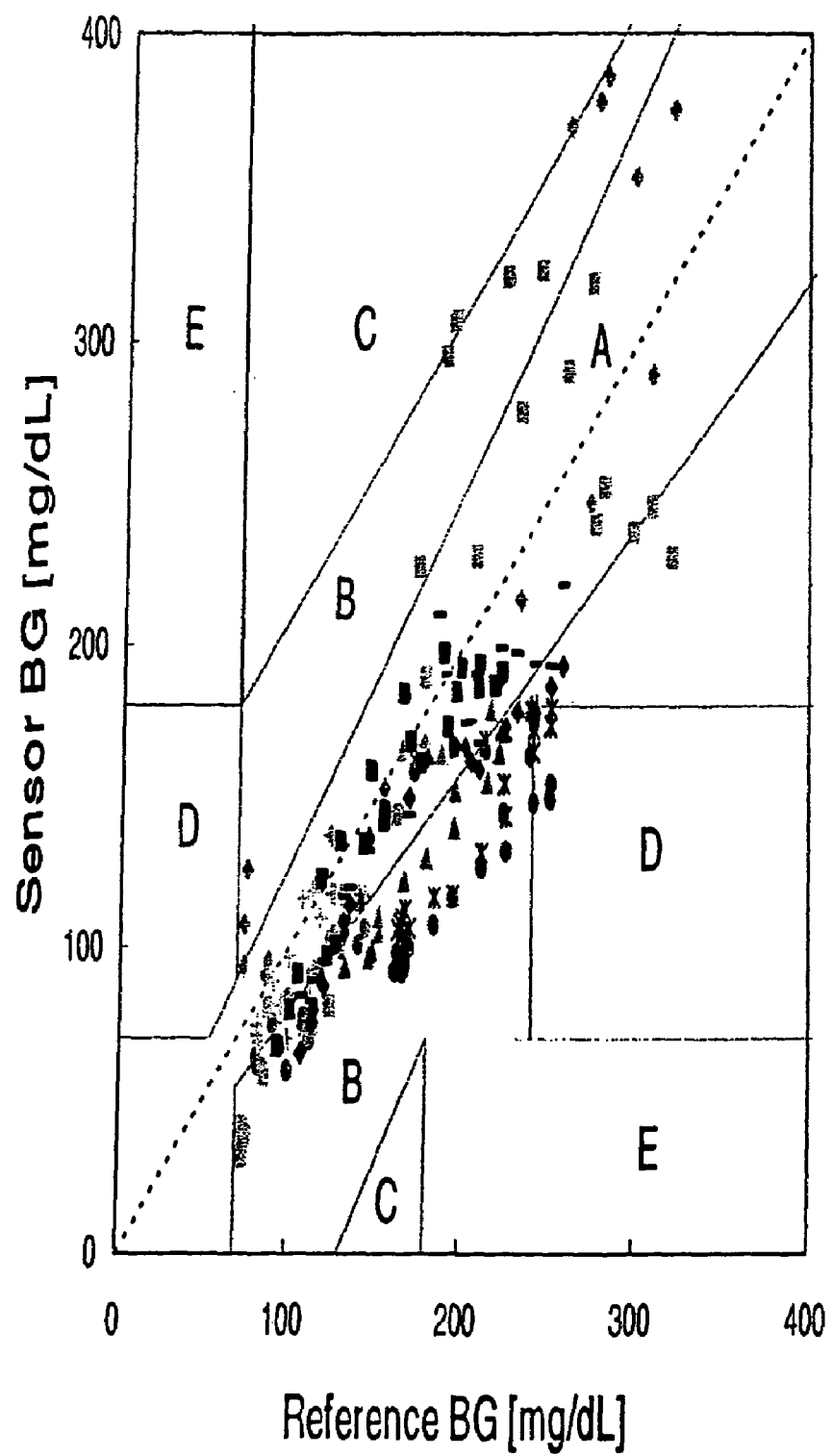
FIG. 16 shows a Clark Error Grid in the absence of an error correction method according to one embodiment of the invention.
Figure 17:
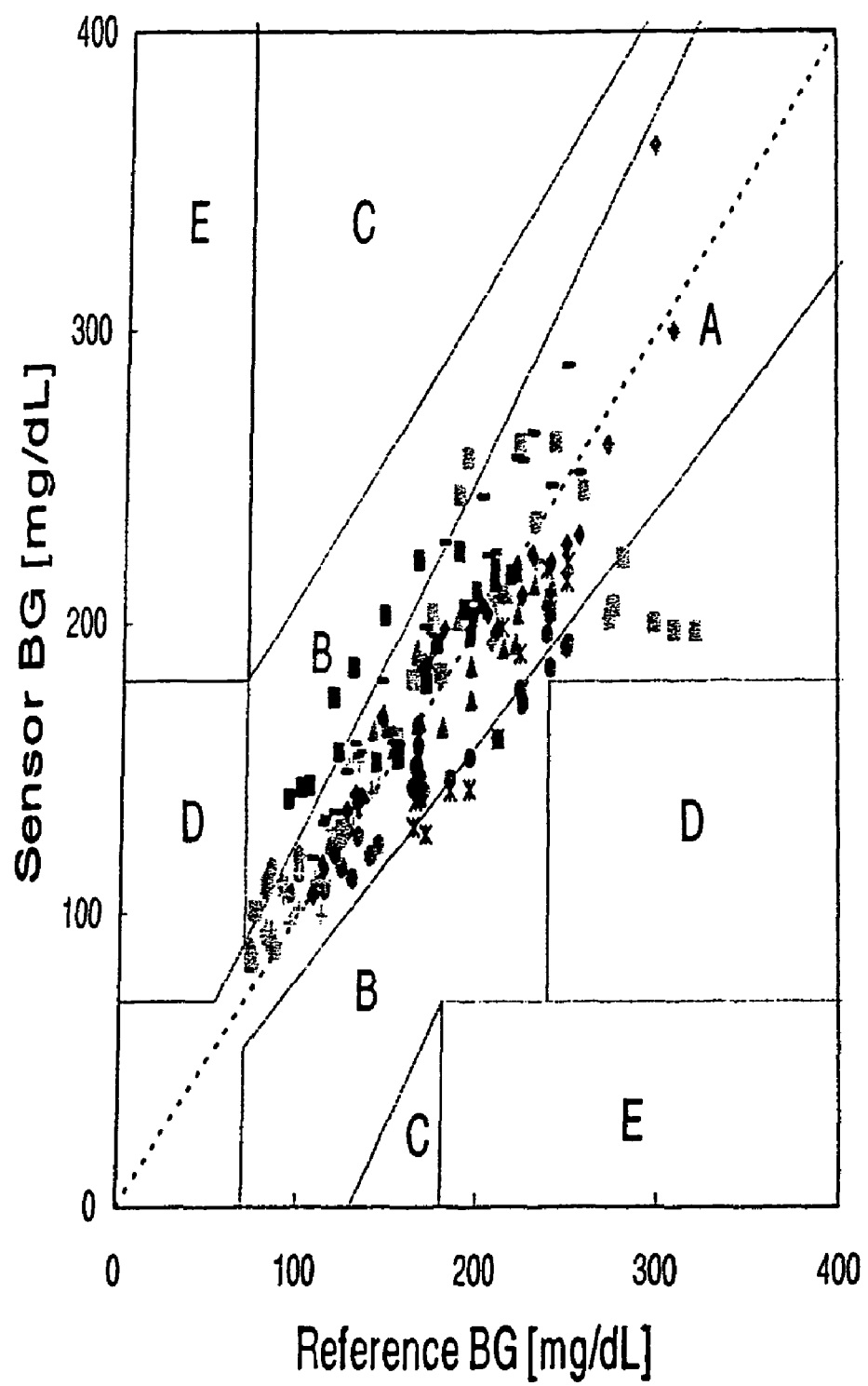
FIG. 17 shows a Clark Error Grid after the application of an error correction method according to an embodiment of the invention.

According to another aspect of the invention, an error correction method can be utilized to correct for sensor drift in a measured blood glucose value as a function of time. FIG. 16 shows a Clark Error Grid without the error correction method to correct for sensor drift. The data in FIG. 16 were taken from ten ex vivo tests on diabetic subjects in a clinical trial. The different data labels indicate data from different patients. FIG. 17 shows the Clark Error Grid after application of the error correction method to correct sensor drift. The data in FIG. 17 were taken from ten ex vivo tests on diabetic subjects in a clinical trial. The error correction method is described below.

The sensor signal, Y, as a function of time, t, is related to the sensor sensitivity, m, blood glucose value, X, and a constant offset value, b, according to the following linear relationship:

$$Y = mX(t) + b$$

The above equation can be rearranged, and the blood glucose value can be conveniently predicted with a single point calibration protocol as follows:

$$X(t) = (Y-b)/m, \text{ and } m = (Yc-b)/Xrc(t)$$

The value of sensor sensitivity, m, can be found from each ex vivo study using the sensor's current reading Yc and a standard reference blood glucose value Xrc(t) at the sensor calibration time point. When comparing subsequent blood glucose value, X(t), with corresponding standard reference blood glucose value Xr(t), it is found that a drift factor D(t) can be computed at different points as follows:

$$D(t) = Xr(t)/X(t)$$

By plotting D(t) vs. time, t, from a bulk number of successful ex vivo studies, a best fit for the D(t) vs. t plot was a third order polynomial function, which can be represented as follows:

$$D(t)=c*t^3+d*t^2+e*t+f$$

where c, d, e, f are numerical coefficients calculated to provide the best fit for the D(t) vs. t data to the above third order polynomial. The use of a third order polynomial is, however, exemplary and other methods of representing the drift factor such as an algorithm fitting the drift data to an exponential function, or utilizing a direct look-up table method can also be utilized.

To predict a drift-corrected blood glucose value Xp(t) at time t, one can simply multiply X(t) by D(t) as follows:

$$Xp(t)=X(t)*D(t)=X(t)*(c*t^3+d*t^2+e*t+f)$$

This equation represents an error correction method, and its utility may be appreciated by a comparison of the Clark Error Grid where the algorithm is not applied (FIG. 16) versus where it is applied (FIG. 17). The negative bias and wide scattering of data pairs in FIG. 16 is effectively corrected, and as a result all data points fall in the clinically relevant A and B regions in the Clark Error Grid, as shown in FIG. 17. This error correction method may be applied to data generated using the continuous transdermal analyte monitoring system according an exemplary embodiment of the present invention.

Other embodiments and uses of the invention will be apparent to those skilled in the art from consideration of the specification and practice of the invention disclosed herein. All references cited herein, including all U.S. and foreign patents and patent applications, are specifically and entirely hereby incorporated herein by reference. It is intended that the specification and examples be considered exemplary only, with the true scope and spirit of the invention indicated by the following claims.

What is claimed is:

1. A sensor assembly for a transdermal analyte monitoring system comprising:

a polyethylene glycol diacrylate macromer based hydrogel adapted to interface with permeabilized skin of a subject and to receive an analyte through the skin, wherein the polyethylene glycol diacrylate macromer has a molecular weight of 2000 to 8000 Da and is cross-linked in the presence of an enzyme to form a network of cross-linked macromer that entraps at least a portion of the enzyme;

an electrode assembly comprising at least a first and second electrode, the first and second electrodes being arranged adjacent to each other on a surface of the a sensor body and positioned adjacent the hydrogel;

wherein during operation the sensor assembly is positioned adjacent a permeabilized skin of the subject such that the enzyme reacts continuously with the analyte received through the subject's skin and an electrical signal which correlates to an analyte value is detected by the electrode assembly.

2. The sensor assembly claim 1, wherein the analyte value is the flux of the analyte through the subject's skin.

3. The sensor assembly of claim 1, wherein the analyte value is the concentration of the analyte in the subject's body fluid.

4. The sensor assembly of claim 1, wherein the analyte comprises glucose.

5. The sensor assembly of claim 4, wherein the enzyme is glucose oxidase.

6. The sensor assembly of claim 1, wherein the hydrogel comprises 1-10% glucose oxidase.

7. The sensor assembly of claim 1, wherein the polyethylene glycol diacrylate macromer has a molecular weight of about 3,400 Da.

8. The sensor assembly of claim 1, wherein the hydrogel has a thickness of about 200 micrometers.

9. The sensor assembly of claim 1, wherein the polyethylene glycol diacrylate macromer is a polyethylene glycol diacrylate-n-vinyl pyrrolidone macromer.

* * * * *